US007910544B2

(12) United States Patent
Gardella et al.

(10) Patent No.: US 7,910,544 B2
(45) Date of Patent: Mar. 22, 2011

(54) CONFORMATIONALLY CONSTRAINED PARTHYROID HORMONE (PTH) ANALOGS

(75) Inventors: Thomas J. Gardella, Needham, MA (US); Naoto Shimizu, Shizuoka (JP); Henry M. Kronenberg, Belmont, MA (US); John T. Potts, Jr., Newton, MA (US)

(73) Assignee: The General Hospital Corporation, Boston, MA (US)

( * ) Notice: Subject to any disclaimer, the term of this patent is extended or adjusted under 35 U.S.C. 154(b) by 930 days.

(21) Appl. No.: 10/564,744

(22) PCT Filed: Jul. 16, 2004

(86) PCT No.: PCT/US2004/022830
§ 371 (c)(1),
(2), (4) Date: Mar. 3, 2006

(87) PCT Pub. No.: WO2005/009358
PCT Pub. Date: Feb. 3, 2005

(65) Prior Publication Data
US 2007/0203071 A1 Aug. 30, 2007

Related U.S. Application Data

(60) Provisional application No. 60/487,589, filed on Jul. 17, 2003.

(51) Int. Cl.
*A61K 38/29* (2006.01)
(52) U.S. Cl. .............. 514/2; 514/13; 514/14; 514/15; 530/326; 530/327; 530/328
(58) Field of Classification Search .................. None
See application file for complete search history.

(56) References Cited

U.S. PATENT DOCUMENTS

| | | | |
|---|---|---|---|
| 4,086,196 A | 4/1978 | Tregear |
| 4,366,241 A | 12/1982 | Tom et al. |
| 4,423,037 A | 12/1983 | Rosenblatt et al. |
| 4,511,502 A | 4/1985 | Builder et al. |
| 4,512,922 A | 4/1985 | Jones et al. |
| 4,518,526 A | 5/1985 | Olson |
| 4,620,948 A | 11/1986 | Builder et al. |
| 4,675,189 A | 6/1987 | Kent et al. |
| 4,698,328 A | 10/1987 | Neer et al. |
| 4,736,866 A | 4/1988 | Leder et al. |
| 4,761,406 A | 8/1988 | Flora et al. |
| 4,843,000 A | 6/1989 | Litman et al. |
| 4,849,338 A | 7/1989 | Litman et al. |
| 5,010,010 A | 4/1991 | Gautvik et al. |
| 5,208,041 A | 5/1993 | Sindrey |
| 5,217,896 A | 6/1993 | Kramer et al. |
| 5,227,487 A | 7/1993 | Haugland et al. |
| 5,274,113 A | 12/1993 | Kang et al. |
| 5,326,692 A | 7/1994 | Brinkley et al. |
| 5,350,836 A | 9/1994 | Kopchick et al. |
| 5,382,658 A | 1/1995 | Kronis et al. |
| 5,393,869 A | 2/1995 | Nakagawa et al. |
| 5,405,975 A | 4/1995 | Kuhn et al. |
| 5,433,896 A | 7/1995 | Kang et al. |
| 5,442,045 A | 8/1995 | Haugland et al. |
| 5,451,663 A | 9/1995 | Kang et al. |
| 5,453,517 A | 9/1995 | Kuhn et al. |
| 5,457,034 A | 10/1995 | della Valle et al. |
| 5,459,276 A | 10/1995 | Kuhn et al. |
| 5,462,856 A | 10/1995 | Lerner et al. |
| 5,494,806 A | 2/1996 | Segre et al. |
| 5,496,801 A | 3/1996 | Holthuis et al. |
| 5,501,979 A | 3/1996 | Geller et al. |
| 5,516,864 A | 5/1996 | Kuhn et al. |
| 5,527,772 A | 6/1996 | Holick |
| 5,556,940 A | 9/1996 | Willick et al. |
| 5,573,909 A | 11/1996 | Singer et al. |
| 5,578,461 A | 11/1996 | Sherwin et al. |
| 5,589,452 A | 12/1996 | Krstenansky et al. |
| 5,605,815 A | 2/1997 | Broadus et al. |
| 5,616,560 A | 4/1997 | Geddes et al. |
| 5,648,270 A | 7/1997 | Kuhn et al. |
| 5,656,465 A | 8/1997 | Panicali et al. |
| 5,693,616 A | 12/1997 | Krstenansky et al. |
| 5,695,955 A | 12/1997 | Krstenansky et al. |
| 5,717,062 A | 2/1998 | Chorev et al. |
| 5,723,218 A | 3/1998 | Haugland et al. |
| 5,723,577 A | 3/1998 | Dong |
| 5,741,486 A | 4/1998 | Pathak et al. |
| 5,763,416 A | 6/1998 | Bonadio et al. |

(Continued)

FOREIGN PATENT DOCUMENTS

AU 668118 4/1996

(Continued)

OTHER PUBLICATIONS

Barden, J.A. and Kemp, B.E., "NMR Solution Structure of Human Parathyroid Hormone(1-34)," *Biochemistry* 32:7126-7132, American Chemical Society (1993).

Behar, V., et al., "Photoaffinity Cross-linking Identifies Differences in the Interactions of an Agonist and an Antagonist with the Parathyroid Hormone/Parathyroid Hormone-related Protein Receptor," *J. Biol. Chem.* 275:9-17, American Society for Biochemistry and Molecular Biology, Inc. (2000).

Bergwitz, C., et al., "Full Activation of Chimeric Receptors by Hybrids between Parathyroid Hormone and Calcitonin," *J. Biol. Chem.* 271:26469-26472, The American Society for Biochemistry and Molecular Biology, Inc. (1996).

Berridge, M.J., et al., "Changes in the levels of inositol phosphates after agonist-dependent hydrolysis of membrane phosphoinositides," *Biochem. J.* 212:473-482, The Biochemical Society (1983).

(Continued)

*Primary Examiner* — Anish Gupta
(74) *Attorney, Agent, or Firm* — Clark & Elbing LLP

(57) ABSTRACT

The invention provides novel P1R polypeptide antagonists. These antagonists contain amino acid substitutions at selected positions in truncated PTH and PRHrP polypeptides and function by binding selectively to the juxtamembrane ("J") domain of the receptor. The J domain is the region of the receptor that spans the seven transmembrane domain and the extracellular loops.

39 Claims, 11 Drawing Sheets

U.S. PATENT DOCUMENTS

| | | | |
|---|---|---|---|
| 5,798,225 | A | 8/1998 | Krstenansky et al. |
| 5,807,823 | A | 9/1998 | Krstenansky et al. |
| 5,814,603 | A * | 9/1998 | Oldenburg et al. ............. 514/12 |
| 5,821,225 | A | 10/1998 | Vickery |
| 5,836,905 | A | 11/1998 | Lemelson et al. |
| 5,840,690 | A | 11/1998 | Holick |
| 5,840,837 | A | 11/1998 | Krstenansky et al. |
| 5,840,853 | A | 11/1998 | Segre et al. |
| 5,854,004 | A | 12/1998 | Czernilofsky et al. |
| 5,871,486 | A | 2/1999 | Huebner et al. |
| 5,874,086 | A | 2/1999 | Krstenansky et al. |
| 5,880,093 | A | 3/1999 | Bagnoli |
| 5,886,148 | A | 3/1999 | Segre et al. |
| 5,917,123 | A | 6/1999 | McTiernan et al. |
| 5,922,927 | A | 7/1999 | Bujard et al. |
| 5,977,070 | A | 11/1999 | Piazza et al. |
| 6,030,790 | A | 2/2000 | Adermann et al. |
| 6,051,686 | A | 4/2000 | Krstenansky et al. |
| 6,066,618 | A | 5/2000 | Holick |
| 6,147,186 | A | 11/2000 | Gardella et al. |
| 6,183,974 | B1 | 2/2001 | Bringhurst et al. |
| 6,362,163 | B1 | 3/2002 | Gardella et al. |
| 6,417,333 | B1 | 7/2002 | Bringhurst et al. |
| 6,495,662 | B1 | 12/2002 | Gardella et al. |
| 6,537,965 | B1 | 3/2003 | Bringhurst et al. |
| 6,541,220 | B1 | 4/2003 | Jüppner et al. |
| 6,756,480 | B2 | 6/2004 | Kostenuik et al. |
| 6,803,213 | B2 | 10/2004 | Bringhurst et al. |
| 7,022,815 | B1 | 4/2006 | Gardella et al. |
| 7,033,773 | B1 | 4/2006 | Bringhurst et al. |
| 7,057,012 | B1 | 6/2006 | Gardella et al. |
| 7,078,487 | B2 | 7/2006 | Jüppner et al. |
| 7,132,260 | B2 | 11/2006 | Segre et al. |
| 7,150,974 | B1 | 12/2006 | Segre et al. |
| 7,153,951 | B2 | 12/2006 | Gardella et al. |
| 7,169,567 | B1 | 1/2007 | Gardella et al. |
| 7,244,834 | B2 | 7/2007 | Gardella et al. |
| 7,253,264 | B1 | 8/2007 | Lauffer et al. |
| 7,371,844 | B2 | 5/2008 | Gardella et al. |
| 7,479,478 | B2 | 1/2009 | Bringhurst et al. |
| 7,521,528 | B2 | 4/2009 | Gardella et al. |
| 7,572,765 | B2 | 8/2009 | Gardella |
| 2002/0110871 | A1 | 8/2002 | Zahradnik et al. |
| 2003/0144209 | A1 | 7/2003 | Bringhurst et al. |
| 2003/0162256 | A1 | 8/2003 | Juppner et al. |
| 2003/0166838 | A1 | 9/2003 | Gardella et al. |
| 2003/0171288 | A1 | 9/2003 | Stewart |
| 2004/0176285 | A1 | 9/2004 | Juppner et al. |
| 2005/0026839 | A1 | 2/2005 | Gardella |
| 2005/0124537 | A1 | 6/2005 | Kostenuik et al. |
| 2005/0203012 | A1 | 9/2005 | Bringhurst et al. |
| 2005/0282749 | A1 | 12/2005 | Henriksen et al. |
| 2006/0078559 | A1 | 4/2006 | Migeotte et al. |
| 2007/0111946 | A1 | 5/2007 | Gardella et al. |
| 2007/0161569 | A1 | 7/2007 | Gardella |

FOREIGN PATENT DOCUMENTS

| | | |
|---|---|---|
| CA | 2126132 | 12/1995 |
| CA | 2126299 | 12/2000 |
| EP | 0 341 962 | 11/1989 |
| EP | 0 464 533 | 1/1992 |
| EP | 0 477 885 | 4/1992 |
| EP | 0 561 412 | 9/1993 |
| EP | 0 748 817 | 12/1996 |
| EP | 0 783 522 | 7/1997 |
| GB | 2 269 176 | 2/1994 |
| JP | 58-96052 | 7/1983 |
| JP | 59-204159 | 11/1984 |
| JP | 5-32696 | 2/1993 |
| JP | 9-157294 | 6/1997 |
| WO | WO 87/01130 | 2/1987 |
| WO | WO 92/01810 | 2/1992 |
| WO | WO 92/17581 | 10/1992 |
| WO | WO 92/17602 | 10/1992 |
| WO | WO 93/06121 | 4/1993 |
| WO | WO 93/06846 | 4/1993 |
| WO | WO 93/09222 | 5/1993 |
| WO | WO 93/11257 | 6/1993 |
| WO | WO 94/02510 | 2/1994 |
| WO | WO 94/12650 | 6/1994 |
| WO | WO 95/02610 | 1/1995 |
| WO | WO 95/11988 | 5/1995 |
| WO | WO 96/03437 | 2/1996 |
| WO | WO 96/10041 | 4/1996 |
| WO | WO 96/19206 | 6/1996 |
| WO | WO 97/02834 | 1/1997 |
| WO | WO 91/05050 | 4/1997 |
| WO | WO 98/05683 | 2/1998 |
| WO | WO 98/30590 | 7/1998 |
| WO | WO 99/18945 | 4/1999 |
| WO | WO00/23594 * | 4/2000 |
| WO | WO 00/31137 | 6/2000 |
| WO | WO 00/31266 | 6/2000 |
| WO | WO 00/32771 | 6/2000 |
| WO | WO 00/32775 | 6/2000 |
| WO | WO 00/39278 | 7/2000 |
| WO | WO 00/40698 | 7/2000 |
| WO | WO 01/23427 | 4/2001 |
| WO | WO 01/23521 | 4/2001 |
| WO | WO 03/009804 A2 | 2/2003 |
| WO | WO 2004/067021 | 8/2004 |
| WO | WO 2004/093902 | 11/2004 |
| WO | WO 2005/009358 | 2/2005 |
| WO | WO 2008/019062 | 2/2008 |
| WO | WO 2009/017809 | 2/2009 |

OTHER PUBLICATIONS

Bisello, A., et al., "Parathyroid Hormone-Receptor Interactions Identified Directly by Photocross-linking and Molecular Modeling Studies," *J. Biol. Chem.* 273:22498-22505, The American Society for Biochemistry and Molecular Biology, Inc. (1998).

Carter, P.H and Gardella, T.J., "Zinc(II)-mediated enhancement of the agonist activity of histidine-substituted parathyroid hormone(1-14) analogues," *Biochem. Biophysc. Acta* 1538:290-304, Elsevier Science B.V. (2001).

Chen, Z., et al., "Structure of the Osteogenic 1-31 Fragment of Human Parathyroid Hormone," *Biochemistry* 39:12766-12777, American Chemical Society (2000).

Condon, S.M., et al., "The Bioactive Conformation of Human Parathyroid Hormone. Structural Evidence for the Extended Helix Postulate," *J. Am. Chem. Soc.* 122:3007-3014, American Chemical Society (2000).

Creighton, T.E., ed., "3.2. Evolutionary Divergence of Proteins," in: *Proteins: Structures and Molecular Properties*, $2^{nd}$ Ed., W.H. Freeman and Co., NewYork, NY, pp. 108-114 (1993).

Dempster, D.W., et al., "Anabolic Actions of Parathyroid Hormone on Bone," *Endocrine Rev.* 14:690-709, The Endocrine Society (1993).

Dempster, D.W., et al., "Erratum: Anabolic Actions of Parathyroid Hormone on Bone," *Endocrine Rev.* 15:261, The Endocrine Society (1994).

Dempster, et al., "On the Mechanism of Cancellous Bone Preservation in Postmenopausal Women with Mild Primary Hyperparathyroidism," *J. Clinical Endocrinology & Metabolism* 84:1562-1566, The Endocrine Society (1999).

Fairwell, T., et al., "Total Solid-Phase Synthesis, Purification, and Characterization of Human Parathyroid Hormone-(1-84)," *Biochemistry* 22:2691-2697, American Chemical Society (1983).

Gardella, T.J., et al., "Analysis of Parathyroid Hormone's Principal Receptor Binding Region by Site-Directed Mutagenesis and Analog Design," *Endocrinol.* 132:2024-2030, Endocrine Society (1993).

Gronwald, W., et al., "Structure of Recombinant Human Parathyroid Hormone in Solution Using Multidimensional NMR Spectroscopy," *Chem. Hoppe-Seyler* 377:175-186, Walter de Gruyter & Co. (1996).

Goud, N.A., et al., "Solid-Phase Synthesis and Biologic Activity of Human Parathyroid Horrnone(1-84)," *J. Bone Min. Res.* 6:781-789, Mary Ann Liebert, Inc. (1991).

Hoare, S.R.J., et al., "Evaluating the Signal Transduction Mechanism of the Parathyroid Hormone 1 Receptor," *J. Biol. Chem.* 276:7741-7753, American Society for Biochemistry and Molecular Biology (2001).

Jin, L., et al., "Crystal Structure of Human Parathyroid Hormone 1-34 at 0.9-Å Resolution," *J. Biol. Chem.* 275:27238-27244, The American Society for Biochemistry and Molecular Biology, Inc. (2000).

Jüppner, H., et al., "A G Protein-Linked Receptor for Parathyroid Hormone and Parathyroid Hormone-Related Peptide," *Science* 254:1024-1026, American Society for the Advancement of Science (1991).

Kronenberg, H.M., et al., "Parathyroid Hormone: Biosynthesis, Secretion, Chemistry, and Action" in: *Handbook of Experimental Pharmacology*, Mundy, G.R., and Martin, T.J., eds., Springer-Verlag, Berlin, Germany, pp. 507-567 (1993).

Luck, M.D., et al., "The (1-14) Fragment of Parathyroid Hormone (PTH) Activates Intact and Amino-Terminally Truncated PTH-1 Receptors," *Mol. Endocrinol.* 13:670-680, The Endocrine Society (1999).

Marx, U.C., et al., "Structure of Human Parathyroid Hormone 1-37 in Solution," *J. Biol. Chem.* 270:15194-15202, The American Society for Biochemistry and Molecular Biology, Inc. (1995).

Marx, U.C., et al., "Structure Activity Relation of $NH_2$-Terminal Human Parathyroid Hormone Fragments," *J. Biol. Chem* 273:4308-4316, American Society for Biochemistry and Molecular Biology, Inc. (1998).

Marx, U.C., et al., "Solution Structure of Human Parathyroid Hormone Fragments hPTH(1-34) and hPTH (1-39) and Bovine Parathyroid Hormone Fragment bPTH(1-37)," *Biochem. Biophys. Res. Commun.* 267:213-220, Academic Press (2000).

Neer, R.M., et al., "Effect of Parathyroid Hormone (1-34) on Fractures and Bone Mineral Density in Postmenopausal Women with Osteoporosis," *N. Eng. J. Med.* 344:1434-1441, Massachusetts Medical Society (2001).

Pellegrini, M., et al., "Binding Domain of Human Parathyroid Hormone Receptor: From Conformation to Function," *Biochemistry* 37:12737-12743, American Chemical Society (1998).

Robinson J.R. ed., "Methods to Achieve Controlled Drug Delivery," in: *Sustained and Controlled Release Drug Delivery Systems*, Marcel Dekker, New York, NY, pp. 557-593 (1978).

Rölz, C. And Mierke, D.F., "Characterization of the molecular motions of constitutively active G protein-coupled receptors for parathyroid hormone," *Biophys. Chem.* 89:119-128, Elsevier Science B.V. (2001).

Shimizu, M., et al., "Autoactivation of Type-1 Parathyroid Hormone Receptors Containing a Tethered Ligand," *J. Biol. Chem.* 275:19456-19460, The American Society for Biochemistry and Molecular Biology, Inc. (2000).

Shimizu, M., et al., "Minimization of Parathyroid Hormone," *J. Biol. Chem.* 275:21836-21834, The American Society for Biochemistry and Molecular Biology, Inc. (2000).

Shimizu, M., et al., "Enhanced Activity in Parathyroid Hormone-(1-14) and -(1-11): Novel Peptides for Probing Ligand-Receptor Interactions," *Endocrinol.* 142:3068-3074, Endocrine Society (2001).

Shimizu, N., et al., "Parathyroid Hormone (PTH)-(1-14) and -(1-11) Analogs Conformationally Constrained by α-Aminosobutyric Acid Mediate Full Agonist Responses via the Juxtamembrane Region of the PTH-1 Receptor," *J. Biol. Chem.* 276:49003-49012, The American Society for Biochemistry and Molecular Biology, Inc. (2001).

Slovik, D.M., et al., "Restoration of Spinal Bone in Osteoporotic Men by Treatment with Human Parathyroid Hormone (1-34) and 1,25-Dihydroxyvitamin D," *J. Bone Min. Res.* 1:377-381, Mary Ann Liebert, Inc. (1986).

Takasu, H., et al., "Amino Terminal Modifications of Human Parathyroid Hormone (PTH) Selectively Alter Phospholipase C Signaling via The Type 1 PTH Receptor: Implications of Design of Signal-Specific PTH Ligands," *Biochemistry* 38:13453-13460, American Chemical Society (1999).

Tregear, G.W., et al., "Bovine Parathyroid Hormone: Minimum Chain Length of Synthetic Peptide Required for Biological Activity," *Endocrinol.* 93:1349-1353, The Endocrine Society (1973).

Wold, F., "Posttranslational Protein Modifications: Perspectives and Prospects," in *Posttranslational Covalent Modifications of Proteins*, B.C. Johnson, eds., Academic Press, Inc., New York, pp. 1-12 (1983).

Gensure et al., "Identification of a Contact Site for Residue 19 of Parathyroid Hormone (PTH) and PTH-Related Protein Analogs in Transmembrane Domain Two of the Type 1 PTH Receptor," *Mol Endocrinol*. Dec. 2003; 17(12):2647-58.

Shimizu et al. "Amino-Terminal Parathyroid Hormone Fragment Analogs Containing α,α-di-alkyl Amino Acids at Positions 1 and 3," *J Bone Miner Res*. Sep. 20, 2004;19(12):2078-86.

Shimizu et al., "Functional Evidence for an Intramolecular Side Chain Interaction between Residues 6 and 10 of Receptor-Bound Parathyroid Hormone Analogues," *Biochemistry*. Mar. 4, 2003; 42(8):2282-90.

Supplementary European Search Report for application No. EP 04 77 8370, dated Jul. 3, 2009.

Abou-Samra et al., "Phorbol 12-Myristate 13-Acetate and Vasopressin Potentiate the Effect of Corticotropin- Releasing Factor on Cyclic AMP Production in Rat Anterior Pituitary Cells. Mechanisms of Action," *J. Biol. Chem.* 262: 1129-1136 (1987).

Abou-Samra et al., "Non-Homologous Sequences of Parathyroid Hormone and the Parathyroid Hormone Related Peptide Bind to a Common Receptor on ROS 17/2.8 Cells," *Endocrinology* 125: 2215-2217 (1989).

Abou-Samra et al., "Cyclic Adenosine 3', 5'-Monophosphate (cAMP)-Dependent and cAMP-Independent Regulation of Parathyroid Hormone Receptors on UMR 106-01 Osteoblastic Osteosarcoma Cells," *Endocrinology* 129: 2547-2554 (1991).

Abou-Samra et al., "Expression Cloning of a Common Receptor for Parathyroid Hormone and Parathyroid Hormone-Related Peptide From Rat Osteoblast-Like Cells: A Single Receptor Stimulates Intracellular Accumulation of Both cAMP and Inositol Trisphosphates and Increases Intracellular Free Calcium," *Proc. Natl. Acad. Sci. USA* 89: 2732-2736 (1992).

Abou-Samra et al., "Down-Regulation of Parathyroid (PTH)/PTH-Related Peptide Receptor Immunoreactivity and PTH Binding in Opossum Kidney Cells by PTH and Dexamethasone," *Endocrinology* 135: 2588-2594 (1994).

Adams et al., "Probing the Bimolecular Interactions of Parathyroid Hormone and the Human Parathyroid Hormone/Parathyroid Hormone-Related Protein Receptor. 2. Cloning, Characterization, and Photoaffinity Labeling of the Recombinant Human Receptor," *Biochemistry* 34: 10553-10559 (1995).

Alberts et al., "Chapter 6: Basic Genetic Mechanisms" in: *Molecular Biology of the Cell, 3rd Edition*, pp. 234-237 and the Genetic Code Table (Garland Pub., New York, NY, 1994).

Azarani et al., "Parathyroid Hormone and Parathyroid Hormone-Related Peptide Acticate the NA+ /H+ Exchanger NHE-1 Isoform in Osteoblastic Cells (UMR-106) via a cAMP-dependent Pathway," *J. Biol. Chem.* 270: 23166-23172 (1995).

Azarani et al., "Structurally Diverse N-terminal Peptides of Parathyroid Hormone (PTH) and PTH-Related Peptide (PTHRP) Inhibit the Na+/H+ Exchanger NHE3 Isoform by Binding to the PTH/PTHRP Receptor Type I and Activating Distinct Signaling Pathways," *J. Biol. Chem.* 271: 14931-14936 (1996).

Barbier et al., "Bioactivities and Secondary Structures of Constrained Analogues of Human Parathyroid Hormone: Cyclic Lactams of the Receptor Binding Region," *J. Med. Chem.* 40: 1373-1380 (1997).

Barbier et al., "Structural Requirements for Conserved Arginine of Parathyroid Hormone," *Biochemistry* 40: 8955-8961 (2001).

Barbier et al., "Backbone-Methylated Analogues of the Principle Receptor Binding Region of Human Parathyroid Hormone. Evidence for Binding to Both the N-Terminal Extracellular Domain and Extracellular Loop Region," *J. Biol. Chem.* 280: 23771-23777 (2005).

Barden et al., "NMR Study of a 34-Residue N-Terminal Fragment of a Parathyroid Hormon-Related Protein Secreted During Humoral Hypercalcemia of Malignancy," *Eur. J. Biochem.* 184: 379-394 (1989).

Barden et al., "Stabilized NMR Structure of the Hypercalcemia of Malignancy Peptide PTHrP[Ala-26](1-34)Amide," *Biochim. Biophys. Acta* 1208: 256-262 (1994).

Becker et al., "Procedure Guideline for Thyroid Scintigraphy: 1.0. Society of Nuclear Medicine," *J. Nucl. Med.* 37: 1264-1266 (1996).

Behar et al., "Histidine at Position 5 is the Specificity "Switch" between Two Parathyroid Hormone Receptor Subtypes," *Endocrinology* 137: 4217-4224 (1996).

Bergwitz et al., "Residues in the Membrane-spanning and Extracellular Loop Regions of the Parathyroid Hormone (PTH)-2 Receptor Determine Signaling Selectivity for PTH and PTH-Related Peptide," *J. Biol. Chem.* 272: 28861-28868 (1997).

Bergwitz et al., "Identification, Functional Characterization, and Developmental Expression of Two Nonallelic Parathyroid Hormone (PTH)/PTH-Related Peptide Receptor Isoforms in Xenopus laevis (Daudin)," *Endocrinology* 139: 723-732 (1998).

Berlot, "A Highly Effective Dominant Negative Alpha s Construct Containing Mutations that Affect Distinct Functions Inhibits Multiple Gs-Coupled Receptor Signaling Pathways," *J. Biol. Chem.* 277: 21080-21085 (2002).

Bettoun et al., "Cloning and Characterization of the Promoter Regions of the Human Parathyroid Hormone (PTH)/PTH-Related Peptide Receptor Gene: Analysis of Deoxyribonucleic Acid from Normal Subjects and Patients with Pseudohypoparathyroidism Type 1b," *J. Clin. Endocrinol. Metab.* 82: 1031-1040 (1997).

Bettoun et al., "Developmental Upregulation of Human Parathyroid Hormone (PTH)/PTH-Related Peptide Receptor Gene Expression from Conserved and Human-specific Promoters," *J. Clin. Invest.* 102: 958-967 (1998).

Bisello et al., "Selective Ligand-Induced Stabilization of Active and Desensitized Parathyroid Hormone Type 1 Receptor Conformations," *J. Biol. Chem.* 277: 38524-38530 (2002).

Bork et al., "Go Hunting in Sequence Databases but Watch Out for the Traps," *Trends Genet.* 12: 425-427 (1996).

Bork, "Powers and Pitfalls in Sequence Analysis: the 70% Hurdle," *Genome Res.* 10: 398-400 (2000).

Born et al., "Inhibition of Parathyroid Hormone Bioactivity by Human Parathyroid Hormone (PTH)-(3-84) and PTH-(8-84) Synthesized in *Escherichia coli*," *Endocrinology* 123:1848-1853 (1988).

Bos et al., "Expression of the Parathyroid Hormone Receptor and Correlation with Other Osteoblastic Parameters in Fetal Rat Osteoblasts," *Calcif. Tisse Int.* 58:95-100 (1996).

Brenner, "Errors in Genome Annotation," *Trends Genet.* 15: 132-133 (1999).

Bringhurst et al., "Cloned, Stably Expressed Parathyroid Hormone (PTH)/PTH-Related Peptide Receptors Activate Multiple Messenger Signals and Biological Responses in LLC-PK1 Kidney Cells," *Endocrinology* 132: 2090-2098 (1993).

Broadus et al., "Parathyroid Hormone-Related Protein: Structure, Processing, and Physiological Actions," in: *The Parathyroids* (eds. J. P. Bilezikan et al.), pp. 259-294 (Raven Press Ltd., New York, NY, 1994).

Bryant et al., "Helix-Inducing α-Aminoisobutyric Acid in Opioid Mimetic Deltorphin C Analogues," *J. Med. Chem.* 40: 2579-2587 (1997).

Bundi et al., "Characterisation of a Local Structure in the Synthetic Parathyroid Hormone Fragment 1-34 by 1H Nuclear-Magnetic-Resonance Techniques," *Eur. J. Biochem.* 91: 201-208 (1978).

Campbell et al., "Totipotency or Multipotentiality of Cultured Cells: Applications and Progress," *Theriogenology* 47: 63-72 (1997).

Carter et al., "Studies of the N-Terminal Region of a Parathyroid Hormone-Related Peptide(1-36) Analog: Receptor Subtype-Selective Agonists, Antagonists, and Photochemical Cross-Linking Agents," *Endocrinology* 140: 4972-4981 (1999).

Castro et al., "Dual Regulation of the Parathyroid Hormone (PTH)/PTH-Related Peptide Receptor Signaling by Protein Kinase C and Beta-Arrestins," *Endocrinology* 143: 3854-3865 (2002).

Castro et al., "Turn-On Switch in Parathyroid Hormone Receptor by a Two-Step Parathyroid Hormone Binding Mechanism," *Proc. Natl. Acad. Sci. USA* 102: 16084-16089 (2005).

Catanzariti et al., "A Novel Expression System for Gs-Coupled Receptors," *BioTechniques* 15: 474-479 (1993).

Caulfield et al., "The Bovine Renal Parathyroid Hormone (PTH) Receptor has Equal Affinity for Two Different Amino Acid Sequences: The Receptor Binding Domains of PTH and PTH-related Protein are Located within the 14-34 Region," *Endocrinology* 127: 83-87 (1990).

Caulfield et al., "Parathyroid Hormone-Receptor Interactions," *Trends Endocrinol Metab.* 1: 164-168 (1990).

Cervini et al., "Human Growth Hormone-Releasing hGHRH(1-29)-NH2: Systematic Structure-Activity Relationship Studies," *J. Med. Chem.* 41: 717-727 (1998).

Chakrabartty, "Large Differences in the Helix Propensities of Alanine and Glycine," *Nature* 351: 586-588 (1991).

Chakravarthy et al., "Parathyroid Hormone Fragment [3-34] Stimulates Protein Kinase C (PKC) Activity in Rat Osteosarcoma and Murine T-lymphoma Cells," *Biochem. Biophys. Res. Commun.* 171: 1105-1110 (1990).

Chauvin et al., "Parathyroid Hormone Receptor Recycling: Role of Receptor Dephosphorylation and Beta-Arrestin," *Mol. Endocrinol.* 16: 2720-2732 (2002).

Chorev et al., "Modifications of Position 12 in Parathyroid Hormone and Parathyroid Hormone Related Protein: Toward the Design of Highly Potent Antagonists," *Biochemistry* 29: 1580-1586 (1990).

Chorev et al., "Cyclic Parathyroid Hormone Related Protein Antagonists: Lysine 13 to Aspartic Acid 17 [i to (i+4)] Side Chain to Side Chain Lactamization," *Biochemistry* 30: 5968-5974 (1991).

Chu et al., "Porcine Proparathyroid Hormone. Identification, Biosynthesis, and Partial Amino Acid Sequence," *Biochemistry* 14: 3631-3635 (1975).

Civitelli et al., "PTH Elevates Inositol Polyphosphates and Diacylglycerol in a Rat Osteoblast-Like Cell Line," *Am. J. Physiol.* 255: E660-667 (1988).

Civitelli et al., "Parathyroid Hormone-Related Peptide Transiently Increases Cytosolic Calcium in Osteoblast-Like Cells: Comparison with Parathyroid Hormone," *Endocrinology* 125: 1204-1210 (1989).

Cohen et al., "Analogues of Parathyroid Hormone Modified at Positions 3 and 6. Effects on Receptor Binding and Activation of Adenylyl Cyclase in Kidney and Bone," *J. Biol. Chem.* 266: 1997-2004 (1991).

Cole et al., "Regulation of Sodium-Dependent Phosphate Transport by Parathyroid Hormone in Opossum Kidney Cells: Adenosine 3', 5'-Monophosphate-Dependent and -Independent Mechanisms," *Endocrinology* 122: 2981-2989 (1988).

Colquhoun, "Binding, Gating, Affinity, and Efficacy: The Interpretation of Structure-Activity Relationships for Agonists and of the Effects of Mutating Receptors," *Br. J. Pharmacol.* 125: 924-947 (1998).

Cwirla et al., "Peptide Agonist of the Thrombopoietin Receptor as Potent as the Natural Cytokine," *Science* 276: 1696-1699 (1997).

Dang et al., "Gene Therapy and Translational Cancer Research," *Clin. Cancer Res.* 5: 471-474 (1999).

Dautzenberg et al., "Mapping of the Ligand-Selective Domain of the *Xenopus laevis* Corticotropin-Releasing Factor Receptor 1: Implications for the Ligand-Binding Site," *Proc. Natl. Acad. Sci. USA* 95: 4941-4946 (1998).

DeAlmeida et al., "Identification of Binding Domains of the Growth Hormone-Releasing Hormone Receptor by Analysis of Mutant and Chimeric Receptor Proteins," *Mol. Endocrinol.* 12: 750-765 (1998).

Dean et al., "Mechanisms of Ligand Binding to the Parathyroid Hormone (PTH)/PTH-Related Protein Receptor: Selectivity of a Modified PTH(1-15) Radioligand for GalphaS-Coupled Receptor Conformations," *Mol. Endocrinol.* 20: 931-943 (2006).

Ding et al., "A Single Amino Acid Determines the Immunostimulatory Activity of Interleukin 10," *J. Exp. Med.* 191: 213-223 (2000).

Doerks et al., "Protein Annotation: Detective Work for Function Prediction," *Trends Genet.* 14: 248-250 (1998).

Dohlman et al., "Model Systems for the Study of Seven-Transmembrane-Segment Receptors," *Annu. Rev. Biochem.* 60: 653-688 (1991).

Donahue et al., "Differential Effects of Parathyroid Hormone and Its Analogues on Cytosolic Calcium Ion and cAMP Levels in Cultured Rat Osteoblast-Like Cells," *J. Biol. Chem.* 263: 13522-13527 (1988).

Dong et al., "Demonstration of a Direct Interaction between Residue 22 in the Carboxyl-Terminal Half of Secretin and the Amino-Terminal Tail of the Secretin Receptor Using Photoaffinity Labeling," *J. Biol. Chem.* 274: 903-909 (1999).

Dunlay et al., "PTH Receptor Coupling to Phospholipase C is an Alternate Pathway of Signal Transduction in Bone and Kidney," *Am. J. Physiol.* 258: F223-F231 (1990).

Ebert et al., "A Moloney MLV-Rat Somatotropin Fusion Gene Produces Biologically Active Somatotropin in a Transgenic Pig," *Mol. Endocrinol.* 2: 277-283 (1988).

Epand, "Relationships Among Several Different Non-Homologous Polypeptide Hormones," *Mol. Cell Biochem.* 57: 41-47 (1983).

Fischer et al., "Human Parathyroid Hormone. Immunological Characterization of Antibodies Against a Glandular Extract and the Synthetic Amino-Terminal Fragments 1-12 and 1-34 and their Use in the Determination of Immunoreactive Hormone in Human Sera," *J. Clin. Invest.* 54: 1382-1394 (1974).

Freyaldenhoven et al., "Protein Kinase C Differentially Modulates PTH- and PGE2 -Sensitive Adenylate Cyclase in Osteoblast-Like Cells," *Am. J. Physiol.* 262: E87-E95 (1992).

Fujimori et al., "Dissociation of Second Messenger Activation by Parathyroid Hormone Fragments in Osteosarcoma Cells," *Endocrinology* 128: 3032-3039 (1991).

Fujimori et al., "Structure-Function Relationships of Parathyroid Hormone: Activation of Phospholipase-C, Protein Kinase-A and -C in Osteosarcoma Cells," *Endocrinology* 130:29-36 (1992).

Fukayama et al., "Mechanisms of Desensitization to Parathyroid Hormone in Human Osteoblast-Like SaOS-2 Cells," *Endocrinology* 131: 1757-1769 (1992).

Fukayama et al., "Role of Protein Kinase-A in Homologous Down-Regulation of Parathyroid Hormone (PTH)/PTH-Related Peptide Receptor Messenger Ribonucleic Acid in Human Osteoblast-Like SaOS-2 Cells," *Endocrinology* 134: 1851-1858 (1994).

Gaich et al., "Amino-Terminal Parathyroid Hormone-Related Protein: Specific Binding and Cytosolic Calcium Responses in Rat Insulinoma Cells," *Endocrinology* 132: 1402-1409 (1993).

Gardella et al., "Expression of Human Parathyroid Hormone-(1-84) in *Escherichia coli* as a Factor X-cleavable Fusion Protein," *J. Biol. Chem.* 265: 15854-15859 (1990).

Gardella et al., "Mutational Analysis of the Receptor-Activating Region of Human Parathyroid Hormone," *J. Biol. Chem.* 266: 13141-13146 (1991).

Gardella et al., "Scanning Mutagenesis of the 23-35 Region of Parathyroid Hormone Reveals Important Determinants of Receptor Binding," in: *Calcium Regulating Hormones and Bone Metabolism: Basic and Clinical Aspects* (eds. D.V. Cohn et al.), vol. 11, pp. 218-222 (Excerpta Medica, Amsterdam, 1992).

Gardella et al., "Determinants of [Arg2]PTH-(1-34) Binding and Signaling in the Transmembrane Region of the Parathyroid Hormone Receptor," *Endocrinology* 135: 1186-1194 (1994).

Gardella et al., "Parathyroid Hormone (PTH)-PTH-Related Peptide Hybrid Peptides Reveal Functional Interactions Between the 1-14 and 15-34 Domains of the Ligand," *J. Biol. Chem.* 270: 6584-6588 (1995).

Gardella et al., "Converting Parathyroid Hormone-Related Peptide (PTHrP) into a Potent PTH-2 Receptor Agonist," *J. Biol. Chem.* 271: 19888-19893 (1996).

Gardella et al., "Transmembrane Residues of the Parathyroid Hormone (PTH)/PTH-Related Peptide Receptor that Specifically Affect Binding and Signaling by Agonist Ligands," *J. Biol. Chem.* 271: 12820-12825 (1996).

Gensure et al., "Multiple Sites of Contact between the Carboxyl-Terminal Binding Domain of PTHrP-(1-36) Analogs and the Amino-Terminal Extracellular Domain of the PTH/PTHrP Receptor Identified by Photoaffinity Cross-Linking," *J. Biol. Chem.* 276: 28650-28658 (2001).

Gensure et al., "Parathyroid Hormone and Parathyroid Hormone-Related Peptide, and their Receptors," *Biochem. Biophys. Res. Commun.* 328: 666-678 (2005).

Goltzman et al., "Influence of Guanyl Nucleotides on Parathyroid Hormone-Stimulated Adenylyl Cyclase Activity in Renal Cortical Membranes," *Endocrinology* 103: 1352-1360 (1978).

Goltzmann et al., "Analysis of the Requirements for Parathyroid Hormone Action in Renal Membranes with the Use of Inhibiting Analogues," *J. Biol. Chem.* 250: 3199-3203 (1975).

Gombert et al., "Alanine and D-Amino Acid Scan of Human Parathyroid Hormone," in: *Peptides: Chemistry, Structure and Biology* (eds. P.T.P. Kaumaya et al.), pp. 661-662 (Mayflower Sci. Ltd., England, 1996).

Grace et al., "NMR Structure and Peptide Hormone Binding Site of the First Extracellular Domain of a Type B1 G Protein-Coupled Receptor," *Proc. Natl. Acad. Sci. USA* 101: 12836-12841 (2004).

Greenberg et al., "Mapping the Bimolecular Interface of the Parathyroid Hormone (PTH)-PTH1 Receptor Complex: Spatial Proximity between Lys(27) (of the Hormone Principal Binding Domain) and Leu(261) (of the First Extracellular Loop) of the Human PTH1 Receptor," *Biochemistry* 39: 8142-8152 (2000).

Guo et al., "Parathyroid Hormone (PTH)/PTH-Related Peptide Receptor Density Modulates Activation of Phospholipase C and Phosphate Transport by PTH in LLC-PK1 Cells," *Endocrinology* 136: 3884-3891 (1995).

Habashita et al., "Synthesis and Biological Activities of hPTH(1-34) Analogues: Modification of the Middle Part and C-terminal Alkylamides," in: *Peptide Science- Present and Future: Proceedings of the 1st International Peptide Symposium* (ed. Y. Shimonishi), pp. 711-713 (Kluwer Acad. Pub., Great Britain, 1997).

Hammer et al., "Genetic Engineering of Mammalian Embryos," *J. Anim. Sci.* 63: 269-278 (1986).

Heinrich et al., "Gene Encoding Parathyroid Hormone. Nucleotide Sequence of the Rat Gene and Deduced Amino Acid Sequence of Rat Preproparathyroid Hormone," *J. Biol. Chem.* 259: 3320-3329 (1984).

Heinrich et al., "Rat Parathyroid Hormone Gene, Exons II and III," Alignment result 8, SEQ ID No. 1, Database: GenEmbl, Accession No. K01268 (Apr. 27, 1993).

Hilliker et al., "Truncation of the Amino Terminus of PTH Alters Its Anabolic Activity on Bone in Vivo," *Bone* 19: 469-477 (1996).

Hjorth et al., "Constitutive Activity of Glucagon Receptor Mutants," *Mol. Endocrinol.* 12: 78-86 (1998).

Hoare et al., "Measurement of Agonist and Antagonist Ligand-Binding Parameters at the Human Parathyroid Hormone Type 1 Receptor: Evaluation of Receptor States and Modulation by Guanine Nucleotide," *J. Pharmacol. Exp. Ther.* 289: 1323-1333 (1999).

Holtmann et al., "Critical Contributions of Amino-terminal Extracellular Domains in Agonist Binding and Activation of Secretin and Vasoactive Intestinal Polypeptide Receptors. Studies of Chimeric Receptors," *J. Biol. Chem.* 270: 14394-14398 (1995).

Holtmann et al., "Molecular Basis and Species Specificity of High Affinity Binding of Vasoactive Intestinal Polypeptide by the Rat Secretin Receptor. Effect of Receptor-G-Protein Interaction on the Ligand Binding Mechanism and Receptor Conformation," *J. Pharmacol. Exp. Ther.* 279: 555-560 (1996).

Horiuchi et al., "A Parathyroid Hormone Inhibitor In Vivo: Design and Biological Evaluation of a Hormone Analog," *Science* 220: 1053-1055 (1983).

Horiuchi et al., "Evaluation of a Parathyroid Hormone Antagonist in an In Vivo Multiparameter Bioassay," *Am. J. Physiol.* 253: E187-192 (1987).

Hruska et al., "Stimulation of Inositol Trisphosphate and Diacylglycerol Production in Renal Tubular Cells by Parathyroid Hormone," *J. Clin. Invest.* 79: 230-239 (1987).

Iida-Klein et al., "Truncation of the Carboxyl-terminal Region of the Rat Parathyroid Hormone (PTH)/PTH-Related Peptide Receptor Enhances PTH Stimulation of Adenylyl Cyclase but Not Phospholipase C," *J. Biol. Chem.* 270: 8458-8465 (1995).

Iida-Klein et al., "Structural Requirements of Parathyroid Hormone/Parathyroid Hormone-Related Peptide Receptors for Phospholipase C Activation and Regulation of Phosphate Uptake," *Miner. Electrolyte Metab.* 21: 177-179 (1995).

Iida-Klein et al., "Mutations in the Second Cytoplasmic Loop of the Rat Parathyroid Hormone (PTH)/PTH-Related Protein Receptor Result in Selective Loss of PTH-stimulated Phospholipase C Activity," *J. Biol. Chem.* 272: 6882-6889 (1997).

Inomata et al., "Characterization of a Novel Parathyroid Hormone (PTH) Receptor with Specificity for the Carboxyl-Terminal Region of PTH-(1-84)," *Endocrinology* 136: 4732-4740 (1995).

Ishihara et al., "Molecular Cloning and Expression of a cDNA Encoding the Secretin Receptor," *EMBO J.* 10: 1635-1641 (1991).

Iwakura et al., "Effects of the Length of a Glycine Linker Connecting the N- and C-Termini of a Circularly Permuted Dihydrofolate Reductase," *Protein Eng.* 11: 707-713 (1998).

Jans et al., "LLC-PK1 Cell Mutants in cAMP Metabolism Respond Normally to Phorbol Esters," *FEBS Lett.* 205: 127-131 (1986).

Janulis et al., "Structure-Function Requirements of Parathyroid Hormone for Stimulation of 1,25-Dihydroxyvitamin D3 Production by Rat Renal Proximal Tubules," *Endocrinology* 133: 713-719 (1993).

Ji et al., "Human Choriogonadotropin Binds to a Lutropin Receptor with Essentially No N-terminal Extension and Stimulates cAMP Synthesis," *J. Biol. Chem.* 266: 13076-13079 (1991).

Jing et al., "GDNF-Induced Activation of the Ret Protein Tyrosine Kinase Is Mediated by GDNFR-alpha, a Novel Receptor for GDNF," *Cell* 85: 1113-1124 (1996).

Jobert et al., "Parathyroid Hormone-Induced Calcium Release from Intracellular Stores in a Human Kidney Cell Line in the Absence of Stimulation of Cyclic Adenosine 3',5'-Monophosphate Production," *Endocrinology* 138: 5282-5292 (1997).

Jouishomme et al., "The Protein Kinase-C Activation Domain of the Parathyroid Hormone," *Endocrinology* 130: 53-60 (1992).

Jouishomme et al., "Further Definition of the Protein Kinase C Activation Domain of the Parathyroid Hormone," *J. Bone Miner. Res.* 9: 943-949 (1994).

Joun et al., "Tissue-specific Transcription Start Sites and Alternative Splicing of the Parathyroid Hormone (PTH)/PTH-related Peptide (PTHrP) Receptor Gene: A New PTH/PTHrP Receptor Splice Variant that Lacks the Signal Peptide," *Endocrinology* 138: 1742-1749 (1997).

Jüppner et al., "The Parathyroid Hormone-Like Peptide Associated with Humoral Hypercalcemia of Malignancy and Parathyroid Hormone Bind to the Same Receptor on the Plasma Membrane of ROS 17/2.8 Cells," *J. Biol. Chem.* 263: 8557-8560 (1988).

Jüppner et al., "Properties of Amino-Terminal Parathyroid Hormone-Related Peptides Modified at Positions 11-13," *Peptides* 11: 1139-1142 (1990).

Jüppner et al., "The Extracellular Amino-Terminal Region of the Parathyroid Hormone (PTH)/PTH-related Peptide Receptor Determines the Binding Affinity for Carboxyl-Terminal Fragments of PTH-(1-34)," *Endocrinology* 134: 879-884 (1994).

Kappel et al., "Regulating Gene Expression in Transgenic Animals," *Curr. Op. Biotechnol.* 3: 548-553 (1992).

Karaplis et al., "Lethal Skeletal Dysplasia From Targeted Disruption of the Parathyroid Hormone-Related Peptide Gene," *Genes Dev.* 8: 277-289 (1994).

Kaufman et al., "Transgenic Analysis of a 100-kb Human Beta-Globin Cluster-Containing DNA Fragment Propagated as a Bacterial Artificial Chromosome," *Blood* 94: 3178-3184 (1999).

Kaufmann et al., "Functional Expression of a Stably Transfected Parathyroid Hormone/Parathyroid Hormone Related Protein Receptor Complementary DNA in CHO cells," *Mol. Cell. Endocrinol.* 104: 21-27 (1994).

Kaul et al., "Stereochemical Control of Peptide Folding," *Bioorg. Med. Chem.* 7: 105-117 (1999).

Kemp et al., "Parathyroid Hormone-Related Protein of Malignancy: Active Synthetic Fragments," *Science* 238: 1568-1570 (1987).

Kimura et al., "Strategy for the Synthesis of Large Peptides: An Application to the Total Synthesis of Human Parathyroid Hormone [hPTH)1-84)]," *Biopolymers* 20: 1823-1832 (1981).

Kimura et al., "Discovery of a Novel Thrombopoietin Mimic Agonist Peptide," *J. Biochem.* 122: 1046-1051 (1997).

Klaus et al., "Investigation of the Solution Structure of the Human Parathyroid Hormone Fragment (1-34) by 1H NMR Spectroscopy, Distance Geometry, and Molecular Dynamics Calculations," *Biochemistry* 30: 6936-6942 (1991).

Kolakowski, "GCRDb: A G-Protein-Coupled Receptor Database," *Receptors and Channels* 2: 1-7 (1994).

Kong et al., "The Rat, Mouse and Human Genes Encoding the Receptor for Parathyroid Hormone and Parathyroid Hormone-Related Peptide are Highly Homologous," *Biochem. Biophys. Res. Commun.* 200: 1290-1299 (1994).

Kovacs et al., "Parathyroid Hormone-Related Peptide (PTHrP) Regulates Fetal-placental Calcium Transport Through a Receptor Distinct from the PTH/PTHrP Receptor," *Proc. Natl. Acad. Sci. USA* 93: 15233-15238 (1996).

Kronenberg et al., "The PTH/PTHrP Receptor: One Receptor for Two Ligands," in: *Molecular Genetics of Endocrine Disorders* (ed. R.V. Thakker), pp. 389-420 (Chapman & Hall, New York, NY, 1997).

Lanske et al., "PTH/PTHrP Receptor in Early Development and Indian Hedgehog-Regulated Bone Growth," *Science* 273: 663-666 (1996).

Lee et al., "Role of the Extracellular Regions of the Parathyroid Hormone (PTH)/PTH-Related Peptide Receptor in Hormone Binding," *Endocrinology* 135: 1488-1495 (1994).

Lee et al., "Homolog-scanning Mutagenesis of the Parathyroid Hormone (PTH) Receptor Reveals PTH-(1-34) Binding Determinants in the Third Extracellular Loop," *Mol. Endocrinol.* 9: 1269-1278 (1995).

Li et al., "Minimization of a Polypeptide Hormone," *Science* 270: 1657-1660 (1995).

Lin et al., "Expression Cloning of an Adenylate Cyclase-Coupled Calcitonin Receptor," *Science* 254: 1022-1024 (1991).

Livnah et al., "Functional Mimicry of a Protein Hormone by a Peptide Agonist: The EPO Receptor Complex at 2.8 A," *Science* 273: 464-471 (1996).

Majeska et al., "Parathyroid Hormone-Responsive Clonal Cell Lines from Rat Osteosarcoma," *Endocrinology* 107: 1494-1503 (1980).

Mannstadt et al., "Evidence for a Ligand Interaction Site at the Amino-terminus of the Parathyroid Hormone (PTH)/PTH-related Protein Receptor from Cross-Linking and Mutational Studies," *J. Biol. Chem.* 273: 16890-16896 (1998).

Matsumoto et al., "Daily Nasal Spray of hPTH(1-34) for 3 Months Increases Bone Mass in Osteoporotic Subjects: A Pilot Study," *Osteoporos. Int* 17: 1532-1538 (2006).

McCuaig et al., "Molecular Cloning of the Gene Encoding the Mouse Parathyroid Hormone/Parathyroid Hormone-Related Peptide Receptor," *Proc. Natl. Acad. Sci. USA* 91: 5051-5055 (1994).

Menniti et al., "Different Modes of Regulation for Receptors Activating Phospholipase C in the Rat Pancreatoma Cell Line AR4-2J," *Mol. Pharmacal.* 40: 727-733 (1991).

Mickle et al., "Genotype-Phenotype Relationships in Cystic Fibrosis," *Med. Clin. North Am.* 84: 597-607 (2000).

Mikayama et al., "Molecular Cloning and Functional Expression of a cDNA Encoding Glycosylation-Inhibiting Factor," *Proc. Natl. Acad. Sci USA* 90: 10056-10060 (1993).

Mitchell et al., "Mechanisms of Homologous and Heterologous Regulation of Parathyroid Hormone Receptors in the Rat Osteosarcoma Cell Line UMR-106," *Endocrinology* 126: 2650-2660 (1990).

Moretto et al., "(αMe)Nva: Stereoselective Syntheses and Preferred Conformations of Selected Model Peptides," *J. Pept. Res.* 56: 283-297 (2000).

Mullins et al., "Perspective Series: Molecular Medicine in Genetically Engineered Animals," *J. Clin. Invest.* 98: S37-S40 (1996).

Murray et al., "Dexamethasone-Treated ROS 17/2.8 Rat Osteosarcoma Cells are Responsive to Human Carboxylterminal Parathyroid Hormone Peptide hPTH (53-84): Stimulation of Alkaline Phosphatase," *Calcif. Tissue Int.* 49: 120-123 (1991).

Musso et al., "Renal Vasodilatation and Microvessel Adenylate Cyclase Stimulation by Synthetic Parathyroid Hormone-Like Protein Fragments," *Eur. J. Pharmacol.* 174: 139-151 (1989).

Nakamoto et al., "Probing the Bimolecular Interactions of Parathyroid Hormone with the Human Parathyroid Hormone/Parathyroid Hormone-Related Protein Receptor. 1. Design, Synthesis and Characterization of Photoreactive Benzophenone-Containing Analogs of Parathyroid Hormone," *Biochemistry* 34: 10546-10552 (1995).

Nakamura et al., "Action of Fragments of Human Parathyroid Hormone on Blood Pressure in Rats," *Endocrinol. Jpn.* 28: 547-549 (1981).

Neugebauer et al., "Structural Elements of Human Parathyroid Hormone and their Possible Relation to Biological Activities," *Biochemistry* 31: 2056-2063 (1992).

Neugebauer et al., "Solution Structure and Adenylyl Cyclase Stimulating Activities of C-terminal Truncated Human Parathyroid Hormone Analogues," *Biochemistry* 34: 8835-8842 (1995).

Ngo et al., "Chapter 14: Computational Complexity, Protein Structure Prediction, and the Levinthal Paradox," in: *The Protein Folding Problem and Tertiary Structure Prediction* (eds. K.M. Merz et al.), pp. 492-495 (Birkhäuser Verlag, Boston, MA, 1994).

Nielsen et al., "Identification of Prokaryotic and Eukaryotic Signal Peptides and Prediction of their Cleavage Sites," *Prot. Eng.* 10: 1-6 (1997).

Nissenson et al., "Synthetic Peptides Comprising the Amino-Terminal Sequence of a Parathyroid Hormone-Like Protein from Human Malignancies. Binding to Parathyroid Hormone Receptors and Activation of Adenylate Cyclase in Bone Cells and Kidney," *J. Biol. Chem.* 263: 12866-12871 (1988).

Nussbaum et al., "Parathyroid Hormone • Renal Receptor Interactions. Demonstration of Two Receptor-binding Domains," *J. Biol. Chem.* 255: 10183-10187 (1980).

Nutt et al., "Removal of Partial Agonism from Parathyroid Hormone (PTH)-Related Protein-(7-34)NH2 by Substitution of PTH Amino Acids at Positions 10 and 11," *Endocrinology* 127: 491-493 (1990).

Oldenburg et al., "Conformational Studies on Analogs of Recombinant Parathyroid Hormone and their Interactions with Phospholipids," *J. Biol. Chem.* 271: 17582-17591 (1996).

Orkin et al., "Report and Recommendations of the Panel to Assess the NIH Investment in Research on Gene Therapy," available online at http://www.nih.gov/news/panelrep.html, pp. 1-39 (1995).

Orloff et al., "Analysis of PTHRP Binding and Signal Transduction Mechanisms in Benign and Malignant Squamous Cells," *Am. J. Physiol.* 262: E599-E607 (1992).

Orloff et al., "Further Evidence for a Novel Receptor for Amino-Terminal Parathyroid Hormone-Related Protein on Keratinocytes and Squamous Carcinoma Cell Lines," *Endocrinology* 136: 3016-3023 (1995).

Orloff et al., "A Midregion Parathyroid Hormone-Related Peptide Mobilizes Cytosolic Calcium and Stimulates Formation of Inositol Trisphosphate in a Squamous Carcinoma Cell Line," *Endocrinology* 137: 5376-5385 (1996).

Pang et al., "Purification of Unique alpha Subunits of GTP-Binding Regulatory Proteins (G Proteins) by Affinity Chromatography with Immobilized beta gamma Subunits," *J. Biol. Chem.* 265: 18707-18712 (1990).

Parsons et al., "Pharmacology of Parathyroid Hormone and Some of its Fragments and Analogues," in: *Calcium-regulating hormones. Proceedings of the Fifth Parathyroid Conference*, Oxford, United Kingdom, Jul. 21-26, 1974 (eds. R.V. Talmage et al.), pp. 33-39 (Am. Elsevier Pub. Co., New York, NY, 1975).

Peggion et al., "Structure-Function Studies of Analogues of Parathyroid Hormone (PTH)-1-34 Containing Beta-Amino Acid Residues in Positions 11-13," *Biochemistry* 41: 8162-8175 (2002).

Pellegrini et al., "Addressing the Tertiary Structure of Human Parathyroid Hormone-(1-34)," *J. Biol. Chem.* 273: 10420-10427 (1998).

Pettit et al., "The Development of Site-Specific Drug-Delivery Systems for Protein and Peptide Biopharmaceuticals," *Trends Biotechnol.* 16: 343-349 (1998).

Phillips, "The Challenge of Gene Therapy and DNA Delivery," *J. Pharm. Pharmacol.* 53: 1169-1174 (2001).

Pines et al., "Generation and Characterization of Human Kidney Cell Lines Stably Expressing Recombinant Human PTH/PTHrP Receptor: Lack of Interaction with a C-Terminal Human PTH Peptide," *Endocrinology* 135: 1713-1716 (1994).

Pines et al., "Inositol 1-,4-,5-Trisphosphate-Dependent Ca2+ Signaling by the Recombinant Human PTH/PTHrP Receptor Stably Expressed in a Human Kidney Cell Line," *Bone* 18: 381-389 (1996).

Plotkin et al., "Dissociation of Bone Formation from Resorption during 2-week Treatment with Human Parathyroid Hormone-Related Peptide-(1-36) in Humans: Potential as an Anabolic Therapy for Osteoporosis," *J. Clin. Endocrinol. Metab.* 83: 2786-2791 (1998).

Potts et al., "Structure Based Design of Parathyroid Hormone Analogs," *J. Endocrinol.* 154 Suppl: S15-S21 (1997).

Potts et al., "Parathyroid Hormone and Parathyroid Hormone-Related Peptide in Calcium Homeostasis, Bone Metabolism, and Bone Development: The Proteins, Their Genes, and Receptors," in: *Metabolic Bone Disease, 3rd Edition* (eds. L.V. Avioli et al.), pp. 51-94 (Acad. Press, San Diego, CA, 1998).

Ray et al., "NMR Solution Structure of the [Ala26]Parathyroid-Hormone-Related Protein(1-34) Expressed in Humoral Hypercalcemia of Malignancy," *Eur. J. Biochem.* 211: 205-211 (1993).

Reid et al., "Parathyroid Hormone Acutely Elevates Intracellular Calcium in Osteoblastlike Cells," *Am. J. Physiol.* 253: E45-E51 (1987).

Reidhaar-Olson et al., "Active Variants of Human Parathyroid Hormone (1-34) with Multiple Amino Acid Substitutions," *Mol. Cell. Endocrinol.* 160: 135-147 (2000).

Rixon et al., "Parathyroid Hormone Fragments May Stimulate Bone Growth in Ovariectomized Rats by Activating Adenylyl Cyclase," *J. Bone Miner. Res.* 9: 1179-1189 (1994).

Roe et al., "Parathyroid Hormone 1-34 (hPTH 1-34) and Estrogen Produce Dramatic Bone Density Increases in Postmenopausal Osteoporosis. Results from a Placebo-Controlled Randomized Trial," *J. Bone Miner. Res.* 14: S137, Abstract No. 1019 (1999).

Romano et al., "Latest Developments in Gene Transfer Technology: Achievements, Perspectives, and Controversies over Therapeutic Applications," *Stem Cells* 18: 19-39 (2000).

Rosenblatt et al., "Design and Synthesis of Parathyroid Hormone Analogues of Enhanced Biological Activity," *Endocr. Res. Commun.* 4: 115-133 (1977).

Rosenblatt et al., "Identification of a Receptor-binding Region in Parathyroid Hormone," *Endocrinology* 107: 545-550 (1980).

Rosenblatt, "Parathyroid Hormone: Chemistry and Structure-Activity Relations," *Pathobiol. Annu.* 11: 53-86 (1981).

Rosol et al., "Sequences of the cDNAs Encoding Canine Parathyroid Hormone-Related Protein and Parathyroid Hormone," *Gene* 160: 241-243 (1995).

Rubin et al., "Molecular Cloning and Expression of Receptors for Parathyroid Hormone (PTH) and PTH-Related (PTHrP) Protein in Zebrafish," *Am. Zoologist* 36: 97A, Abstract No. 373 (1996).

Rubin et al., "Parathyroid Hormone (PTH)/PTH-Related (PTHRP) Receptor Cloning and in Situ Hybridization in the Zebrafish, Danio Rerio," *Am. Zoologist* 37: 181A, Abstract No. 651 (1997).

Rubin et al., "Molecular Cloning of a Zebrafish cDNA Encoding a Novel Parathyroid Hormone (PTH)/PTH-Related Protein (PTHrP) Receptor (PPR)," *Bone* 23: S255, Abstract No. T224 (1998).

Rubin et al., "Zebrafish Express the Common Parathyroid Hormone/Parathyroid Hormone-Related Peptide Receptor (PTH1R) and a Novel Receptor (PTH3R) that is Preferentially Activated by Mammalian and Fugufish Parathyroid Hormone-Related Peptide," *J. Biol. Chem.* 274: 28185-28190 (1999).

Sacchetti et al., "Green Fluorescent Protein Variants Fold Differentially in Prokaryotic and Eukaryotic Cells," *J. Cell. Biochem. Suppl.* 36: 117-128 (2001).

Sargent et al., "Membrane Lipid Phase as Catalyst for Peptide-Receptor Interactions," *Proc. Natl. Acad. Sci. USA* 83: 5774-5778 (1986).

Schipani et al., "Identical Complementary Deoxyribonucleic Acids Encode a Human Renal and Bone Parathyroid Hormone (PTH)/PTH-Related Peptide Receptor," *Endocrinology* 132: 2157-2165 (1993).

Schipani et al., "Pseudohypoparathyroidism Type Ib is not Caused by Mutations in the Coding Exons of the Human Parathyroid Hormone (PTH)/PTH-Related Peptide Receptor Gene," *J. Clin. Endocrinol. Metab.* 80: 1611-1621 (1995).

Schipani et al., "A Constitutively Active Mutant PTH-PTHrP Receptor in Jansen-Type Metaphyseal Chondrodysplasia," *Science* 268: 98-100 (1995).

Schneider et al., "Cloning and Functional Expression of a Human Parathyroid Hormone Receptor," *Eur. J. Pharmacol.* 246: 149-155 (1993).

Schneider et al., "A C-Terminally Truncated Human Parathyroid Hormone Receptor is Functional and Activates Multiple G Proteins," *FEBS Lett.* 351: 281-285 (1994).

Segre et al., "Characterization of Parathyroid Hormone Receptors in Canine Renal Cortical Plasma Membranes Using a Radioiodinated Sulfur-Free Hormone Analogue. Correlation of Binding with Adenylate Cyclase Activity," *J. Biol. Chem.* 254: 6980-6986 (1979).

Segre et al., "Receptors for Secretin, Calcitonin, Parathyroid Hormone (PTH)/PTH-Related Peptide, Vasoactive Intestinal Peptide, Glucagonlike Peptide 1, Growth Hormone-Releasing Hormone, and Glucagon Belong to a Newly Discovered G-protein-Linked Receptor Family," *Trends Endocrinol. Metab.* 4: 309-314 (1993).

Seuwen et al., "Heparin-Insensitive Calcium Release from Intracellular Stores Triggered by the Recombinant Human Parathyroid Hormone Receptor," *Br. J. Pharmacol.* 114: 1613-1620 (1995).

Shen et al., "Effects of Combined and Separate Intermittent Administration of Low-Dose Human Parathyroid Hormone Fragment (1-34) and 17 Beta-Estradiol on Bone Histomorphometry in Ovariectomized Rats with Established Osteopenia," *Calcif. Tissue Int.* 50: 214-220 (1992).

Shigeno et al., "Parathyroid Hormone Receptors are Plasma Membrane Glycoproteins with Asparagine-Linked Oligosaccharides," *J. Biol. Chem.* 263: 3872-3878 (1988).

Shimada et al., "Purification and Characterization of a Receptor for Human Parathyroid Hormone and Parathyroid Hormone-Related Peptide," *J. Biol. Chem.* 277: 31774-31780 (2002).

Shimizu et al., "Type-Substitution Analysis of the Amino-Terminal Fragment of Parathyroid Hormone, PTH(1-14): An Approach toward New Low Molecular Weight PTH Agonists," *J. Bone Miner. Res.* 14: S289, Abstract No. F398 (1999).

Shimizu et al., "Residue 19 of the Parathyroid Hormone (PTH) Modulates Ligand Interaction with the Juxtamembrane Region of the PTH-1 Receptor," *Biochemistry* 41: 13224-13233 (2002).

Shimizu et al., "Structurally Varied Conformationally Constrained Amino Acids Substitutions at Positions 1 and 3 of PTH(1-14) Preserve or Enhance P1R Binding Affinity and cAMP-signaling Potency," *J. Bone Miner. Res.* 17: S389 (2002).

Shimizu et al., "Novel Parathyroid Hormone (PTH) Antagonists that Bind to the Juxtamembrane Portion of the PTH/PTH-Related Protein Receptor," *J. Biol. Chem.* 280: 1797-1807 (2005).

Shukunami et al., "Chondrogenic Differentiation of Clonal Mouse Embryonic Cell Line ATDC5 In Vitro: Differentiation-dependent Gene Expression of Parathyroid Hormone (PTH)/PTH-related Peptide Receptor," *J. Cell Biol.* 133: 457-468 (1996).

Siegfried et al., "Parathyroid Hormone Stimulates Ecto-5'-Nucleotidase Activity in Renal Epithelial Cells: Role of Protein Kinase-C," *Endocrinology* 136:1267-1275 (1995).

Simon et al., "Diversity of G Proteins in Signal Transduction," *Science* 252: 802-808 (1991).

Skolnick et al., "From Genes to Protein Structure and Function: Novel Applications of Computational Approaches in the Genomic Era," *Trends Biotechnol.* 18: 34-39 (2000).

Smith et al., "The Challenges of Genome Sequence Annotation or "The devil is in the details"," *Nat. Biotechnol.* 15: 1222-1223 (1997).

Strathmann et al., "G Protein Diversity: A Distinct Class of alpha Subunits is Present in Vertebrates and Invertebrates," *Proc. Natl. Acad. Sci. USA* 87: 9113-9117 (1990).

Strojek et al., "The Use of Transgenic Animal Techniques for Livestock Improvement," in: *Genetic Engineering: Principles and Methods*, vol. 10 (eds. J.K. Setlow et al.), pp. 221-246 (Plenum Press, New York, NY, 1988).

Stroop et al., "Chimeric Human Calcitonin and Glucagon Receptors Reveal Two Dissociable Calcitonin Interaction Sites," *Biochemistry* 34: 1050-1057 (1995).

Sunyaev et al., "From Analysis of Protein Structrual Alignments Toward a Novel Approach to Align Protein Sequences," *Proteins* 54: 569-582 (2004).

Suva et al., "A Parathyroid Hormone-Related Protein Implicated in Malignant Hypercalcemia: Cloning and Expression," *Science* 237: 893-896 (1987).

Szabo, "In Situ Hybridization," in: *Human Chromosomes: Manual of Basic Techniques* (eds. R.S. Verma et al.), pp. 152-165 (Pergamon Press, New York, NY,1989).

Takasu et al., "The 69-84 Amino Acid Region of the Parathyroid Hormone Molecule is Essential for the Interaction of the Hormone with the Binding Sites with Carboxyl-terminal Specificity," *Endocrinology* 137: 5537-5543 (1996).

Takasu et al., "Human PTH/PTHrP Receptors and Type-2 PTH Receptors Show Discordant Selectivity for Human PTH Analogs with Amino-Terminal Modifications," *Bone* 23:S255, Abstract No. T223 (1998).

Takasu et al., "Phospholipase C Activation via the Human PTH/PTHrP Receptor Requires an Intact Amino-Terminus of Human PTH," *Bone* 23: S447, Abstract No. F148 (1998).

Takasu et al., "Type-1 Parathyroid Hormone (PTH)/PTH-Related Peptide (PTHrP) Receptors Activate Phospholipase C in Response to Carboxyl-truncated Analogs of PTH(1-34)," *Endocrinology* 139: 4293-4299 (1998).

Takasu et al., "Dual Signaling and Ligand Selectivity of the Human PTH/PTHrP Receptor," *J. Bone Miner. Res.* 14: 11-20 (1999).

Tamura et al., "Parathyroid Hormone 1-34, but not 3-34 or 7-34, Transiently Translocates Protein Kinase C in Cultured Renal (OK) Cells," *Biochem. Biophys. Res. Commun.* 159: 1352-1358 (1989).

Tan et al., "Peptide Agonist Docking in the N-Terminal Ectodomain of a Class II G Protein-Coupled Receptor, the VPAC1 Receptor. Photoaffinity, NMR, and Molecular Modeling," *J. Biol. Chem.* 281: 12792-12798 (2006).

Treanor et al., "Characterization of a Multicomponent Receptor for GDNF," *Nature* 382: 80-83 (1996).

Tregear et al., "Synthetic Analogues of Residues 1-34 of Human Parathyroid Hormone: Influence of Residue No. 1 on Biological Potency in Vitro," *Endocr. Res. Commun.* 2: 561-570 (1975).

Tsomaia et al., "Cooperative Interaction of Arginine-19 and the N-Terminal Signaling Domain in the Affinity and Potency of Parathyroid Hormone," *Biochemistry* 43: 3459-3470 (2004).

Tsomaia et al., "Toward Parathyroid Hormone Minimization: Conformational Studies of Cyclic PTH(1-14) Analogues," *Biochemistry* 43: 690-699 (2004).

Turner et al., "A Putative Selectivity Filter in the G-Protein-Coupled Receptors for Parathyroid Hormone and Secretin," *J. Biol. Chem.* 271: 9205-9208 (1996).

Turner et al., "Single Mutations Allow the PTH2 Receptor to Respond to PTHrP," *J. Bone Miner. Res.* 12: S133, Abstract No. 121 (1997).

Turner et al., "Transmembrane Residues Together with the Amino Terminus Limit the Response of the Parathyroid Hormone (PTH) 2 Receptor to PTH-Related Peptide," *J. Biol. Chem.* 273: 3830-3837 (1998).

Ullrich et al., "Signal Transduction by Receptors with Tyrosine Kinase Activity," *Cell* 61: 203-212 (1990).

Unson et al., "Characterization of Deletion and Truncation Mutants of the Rat Glucagon Receptor. Seven Transmembrane Segments are Necessary for Receptor Transport to the Plasma Membrane and Glucagon Binding," *J. Biol. Chem.* 270: 27720-27727 (1995).

Ureña et al., "Regulation of Parathyroid Hormone (PTH)/PTH-Related Peptide Receptor Messenger Ribonucleic Acid by Glucocorticoids and PTH in ROS 17/2.8 and OK Cells," *Endocrinology* 134: 451-456 (1994).

Usdin et al., "Identification and Functional Expression of a Receptor Selectively Recognizing Parathyroid Hormone, the PTH2 Receptor," *J. Biol. Chem.* 270: 15455-15458 (1995).

Verma et al., "Gene Therapy- Promises, Problems and Prospects," *Nature* 389: 239-242 (1997).

Voet et al., "3. Chemical Evolution," in: *Biochemistry* (eds. D. Voet et al.), pp. 126-128 and 228-234 (Wiley, New York, NY, 1990).

Vogt et al., "An Assessment of Amino Acid Exchange Matrices in Aligning Protein Sequences: The Twilight Zone Revisited," *J. Mol. Biol.* 249: 816-831 (1995).

Wall, "Transgenic Livestock: Progress and Prospects for the Future," *Theriogenology* 45: 57-68 (1996).

Wang et al., "Rapid Analysis of Gene Expression (RAGE) Facilitates Universal Expression Profiling," *Nucleic Acids Res.* 27: 4609-4618 (1999).

Wells, "Additivity of Mutational Effects in Proteins," *Biochemistry* 29: 8509-8517 (1990).

Wells, "Hormone Mimicry," *Science* 273: 449-450 (1996).

Whitfield et al., "Restoration of Severely Depleted Femoral Trabecular Bone in Ovariectomized Rats by Parathyroid Hormone-(1-34)," *Calcif. Tissue Int.* 56: 227-231 (1995).

Whitfield et al., "Small Bone-Building Fragments of Parathyroid Hormone: New Therapeutic Agents for Osteoporosis," *Trends Pharmacol. Sci.* 16: 382-386 (1995).

Whitfield et al., "Stimulation of the Growth of Femoral Trabecular Bone in Ovariectomized Rats by the Novel Parathyroid Hormone Fragment, hPTH-(1-31)NH2 (Ostabolin)," *Calcif. Tissue Int.* 58: 81-87 (1996).

Whitfield et al., "Comparison of the Ability of Recombinant Human Parathyroid Hormone, rhPTH-(1-84), and hPTH-(1-31)NH2 to Stimulate Femoral Trabecular Bone Growth in Ovariectomized Rats," *Calcif. Tissue Int.* 60: 26-29 (1997).

Wigley et al., "Site-Specific Transgene Insertion: An Approach," *Reprod. Fertil. Dev.* 6: 585-588 (1994).

Wittelsberger et al., "The Mid-Region of Parathyroid Hormone (1-34) Serves as a Functional Docking Domain in Receptor Activation," *Biochemistry* 45: 2027-2034 (2006).

Wrighton et al., "Small Peptides as Potent Mimetics of the Protein Hormone Erythropoietin," *Science* 273: 458-463 (1996).

Wu et al., "Structural and Physiologic Characterization of the Midregion Secretory Species of Parathyroid Hormone-Related Protein," *J. Biol. Chem.* 271: 24371-24381 (1996).

Yamaguchi et al., "Parathyroid Hormone-Activated Calcium Channels in an Osteoblast-Like Clonal Osteosarcoma Cell Line: cAMP-Dependent and cAMP-Independent Calcium Channels," *J. Biol. Chem.* 262: 7711-7718 (1987).

Yamamoto et al., "Characterization and Agonist-Induced Down-Regulation of Parathyroid Hormone Receptors in Clonal Rat Osteosarcoma Cells," *Endocrinology* 122:1208-1217 (1988).

Yamamoto et al., "Parathyroid Hormone-Related Peptide-(1-34) [PTHrP-(1-34)] Induces Vasopressin Release from the Rat Supraoptic Nucleus In Vitro Through a Novel Receptor Distinct from a Type I or Type II PTH/PTHrP Receptor," *Endocrinology* 138: 2066-2072 (1997).

Yamamoto et al., "Centrally Administered Parathyroid Hormone (PTH)-Related Protein(1-34) but not PTH(1-34) Stimulates Arginine-Vasopressin Secretion and its Messenger Ribonucleic Acid Expression in Supraoptic Nucleus of the Conscious Rats," *Endocrinology* 139: 383-388 (1998). (Printed with erroneous vol. No. 138).

Yan et al., "Two-Amino Acid Molecular Switch in an Epithelial Morphogen that Regulates Binding to Two Distinct Receptors," *Science* 290: 523-527 (2000).

Zhou et al., "Direct Mapping of an Agonist-Binding Domain within the Parathyroid Hormone/Parathyroid Hormone-Related Protein Receptor by Photoaffinity Crosslinking," *Proc. Natl. Acad. Sci. USA* 94: 3644-3649 (1997).

International Search Report for PCT/US04/22830 (mailed Mar. 18, 2005).

Gensure et al., "Identification of Determinants of Inverse Agonism in a Constitutively Active Parathyroid Hormone/Parathyroid Hormone-Related Peptide Receptor by Photoaffinity Cross-Linking and Mutational Analysis," *J. Biol. Chem.* 276:42692-42699 (2001).

English Translation of "Notice of Reasons for Rejection" for Japanese Application No. 2006-520353 (issued May 24, 2010) (pp. 1-13).

* cited by examiner

| SEQ ID NO. | Peptide | Sequences |
|---|---|---|
| | PTH(1-14) peptides | |
| 26 | PTH(1-14)NH₂ (native, rat) | Ala-Val-Ser-Glu-Ile-Gln-Leu-Met-His-Asn-Leu-Gly-Lys-His-NH₂ |
| 27 | [Ala$^{3,12}$,Gln$^{10}$,Har$^{11}$,Trp$^{14}$]PTH(1-14)NH₂ | Ala-Val-Ala-Glu-Ile-Gln-Leu-Met-His-Gln-Har-Ala-Lys-Trp-NH₂ |
| 14 | [Ac₅c$^1$,Aib$^3$,Gln$^{10}$,Har$^{11}$,Ala$^{12}$,Trp$^{14}$]PTH(1-14)NH₂ | Ac₅c-Val-Aib-Glu-Ile-Gln-Leu-Met-His-Gln-Har-Ala-Lys-Trp-NH₂ |
| 15 | [desNH2-Ac₅c$^1$,Aib$^3$,Gln$^{10}$,Har$^{11}$,Ala$^{12}$,Trp$^{14}$]PTH(1-14)NH₂ | (desNH2)Ac₅c-Val-Aib-Glu-Ile-Gln-Leu-Met-His-Gln-Har-Ala-Lys-Trp-NH₂ |
| 16 | [desNH2-Aib$^1$,Aib$^3$,Gln$^{10}$,Har$^{11}$,Ala$^{12}$,Trp$^{14}$]PTH(1-14)NH₂ | (desNH2)Aib-Val-Aib-Glu-Ile-Gln-Leu-Met-His-Gln-Har-Ala-Lys-Trp-NH₂ |
| 17 | [Ac₅c$^1$,Trp$^2$,Aib$^3$,Gln$^{10}$,Har$^{11}$,Ala$^{12}$,Trp$^{14}$]PTH(1-14)NH₂ | Ac₅c-Trp-Aib-Glu-Ile-Gln-Leu-Met-His-Gln-Har-Ala-Lys-Trp-NH₂ |
| 18 | [Ac₅c$^1$,Bpa$^2$,Aib$^3$,Gln$^{10}$,Har$^{11}$,Ala$^{12}$,Trp$^{14}$]PTH(1-14)NH₂ | Ac₅c-Bpa-Aib-Glu-Ile-Gln-Leu-Met-His-Gln-Har-Ala-Lys-Trp-NH₂ |
| 19 | [Ac₅c$^1$,Arg$^2$,Aib$^3$,Gln$^{10}$,Har$^{11}$,Ala$^{12}$,Trp$^{14}$]PTH(1-14)NH₂ | Ac₅c-Arg-Aib-Glu-Ile-Gln-Leu-Met-His-Gln-Har-Ala-Lys-Trp-NH₂ |
| 20 | [Deg$^{1,3}$,Gln$^{10}$,Har$^{11}$,Ala$^{12}$,Trp$^{14}$]PTH(1-14)NH₂ | Deg-Val-Deg-Glu-Ile-Gln-Leu-Met-His-Gln-Har-Ala-Lys-Trp-NH₂ |
| 21 | [Deg$^{1,3}$,Trp$^2$,Gln$^{10}$,Har$^{11}$,Ala$^{12}$,Trp$^{14}$]PTH(1-14)NH₂ | Deg-Trp-Deg-Glu-Ile-Gln-Leu-Met-His-Gln-Har-Ala-Lys-Trp-NH₂ |
| 22 | [Deg$^{1,3}$,Bpa$^2$,Gln$^{10}$,Har$^{11}$,Ala$^{12}$,Trp$^{14}$]PTH(1-14)NH₂ | Deg-Bpa-Deg-Glu-Ile-Gln-Leu-Met-His-Gln-Har-Ala-Lys-Trp-NH₂ |
| 23 | [Ac₅c$^1$,Trp$^2$,Aib$^3$,Nle$^8$,Gln$^{10}$,Har$^{11}$,Ala$^{12}$,Tyr$^{14}$]PTH(1-14)NH₂ | Ac₅c-Trp-Aib-Glu-Ile-Gln-Leu-Nle-His-Gln-Har-Ala-Lys-Tyr-NH₂ |
| 24 | [Ac₅c$^1$,Bpa$^2$,Aib$^3$,Nle$^8$,Gln$^{10}$,Har$^{11}$,Ala$^{12}$,Tyr$^{14}$]PTH(1-14)NH₂ | Ac₅c-Bpa-Aib-Glu-Ile-Gln-Leu-Nle-His-Gln-Har-Ala-Lys-Tyr-NH₂ |
| 25 | [Deg$^{1,3}$,Bpa$^2$,Nle$^8$,Gln$^{10}$,Har$^{11}$,Ala$^{12}$,Trp$^{14}$,Arg$^{19}$,Tyr$^{21}$]PTH(1-21)NH₂ | Deg-Bpa-Deg-Glu-Ile-Gln-Leu-Nle-His-Gln-Har-Ala-Lys-Trp-Leu-Ala-Ser-Val-Arg-Arg-Tyr*-NH₂ |
| | N-truncated peptides | |
| 28 | [Aib$^3$,Nle$^8$,Gln$^{10}$,Har$^{11}$,Ala$^{12}$,Trp$^{14}$,Arg$^{19}$,Tyr$^{21}$]PTH(3-21)NH₂ | Aib-Glu-Ile-Gln-Leu-Nle-His-Gln-Har-Ala-Lys-Trp-Leu-Ala-Ser-Val-Arg-Arg-Tyr-NH₂ |
| 29 | [Ile$^5$,Trp$^{23}$,Tyr$^{36}$]PTHrP(5-36)NH₂ | Ile-Gln-Leu-Leu-His-Asp-Lys-Gly-Lys-Ser-Ile-Gln-Asp-Leu-Arg-Arg-Arg-Phe-Phe-Leu-His-His-Leu-Ile-Ala-Glu-Ile-His-Thr-Ala-Glu-Tyr*-NH₂ |
| 31 | [Ile$^5$,Leu$^{11}$,D-Trp$^{12}$,Trp$^{23}$,Tyr$^{36}$]PTHrP(5-36)NH₂ | Ile-Gln-Leu-Leu-His-Asp-Leu-DTrp-Lys-Ser-Ile-Gln-Asp-Leu-Arg-Arg-Arg-Phe-Phe-Leu-His-His-Leu-Ile-Ala-Glu-Ile-His-Thr-Ala-Glu-Tyr-NH₂ |
| | $^{125}$I-PTH tracer radioligand | |
| 32 | [Aib$^{1,3}$,Nle$^8$,Gln$^{10}$,Har$^{11}$,Ala$^{12}$,Trp$^{14}$,Tyr$^{15}$]PTH(1-15)NH₂ | Aib-Val-Aib-Glu-Ile-Gln-Leu-Nle-His-Gln-Har-Ala-Lys-Trp-Tyr*-NH₂ |

Figure 1

| Peptides | | IC$_{50}$ | |
|---|---|---|---|
| PTH(1-14) peptides | | nM | n |
| parent | | 30 ± 7 | 3 |
| desNH$_2$-Aib$^1$ | | 4,500 ± 700 | 4 |
| desNH$_2$-AC$_5$C$^1$ | | 1,800 ± 100 | 4 |
| Arg$^2$ | | 25,000 ± 2,000 | 4 |
| Trp$^2$ | | 770 ± 110 | 4 |
| Bpa$^2$ | | 1,400 ± 200 | 4 |
| Deg$^{1,3}$ | | 230 ± 50 | 3 |
| Deg$^{1,3}$,Trp$^2$ | | 2,700 ± 300 | 3 |
| Deg$^{1,3}$,Bpa$^2$ | | 840 ± 110 | 3 |
| | | | |
| Other peptides | | | |
| rPTH(1-34) | | 4.8 ± 0.8 | 3 |
| PTHrP(5-36) | | 5.5 ± 1.0 | 3 |
| [Aib3,M]PTH(3-21) | | 750 ± 90 | 3 |
| [Aib1,3,M]PTH(1-21) | | 18 ± 4 | 3 |

Figure 2

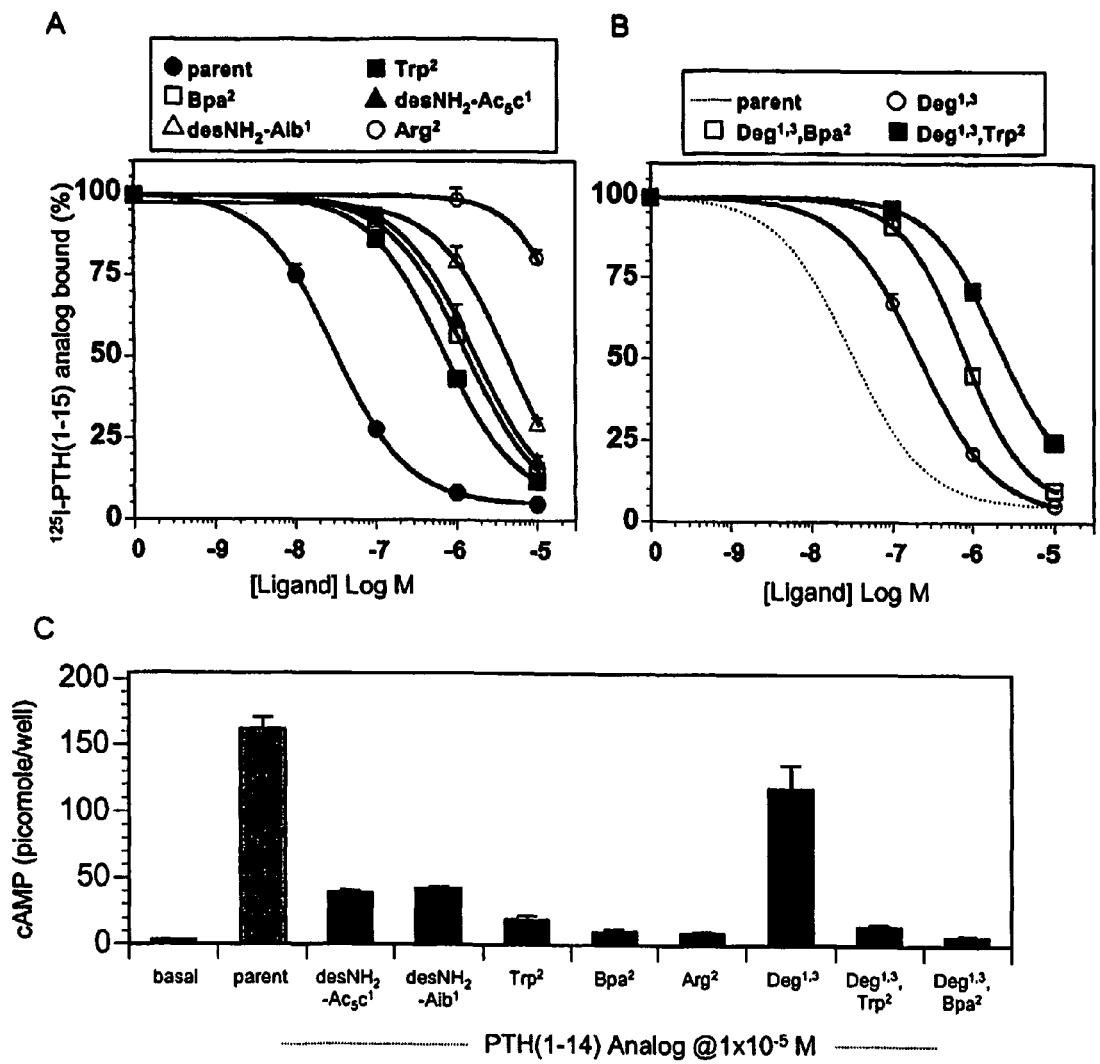

Figure 3

Functional Responses in HKRK-B28 Cells. Binding (A and B) and cAMP agonism/partial agonism assays (C) were performed in HKRK-B28 cells. The parent peptide was [AC5C1,Aib3,Gln10,Har11,Ala12,Trp14]PTH(1-14)NH2 and derivatives thereof were substituted at positions 1, 2 and/or 3, as indicated. Binding assays (4h @ 15°C) were performed with $^{125}$I-[Aib1,3,Nle8,Gln10,Har11,Ala12,Trp14,Tyr15]PTH(1-15)NH2 tracer. cAMP assays were performed at RT for 30 min. Relative to the parent, the substituted analogs lack appreciable agonist activity.

Figure 4

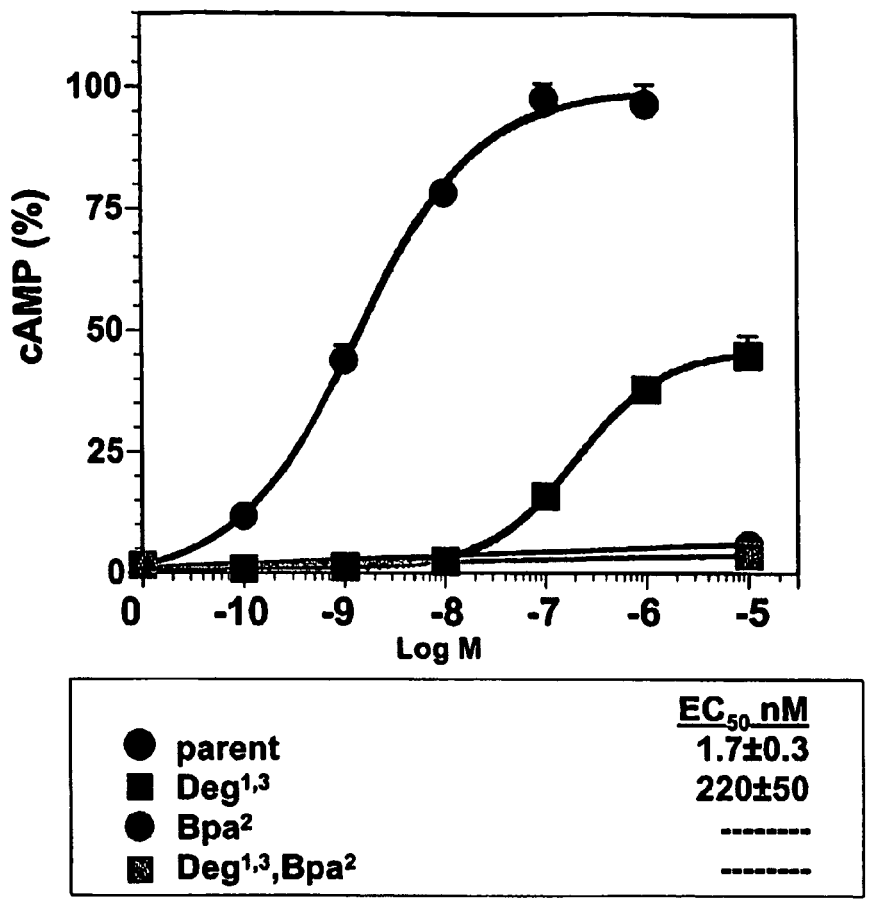

cAMP Responses in HKRK-B28 Cells. The parent peptide, [AC5C1,Aib3,Gln10,Har11,Ala12,Trp14]PTH(1-14)NH2, and derivatives thereof substituted at positions 1, 2 and/or 3, as indicated, were assayed for cAMP agonist responses in HKRK-B28 cells. The parent peptide functions as a fully potent and efficacious agonist, the Deg1,3-substituted analog is a partial agonist, and the Bpa2-substituted analogs lack agonist activity.

Figure 5

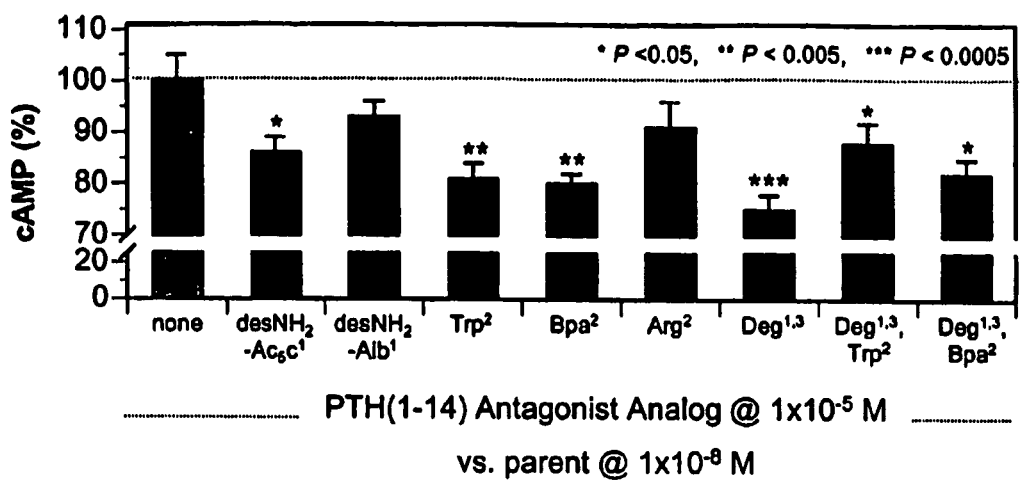

Antagonism Assays In HK-RK-B28 Cells. cAMP antagonism assays were performed in HKRK-B28 cells. Cells were treated with the J domain-selective agonist, [AC5C1,Aib3,Gln10,Har11,Ala12,Trp14]PTH(1-14)NH2 (parent) at 10 nM, either alone (none) or with a candidate antagonist peptide (10 μM), which was a derivative of the parent PTH(1-14) peptide substituted at positions 1, 2 and/or 3, as indicated. Asterisks indicate significant reductions in cAMP levels, as compared to cells not treated with antagonist (none).

Figure 6

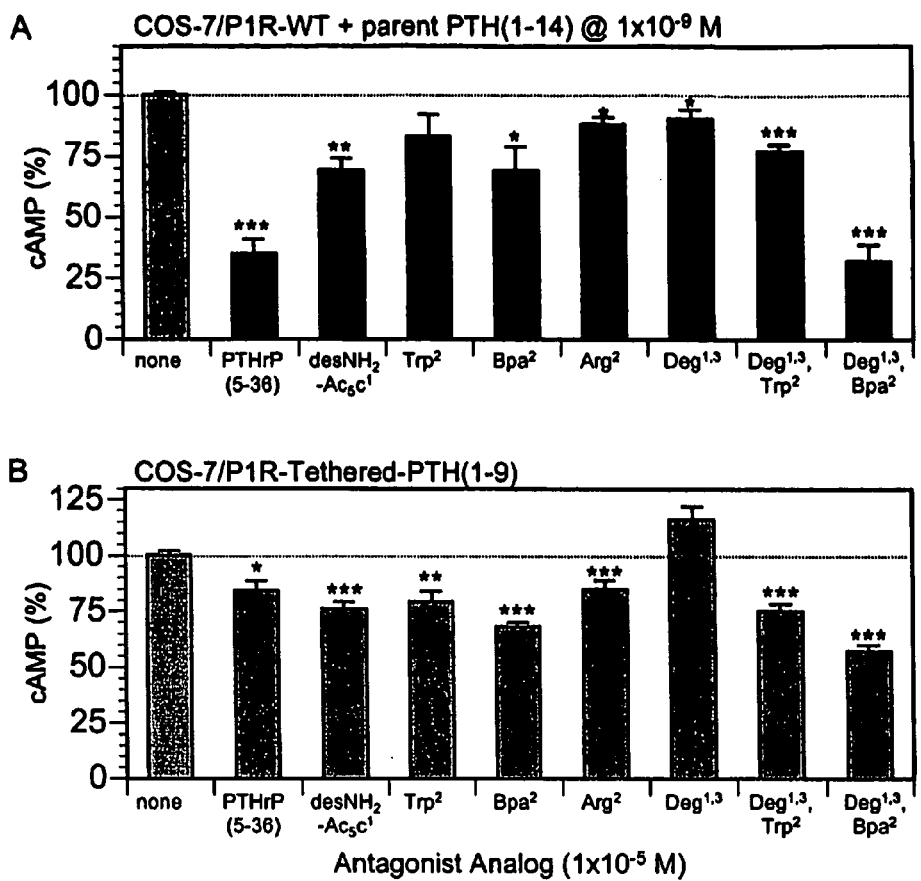

$* P < 0.05,  P < 0.005, * P < 0.0005$

Antagonism Assays in COS-7 Cells. cAMP antagonism assays were performed in COS-7 cells transfect with the wild-type P1R (A), or a constitutively active P1R derivative having the first 9 residues of PTH tethered to TM1 of the P1R and in place of the P1R N-terminal domain (inset), B). In A, cells were treated with the J domain-selective agonist, [AC5C1,Aib3,Gln10,Har11,Ala12,Trp14]PTH(1-14)NH2 (parent) at 1 nM, alone (none) or with a candidate antagonist peptide (10 μM), which was a derivative of the parent PTH(1-14) peptide substituted at positions 1, 2 and/or 3, as indicated, or [I5,W23,Y36]PTHrP(5-36) analog. Asterisks indicate significant reductions in cAMP levels, as compared to cells not treated with antagonist (none).

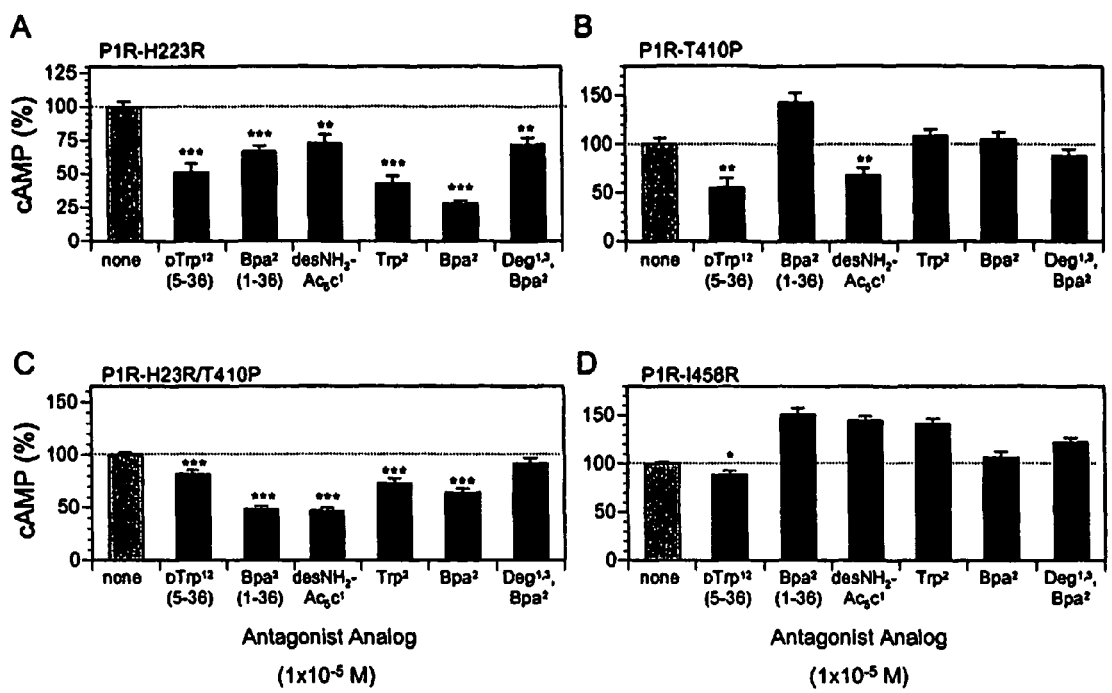

Figure 7

Inverse Agonist Responses in COS-7 Cells. COS-7 cells were transfect with the constitutively active P1Rs: P1R-H223R (A), P1R-T410P (B), P1R-H223R/T410P (C), or P1R-I458R (D) and then were incubated (30 min@R.T.) either in the absence of peptide (none) or in the presence of the indicated antagonist/inverse agonist peptide (10 μM), and cAMP was measured by RIA. Asterisks indicate significant reductions in cAMP levels, compared to untreated cells (none).

Figure 8

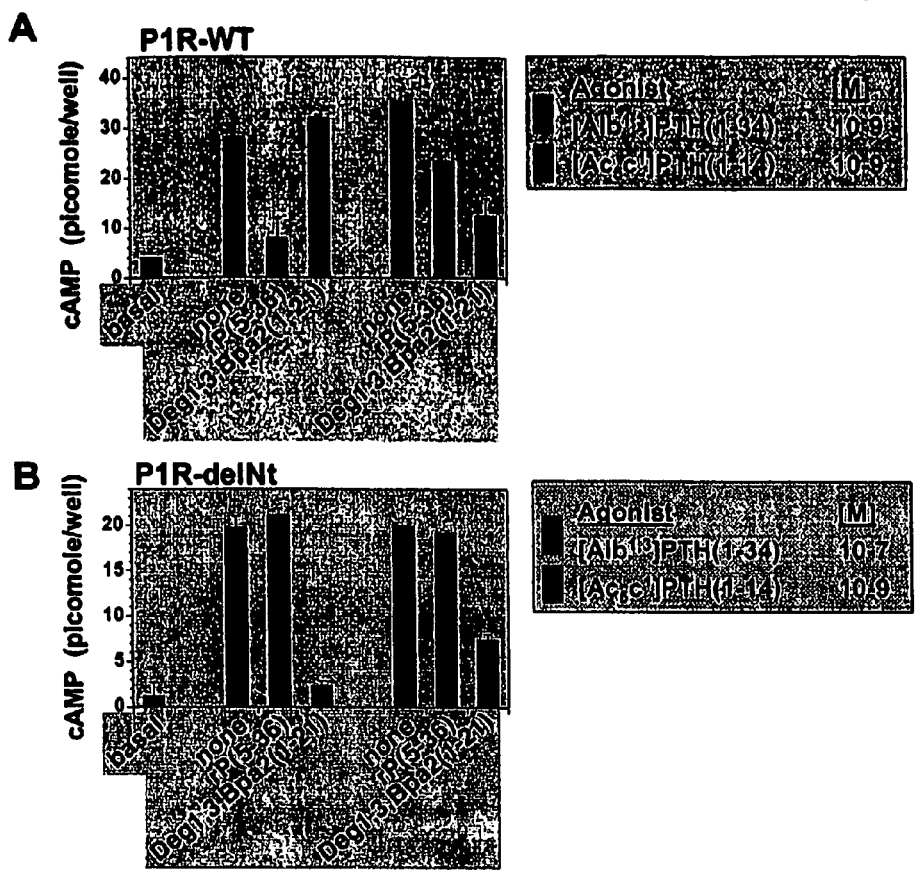

"N" versus "J" Domain selectivity of P1R Antagonists in COS-7 Cells. cAMP antagonism assays were performed in COS-7 cells transfect with the wild-type P1R (A), or a P1R derivative (P1R-delNt) having most (residues 24-181) of the P1R N domain deleted (B). Cells were treated with the agonist [Aib1,3,Tyr34]hPTH(1-34)NH2 ([Aib1,3]PTH(1-34)), which utilizes both N and J domains for affinity/potency, or with [AC5C1,Aib3,Gln10,Har11,Ala12,Trp14]PTH(1-14)NH2 ([Ac5c1]PTH(1-14)), which uses only the J domain for affinity/potency, at the concentrations indicated in the key, so as to elicit half-maximum cAMP responses in the absence of antagonist (none). The analogs PTHrP(5-36) and Deg1,3,Bpa2-PTH(1-21) were added at 1x10-5 M, as indicated. On the WT receptor, PTHrP(5-36) antagonizes PTH(1-34) analog more effectively than does Deg1,3,Bpa2-PTH(1-21), but the PTH(1-21) analog antagonizes PTH(1-14), more effectively than does PTHrP(5-36). On P1R-delNt, Deg1,3,Bpa2-PTH(1-21) antagonizes either agonist, whereas PTHrP(5-36) lacks antagonist capability. Thus, PTHrP(5-36) is an N domain-selective antagonist, whereas Deg1,3,Bpa2-PTH(1-21) is a J domain-selective antagonist. The analog Deg1,3,Bpa2-PTH(1-14) behaved similarly in these assays to Deg1,3,Bpa2-PTH(1-21).

|  | IC$_{50}$(nM) |
|---|---|
| ● PTH(1-34) | 2 |
| ● PTHrP(5-36) | 50 |
| ▨ [Deg$^{1,3}$,Bpa$^2$,Y$^{15}$,M]PTH(1-21) | 150 |

Competition Binding Assays in HKRK-B7 Cells. Binding assays were performed in HKRK-B7 cells, which express the wild-type hP1R, using $^{125}$I-[Aib1,3,Nle8,Gln10,Har11,Ala12,Trp14,Tyr15]PTH(1-15)NH2 as a tracer radioligand and the indicated unlabeled peptides as competitors. PTH(1-34) is [Tyr34]hPTH(1-34)NH2.

Figure 10

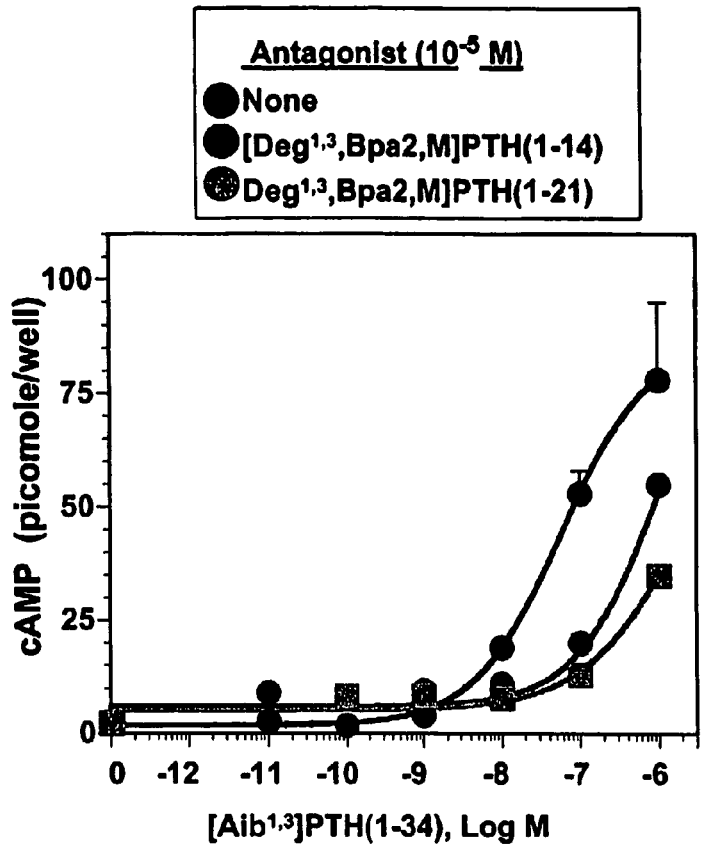

Competitive Antagonism on P1R-delNt. COS-7 cells transfected with P1R-delNt wer_ stimulated with varying concentrations of the agonist [Aib1,3,Tyr34]hPTH(1-34)NH2 ([Aib1,3]PTH(1-34)), either in the absence of antagonist (green circles) or in the presence of an antagonist, [Deg1,3,Bpa2,M]PTH(1-14) (red circles) or [Deg1,3,Bpa2,M]PTH(1-21) (yellow squares) each at 1x10-5 M, as indicated in the figure key. Each antagonist causes a parallel, right-ward shift in the agonist dose-response curve , which is consistent with a competitive mechanism of inhibition.

Figure 11

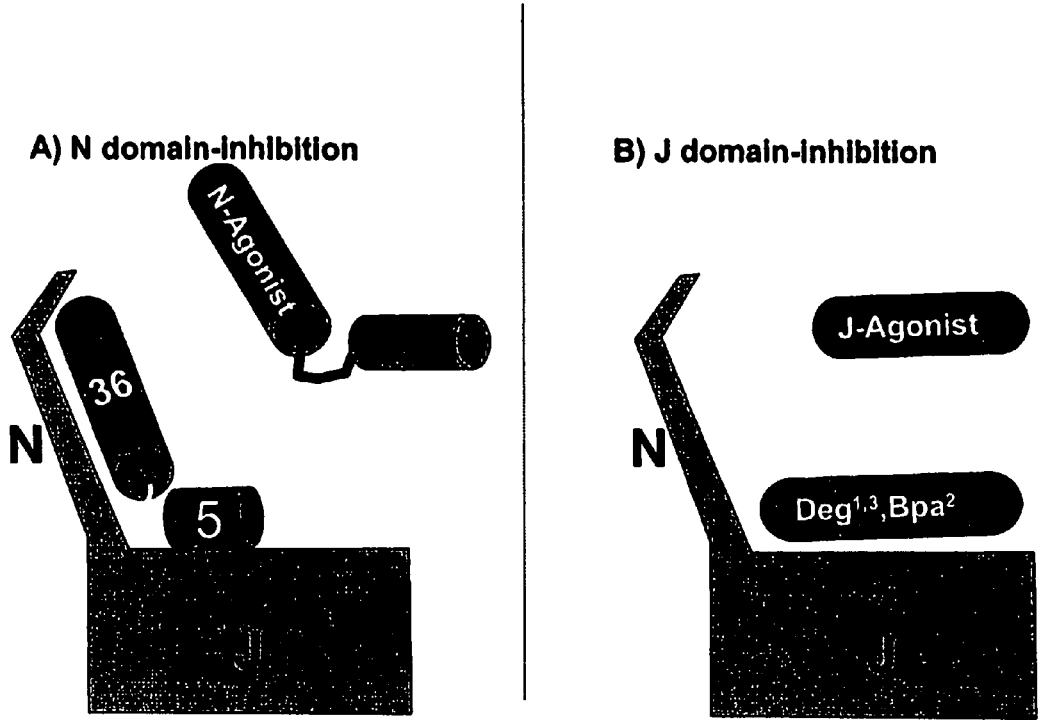

A) N domain-inhibition

B) J domain-inhibition

Two Modes of Competitive Inhibition at the P1R. Two modes of antagonism are now recognized at the P1R. N domain inhibition (A) is utilized by most conventional P1R antagonists, such as PTHrP(5-36) and PTHrP(7-34) analogs, and is based on the derivation of binding energy primarily from interactions between the (21-34) region of the ligand and the P1R N domain. This mechanism is effective for of inhibition of N-domain-dependent agonists, such as PTH(1-34), but not for N domain-independent agonists, such as PTH(1-14). J domain inhibition (B) is utilized by the novel analogs described herein, and is based on the derivation of binding energy primarily or wholly from interactions between the (1-20) region of the ligand and the J domain of the P1R. This mechanism is effective for inhibition of J-domain-dependent agonists, such as PTH(1-14) analogs, but not for N domain-dependent agonists, such as PTH(1-34). A J domain-selective antagonists would be useful for characterizing small-molecules that act as PTH mimetics, since such molecules are likely to bind to the J domain.

CONFORMATIONALLY CONSTRAINED PARTHYROID HORMONE (PTH) ANALOGS

CROSS-REFERENCE TO RELATED APPLICATIONS

This application is a national phase of International Appl. No. PCT/US2004/022830 filed Jul. 16, 2004 which published under PCT Article 21(2) in English, said PCT/US2004/022830 claims the benefit of U.S. Provisional Application No. 60/487,589 filed Jul. 17, 2003 both of which are herein incorporated by reference.

STATEMENT REGARDING FEDERALLY-SPONSORED RESEARCH AND DEVELOPMENT

Statement under MPEP 310. The U.S. Government has a paid-up license in this invention and the right in limited circumstances to require the patent owner to license others on reasonable terms as provided for by the terms of Grant No. DK-11794 awarded by the National Institutes of Health.

Part of the work performed during development of this invention utilized U.S. Government funds. The U.S. Government has certain rights in this invention.

BACKGROUND OF THE INVENTION

1. Field of the Invention

The present invention relates to conformationally constrained parathyroid hormone (PTH) and parathyroid hormone related protein (PTHrP) analogs, and methods of preparing and using these analogs.

2. Background Art

Parathyroid hormone

Parathyroid hormone (PTH), an 84 amino acid peptide, is the principal regulator of ionized blood calcium in the human body (Kronenberg, H. M., et aL, In *Handbook of Experimental Pharmacology*, Mundy, G. R., and Martin, T. J., (eds), pp. 185-201, Springer-Verlag, Heidelberg (1993)). Regulation of calcium concentration is necessary for the normal function of the gastrointestinal, skeletal, neurologic, neuromuscular, and cardiovascular systems. PTH synthesis and release are controlled principally by the serum calcium level; a low level stimulates and a high level suppresses both hormone synthesis and release. PTH, in turn, maintains the serum calcium level by directly or indirectly promoting calcium entry into the blood at three sites of calcium exchange: gut, bone, and kidney. PTH contributes to net gastrointestinal absorption of calcium by favoring the renal synthesis of the active form of vitamin D. PTH promotes calcium resorption from bone indirectly by stimulating differentiation of the bone-resorbing cells, osteoclasts. It also mediates at least three main effects on the kidney: stimulation of tubular calcium reabsorption, enhancement of phosphate clearance, and promotion of an increase in the enzyme that completes synthesis of the active form of vitamin D. PTH is thought to exert these effects primarily through receptor-mediated activation of adenylate cyclase and/or phospholipase C.

Disruption of calcium homeostasis may produce many clinical disorders (e.g., severe bone disease, anemia, renal impairment, ulcers, myopathy, and neuropathy) and usually results from conditions that produce an alteration in the level of parathyroid hormone. Hypercalcemia is a condition that is characterized by an elevation in the serum calcium level. It is often associated with primary hyperparathyroidism in which an excess of PTH production occurs as a result of a parathyroid gland lesion (e.g., adenoma, hyperplasia, or carcinoma). Another type of hypercalcema, humoral hypercalcemia of malignancy (HHM), is the most common paraneoplastic syndrome. It appears to result in most instances from the production by tumors (e.g., squamous, renal, ovarian, or bladder carcinomas) of a class of protein hormone which shares amino acid homology with PTH. These PTH-related proteins (PTHrP) appear to mimic certain of the renal and skeletal actions of PTH and are believed to interact with the PTH receptor in these tissues.

PTH Derivatives

PTH derivatives include polypeptides that have amino acid substitutions or are truncated relative to the full length molecule. A 14, a 21 and a 34 amino acid amino-terminal truncated form of PTH, as well as a C-terminal truncated form have been studied. Additionally, amino acid substitutions within the truncated polypeptides have also been investigated.

Synthetic PTH(1-34) exhibits full bioactivity in most cell-based assay systems, has potent anabolic effects on bone mass in animals and has recently been shown to reduce the risk of bone fracture in postmenopausal osteoporotic women (Neer, R. M., et al., N. E. J. M. 344:1434-1441 (2001); Dempster, D. W., et al., *Endocr Rev* 14:690-709 (1993)). PTH acts on the PTH/PTHrP receptor (P1R), a class II G protein-coupled heptahelical receptor that couples to the adenylyl cyclase/cAMP and phospolipase C/inositol phosphate (IP) signaling pathway (Rippner, H., et al., *Science* 254:1024-1026 (1991)). Deletion analysis studies have shown that the amino-terminal residues of PTH play a crucial role in stimulating the P1R to activate the cAMP and IP signaling pathways (Tregear, G. W., et al., *Endocrinology* 93:1349-1353 (1973); Takasu, H., et al., *Biochemistry* 38:13453-13460 (1999)). Crosslinking and receptor mutagenesis studies have indicated that residues in the amino-terminal portion of PTH interact with the extracellular loops and extracellular ends of the seven transmembrane helices, which reside within the juxtamembrane region of the receptor (Bergwitz, C., et al., *J. Biol. Chem.* 271:26469-26472 (1996); Hoare, S. R. J., et al., *J. Biol. Chem* 276:7741-7753 (2001); Behar, V., et al., *J. Biol. Chem.* 275:9-17 (1999); Shimizu, M., et al., *J. Biol. Chem.* 275:19456-19460 (2000); Luck, M. D., et al., *Molecular Endocrinology* 13:670-680 (1999)).

Most current P1R antagonists are N-terminally truncated analogs of PTH(1-34) or PTHrP (1-36) (e.g. PTHrP(5-36)). These antagonists recognize the receptor's amino-terminal extracellular ("N") domain with high binding affinity. However, the N-terminal truncation results in the inability of the PTH or PTHrP peptide to signal through the receptor, thereby acting as an antagonist.

α-Helix Stabilizers

The first 34 amino acids of PTH and PTHrP contain sufficient information for high affinity P1R binding and potent induction of P1R-mediated signaling responses (Neer, R M, et al., *N.E.J.M.* 344: 1434-1441(2001)). Short N-terminal fragments of PTH, such as PTH(1-14) and PTH(1-11) exhibit extremely weak binding affinities (Kd>>100 µM) but are nonetheless capable of eliciting cAMP-signaling responses, albeit with potencies (EC50s≧100 µM) that are substantially weaker than that of PTH(1-34)(EC50-2 nM)(Luck, M D et al., *Molecular Endocrinology* 13: 670-680(1999)). Recently, it has been discovered that a series of modified PTH(1-14) and PTH(1-11) analogs exhibit signaling potencies that are nearly, or even fully, equal to that of PTH(1-34)(Shimizu, M et al., *Endocrinology* 142: 3068-3074(2001); Shimizu, M. et al., *J. Biol. Chem.* 276: 490003-49012(2001); Shimizu, M. et al., *J. Biol. Chem.* 275: 21836-21843(2000)). One such type of a modifier is a lactam bridge, which is a side chain-to-side chain amide bridge formed between a basic lysine residue and an acidic aspartame or glutamate residue (Condon, S M. et al., *J. Am. Chem. Soc.* 122: 3007-3014 (2000)). Lactam bridge formation is a well-known method by which the bioactive conformation of peptides may be deduced (See Id.). Incorporation of lactam bridges between residues 13 and 17; 18 and 22; and 26 and 30 in human PTH (1-31) and (1-34) (hPTH) has shown bioactivity while retaining a helical conformation (see Id.). Additionally, these modifications of hPTH(1-31) and hPTH(1-34) suggest that an α-helix may be the preferred bioactive conformation for the N-terminal portion of PTH (Shimizu, N. et al., *J. Biol. Chem.* 276: 490003-49012 (2001)).

Recently, it was also discovered that PTH(1-14) analogs containing the α,α-disubstitued amino acid, α-amino-isobutyric acid (Aib) at positions 1 and/or 3 have 10- to 100-fold higher affinities and cAMP signaling potencies than do their counterpart peptides containing alanine at these positions (Shimizu, N. et al. *J. Biol. Chem.* 276: 49003-49012 (2001)).

BRIEF SUMMARY OF THE INVENTION

The invention provides novel P1R polypeptide antagonists. These antagonists contain amino acid substitutions at selected positions in truncated PTH and PRHrP polypeptides and bind selectively to the juxtamembrane ("J") domain of the receptor. The J domain is the region of the receptor (P1R) containing the seven transmembrane helices and extracellular loops. N-terminal PTH antagonist analogs of the present invention, that bind to the J domain of the P1R, would be useful for treating conditions relating to PTH/P1R hyperactivity (e.g., primary hyperparathyroidism, Jansen's chondrodysplasia). In addition, these analogs would be useful for identifying other ligands (e.g., utilizing a high-throughput screen) that bind to P1R, such as small molecule PTH mimetic compounds. Moreover, these analogs could be used for pharmacologically analyzing P1R ligands for their selectivity, for example for the J domain.

The invention provides derivatives of PTH (1-21), PTH(1-20), PTH(1-19), PTH(1-18), PTH(1-17), PTH(1-16), PTH(1-15), PTH(1-14), PTH(1-13), PTH(1-12), PTH(1-11) and PTH(1-10) polypeptides, wherein said derivatives bind selectively to the J domain of P1R and act as antagonists or inverse agonists of P1R activity. The invention also provides methods of making such peptides. Further, the invention encompasses compositions and methods for use of such peptides in receptor-ligand assays. Additionally, the invention provides compositions and methods for use of such peptides in treating conditions associated with elevated levels of PTH, including, for example, hypercalcemia, and conditions related to hyperparathyroidism.

In one aspect, the invention is directed to a peptide selected from a group consisting of: $X_{01}X_{02}X_{03}$GluIleGlnLeu$X_{04}$His$X_{05}X_{06}X_{07}$Lys$X_{08}$ (SEQ ID NO: 1), wherein $X_{01}$ and $X_{03}$ are α-helix stabilizing residues (e.g., Ac$_3$c, Ac$_3$c, Deg, Aib or the desamino form of Ac$_3$c, Ac$_3$c, Deg, or Aib); $X_{02}$ is Trp, Bpa, Arg or Val; $X_{04}$ is Met or Nle; $X_{05}$ is Gln, Deg or Asn; $X_{06}$ is Har or Leu; $X_{07}$ is an α-helix stabilizing residue (e.g., Aib), Ala or Gly; and $X_{08}$ is an α-helix stabilizing residue (e.g., Aib), Trp, Tyr or His; fragments thereof, containing amino acids 1-9, 1-10, 1-11, 1-12 or 1-13; pharmaceutically acceptable salts thereof; and N- or C-derivatives thereof. In one embodiment of the present invention, the peptide above consists essentially of $X_{01}X_{02}X_{03}$GluIleGlnLeu$X_{04}$H is $X_{05}X_{06}X_{07}$Lys$X_{08}$ (SEQ ID NO: 1), wherein $X_{01}$ and $X_{03}$ are α-helix stabilizing residues (e.g., Ac$_3$c, Ac$_3$c, Deg, Aib or the desamino form of Ac$_5$c, Ac$_3$c, Deg, or Aib); $X_{02}$ is Trp, Bpa, Arg or Val; $X_{04}$ is Met or Nle; $X_{05}$ is Gln, Deg or Asn; $X_{06}$ is Har or Leu; $X_{07}$ is an α-helix stabilizing residue (e.g., Aib), Ala or Gly, and $X_{08}$ is an α-helix stabilizing residue (e.g., Aib), Trp, Tyr or His; fragments thereof, containing amino acids 1-9, 1-10, 1-11, 1-12 or 1-13; pharmaceutically acceptable salts thereof; and N- or C-derivatives thereof The invention is further drawn to fragments of the peptide of SEQ ID NO: 1, in particular $X_{01}X_{02}X_{03}$GluIleGlnLeu$X_{04}$His$X_{05}X_{06}X_{07}$Lys (SEQ ID NO: 2), $X_{01}X_{02}X_{03}$GluIleGlnLeu$X_{04}$His$X_{05}X_{06}X_{07}$ (SEQ ID NO: 3), $X_{01}X_{02}X_{03}$GluIleGlnLeu$X_{04}$His$X_{05}X_{06}$ (SEQ ID NO: 4) and $X_{01}X_{02}X_{03}$GluIleGlnLeu$X_{04}$His$X_{05}$ (SEQ ID NO: 5). The invention further encompasses pharmaceutically acceptable salts of the above-described peptides, and N- or C-derivatives of the peptides. An embodiment of the invention is drawn to any of the above recited polypeptides, wherein said polypeptide contains a C-terminal amide.

Another aspect of the invention is directed to a peptide consisting of $X_{01}$Bpa$X_{02}$GluIleGlnLeu$X_{03}$His$X_{04}X_{05}X_{06}$Lys$X_{07}$LeuAlaSerVal$X_{08}$Arg$X_{09}$ (SEQ ID NO: 6), wherein $X_{01}$ and $X_{02}$ are α-helix stabilizing residues (e.g., Ac$_5$c, Ac$_3$c, Deg, or Aib), $X_{03}$ is Aib, Gln, Deg or Asn, $X_{04}$ is Met or Nle, $X_{05}$ is Har or Leu, $X_{06}$ is an α-helix stabilizing residue (e.g. Aib), Ala or Gly, $X_{08}$ is an α-helix stabilizing residue (e.g. Aib) or Lys, and $X_{07}$ is an α-helix stabilizing residue (e.g. Aib), Trp or His, $X_{08}$ is Arg or Glu and $X_{09}$ is Tyr or Met; wherein said peptide binds selectively to the J domain of P1R.

The invention is further drawn to fragments of the peptide of SEQ ID NO: 6 in particular $X_{01}$Bpa$X_{02}$GluIleGlnLeu$X_{03}$His$X_{04}X_{05}X_{06}$Lys$X_{07}$LeuAlaSerVal$X_{08}$Arg(SEQ ID NO: 7), $X_{01}$Bpa$X_{02}$GluIleGlnLeu$X_{03}$His$X_{04}X_{05}X_{06}$Lys$X_{07}$LeuAlaSerVal$X_{08}$ (SEQ ID NO: 8), $X_{01}$Bpa$X_{02}$GluIleGlnLeu$X_{03}$His$X_{04}X_{05}X_{06}$Lys$X_{07}$LeuAlaSerVal (SEQ ID NO:9), $X_{01}$Bpa$X_{02}$GluIleGlnLeu$X_{03}$His$X_{04}X_{05}X_{06}$Lys$X_{07}$LeuAlaSer(SEQ ID NO: 10), $X_{01}$Bpa$X_{02}$GluIleGlnLeu$X_{03}$His$X_{04}X_{05}X_{06}$Lys$X_{07}$LeuAla (SEQ ID NO: 11) and $X_{01}$Bpa$X_{02}$GluIleGlnLeu$X_{03}$His$X_{04}X_{05}X_{06}$Lys$X_{07}$Leu (SEQ ID NO: 12). The invention further encompasses pharmaceutically acceptable salts of the above-described peptides, and N- or C-derivatives of the peptides. An embodiment of the invention is drawn to any of the above recited polypeptides, wherein said polypeptide contains a C-terminal amide.

The invention is further drawn to any of the above polypeptides labeled with a label selected from the group consisting of: a radiolabel, a flourescent label, a bioluminescent label, or a chemiluminescent label. In an embodiment the radiolabel is $^{125}$I or $^{99m}$Tc.

Embodiments of the peptide according to the present invention include: Ac$_5$cBpaAibGluIleGlnLeuMetHisGlnHarAlaLysTrp (SEQ ID NO: 13), Ac$_5$cValAibGluIleGlnLeuMetHisGlnHarAlaLysTrpNH$_2$ (SEQ ID NO: 14), (desNH2)Ac$_5$cValAibGluIleGlnLeuMetHisGlnHarAla-LysTrpNH$_2$ (SEQ ID NO: 15), (desNH2)AibValAibGluIleGlnLeuMetHisGlnHarAla-LysTrpNH$_2$(SEQ ID NO: 16), Ac$_5$cTrpAibGluIleGlnLeuMetHisGlnHarAlaLysTrpNH$_2$ (SEQ ID NO: 17) Ac$_5$cBpaAibGluIleGlnLeuMetHisGlnHarAlaLysTrpNH$_2$ (SEQ ID NO: 18), Ac$_5$cArgAibGluIleGlnLeuMetHisGlnHarAlaLysTrpNH$_2$ (SEQ ID NO: 19), DegValDegGluIleGlnLeuMetHis- GlnHarAlaLysTrpNH$_2$ (SEQ ID NO: 20), DegTrpDegGluIleGlnLeuMetHisGlnHarAlaLysTrpNH2 (SEQ ID NO: 21), DegBpaDegGluIleGlnLeuMetHisGlnHarAlaLysTrpNH$_2$ (SEQ ID NO: 22), Ac$_5$cTrpAibGluIleGlnLeuNleHisGlnHarAlaLysTyrNH$_2$ (SEQ ID NO: 23), Ac$_5$cBpaAibGluIleGlnLeuNleHisGlnHarAlaLysTyrNH$_2$ (SEQ ID NO: 24) and DegBpaDegGluIleGlnLeuNleHisGlnHarAlaLysTrpLeuAlaSerValArgArgTyrNH$_2$ (SEQ ID NO: 25).

In another aspect, the invention is directed to methods of making any of the above peptides, including a method wherein the peptide is synthesized by solid phase synthesis. The invention is also directed to a method of making any of the above peptides, wherein the peptide is protected by FMOC.

In a further aspect of the invention, this invention also provides pharmaceutical compositions comprising a peptide of the present invention and a pharmaceutically acceptable excipient and/or a pharmaceutically acceptable solution such as saline or a physiologically buffered solution.

This invention also provides a method for treating mammalian conditions characterized by increased PTH activity, such as, for example hypercalcemia, which method comprises administering to a subject in need thereof an effective amount of a peptide of the present invention. An embodiment of the invention is drawn to conditions such as hypercalcemia. Additional embodiments include using an effective amounts of the polypeptide of about 0.01 µg/kg/day to about 1.0 µg/kg/day wherein the polypeptide may be administer parenterally, subcutaneously or by nasal insufflation.

In accordance with yet a further aspect of the invention, this invention also provides a method for using the J-domain selective peptides in ligand-receptor assays. According to the method, the peptide maybe labeled with a label selected from the group consisting of: radiolabel, flourescent label, bioluminescent label, or chemiluminescent label. Examples of a suitable radiolabel are $^{125}$I or $^{99m}$Tc.

The invention is further related to a method of blocking increases in cAMP in a mammalian cell having PTH-1 receptors, said method comprising contacting the cell with a sufficient amount of the polypeptide of the invention to block increases in cAMP.

BRIEF DESCRIPTION OF THE FIGURES

FIG. 1. PTH Analogs Utilized and Their Amino Acid Sequences. All peptides are derived from the rat PTH sequence. Non-conventional amino acids include homoarginine (Har), norleucine (Nle); 1-aminoisobutyric acid (Aib); 1-aminocyclopropane-1-carboxylic acid (Ac$_3$c), diethylglycine (Deg), 1-aminocyclopentane-1-carboxylic acid (Ac$_5$c). The amino acids conferring antagonist properties to the peptides are in boldface type. The asterisk indicates the iodinated tyrosine.

FIG. 2. Binding of PTH Analogs in HKRK-B28 Cells. The parent peptide was [Ac$_3$c$^1$,Aib$^3$,Gln$^{10}$,Har$^{11}$,Ala$^{12}$,Trp$^{14}$]PTH(1-14)NH$_2$ and derivatives thereof were substituted at positions 1, 2 and/or 3 as indicated. Binding assays were performed with $^{125}$I-[Aib$^{1,3}$,Nle$^8$,Gln$^{10}$, Har$^{11}$,Ala$^{12}$,Trp$^{14}$,Tyr$^{15}$]PTH(1-15)NH$_2$. Data are from the number of experiments indicated (n), each performed in duplicate.

FIG. 3. Functional Responses in HKRK-B28 Cells. Binding (A and B) and cAMP agonism/partial agonism assays (C) were performed in HKRK-B28 cells. The parent peptide was [Ac$_5$c$^1$,Aib$^3$,Gln$^{10}$,Har$^{11}$, Ala$^{12}$,Trp$^{14}$]PTH(1-14)NH$_2$ and derivatives thereof were substituted at positions 1, 2 and/or 3 as indicated. Binding assays (4h at 15° C.) were performed with $^{125}$I-[Aib$^{1,3}$, Nle$^8$,Gln$^{10}$,Har$^{11}$,Ala$^{12}$,Trp$^{14}$,Tyr$^{15}$)PTH(1-15)NH$_2$ tracer. cAMP assays were performed at RT for 30 min. Relative to the parent, the substituted analogs displayed reduced agonist activity.

FIG. 4. cAMP Responses in HKRK-B28 Cells. The parent peptide, [Ac$_5$c$^1$,Aib$^3$,Gln$^{10}$,Har$^{11}$,Ala$^{12}$,Trp$^{14}$]PTH(1-14)NH$_2$ and derivatives thereof substituted at positions 1, 2 and/or 3 as indicated, were assayed for cAMP agonist responses in HKRK-B28 cells. The parent peptide functions as a fully potent and efficacious agonist, the Deg$^{1,3}$-substituted analog is a partial agonist, and the Bpa$^2$-substituted analogs lack agonist activity.

FIG. 5. Antagonism Assays in HK-RK-B28 Cells. cAMP antagonism assays were performed in HKRK-B28 cells. Cells were treated with the J domain-selective agonist, [Ac$_5$c$^1$,Aib$^3$,Gln$^{10}$,Har$^{11}$, Ma$^{12}$,Trp$^{14}$]PTH(1-14)NH$_2$ (parent) at 10 nM, either alone (none) or with a candidate antagonist peptide (10 µM), which was a derivative of the parent PTH(1-14) peptide substituted at positions 1, 2 and/or 3 as indicated, or [I$^5$,W$^{23}$,Y$^{36}$]PTHrP(5-36) analog. Asterisks indicate significant reductions in cAMP levels, as compared to cells not treated with antagonist (none).

FIG. 6. Antagonism Assays in COS-7 Cells. cAMP antagonism assays were performed in COS-7 cells transfect with the wild-type P1R (A), or a constitutively active P1R derivative having the first 9 residues of PTH tethered to TM1 of the P1R and in place of the P1R N-terminal domain (inset), B). In A, cells were treated with the J domain-selective agonist, [Ac$_5$c$^1$, Aib$^3$,Gln$^{10}$,Har$^{11}$,Ala$^{12}$,Trp$^{14}$]PTH(1-14)NH$^2$ (parent) at 1 nM, alone (none) or with a candidate antagonist peptide (10 µM), which was a derivative of the parent PTH(1-14) peptide substituted at positions 1, 2 and/or 3 as indicated, or [I$^5$,W$^{23}$,Y$^{36}$]PTHrP(5-36) analog. Asterisks indicate significant reductions in cAMP levels, as compared to cells not treated with antagonist (none).

FIG. 7. Inverse Agonist Responses in COS-7 Cells. COS-7 cells were transfected with the constitutively active P1Rs: P1R-H223R (A), P1R-T410P (B), P1R-H223R/T410P (C), or P1R-I458R (D) and then were incubated (30 min at RT) either in the absence of peptide (none) or in the presence of the indicated antagonist/inverse agonist peptide (10 µM), and cAMP was measured by RIA. Asterisks indicate significant reductions in cAMP levels, compared to untreated cells (none).

FIG. 8. "N" versus "J" Domain selectivity of P1R Antagonists in COS-7 Cells. cAMP antagonism assays were performed in COS-7 cells transfect with the wild-type P1R (A), or a P1R derivative (P1R-delNt) having most (residues 24-181) of the P1R N domain deleted (B). Cells were treated with the agonist [Aib$^{1,3}$,Tyr$^{34}$]hpTH(1-34)NH$_2$ ([Aib$^{1,3}$]PTH(1-34)), which utilizes both N and J domains for affinity/potency, or with [Ac$_5$c$^1$, Aib$^3$, Gln$^{10}$,Har$^{11}$,Ala$^{12}$,Trp$^{14}$]PTH(1-14)NH$_2$ ([Ac5c$^1$]PTH(1-14)), which uses only the J domain for affinity/potency, at the concentrations indicated in the key, so as to elicit half-maximum cAMP responses in the absence of antagonist (none). The analogs PTHrP(5-36) and Deg$^{1,3}$,Bpa$^2$-PTH(1-21) were added at 1×10–5 M, as indicated. On the WT receptor, PTHrP(5-36) antagonizes PTH(1-34) analog more effectively than does Deg$^{1,3}$,Bpa$^2$-PTH(1-21), but the PTH(1-21) analog antagonizes PTH(1- 14), more effectively than does PTHrP(5-36). On P1R-delNt, Deg$^{1,3}$,Bpa$^2$-PTH(1-21) antagonizes either agonist, whereas PTHrP(5-36) lacks antagonist capability. Thus, PTHrP(5-36) is an N domain-selective antagonist, whereas Deg$^{1,3}$,Bpa$^2$-

Figure 9:
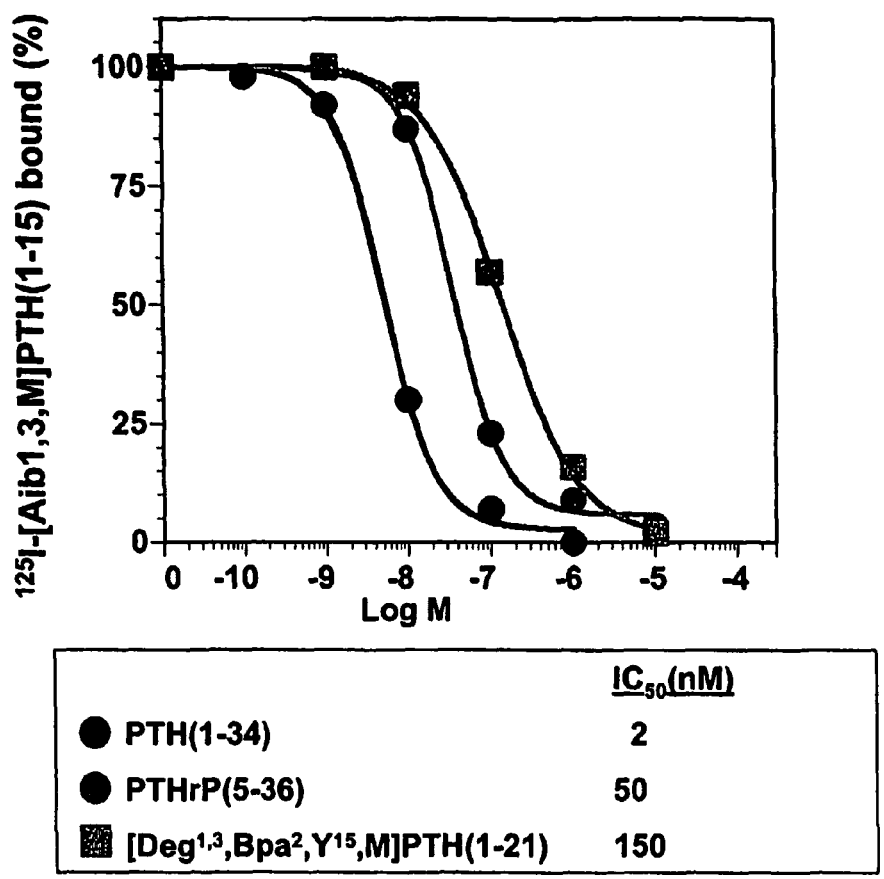

PTH(1-21) is a J domain-selective antagonist. The analog Deg$^{1,3}$,Bpa$^2$-PTH(1-14) behaved similarly in these assays to Deg$^{1,3}$,Bpa$^2$-PTH(1-21).

FIG. 9. Competition Binding Assays in HKRK-B7 Cells. Binding assays were performed in HKRK-B7 cells, which express the wild-type hP1R, using $^{125}$I-[Aib$^{1,3}$,Nle$^8$,Gln$^{10}$, Har$^{11}$,Ala$^{12}$,Trp$^{14}$,Tyr$^{15}$]PTH(1-15)NH$_2$ as a tracer radioligand and the indicated unlabeled peptides as competitors. PTH(1-34) is [Tyr$^{34}$]hPTH(1-34)NH$_2$.

FIG. 10. Competitive Antagonism on P1R-delNt. COS-7 cells transfected with P1R-delNt were stimulated with varying concentrations of the agonist [Aib$^{1,3}$,Tyr$^{34}$]hPTH(1-34) NH$_2$ ([Aib$^{1,3}$]PTH(1-34)), either in the absence of antagonist or in the presence of an antagonist, [Deg$^{1,3}$,Bpa$_2$,M]PTH(1-14) or [Deg$^{1,3}$,Bpa$^2$,M]PTH(1-21) each at 1×10–5 M, as indicated in the figure key. Each antagonist causes a parallel, right-ward shift in the agonist dose-response curve, which is consistent with a competitive mechanism of inhibition.

FIG. 11. A model of the interaction between PTH derivatives of the present invention and the J domain of the P1R receptor.

DETAILED DESCRIPTION OF THE INVENTION

Definitions

"A," "an," "the," and the like, unless otherwise indicated, may include plural forms. Also, reference to singular forms embrace plural forms. Therefore, for example, peptide also encompasses peptides.

Amino Acid Sequences: The amino acid sequences in this application use either the single letter or three letter designations for the amino acids. These designations are well known to one of skill in the art and can be found in numerous readily available references, such as for example in Cooper, G. M., *The Cell* 1997, ASM Press, Washington, D.C. or Ausubel et al., *Current Protocols in Molecular Biology*, 1994. Where substitutions in a sequence are referred to, for example, as Ser-3-->Ala or [Ala$^3$]peptide, this means that the serine in the third position from the N-terminal end of the polypeptide is replaced with another amino acid, Alanine in this instance.

In the present application, "Aib" refers to α-aminoisobutyric acid; "Har" refers to homoarginine; "Nle" refers to norleucine; AC$_3$C refers to 1-aminocyclopropane-1-carboxylic acid; AC$_5$C refers to 1-aminocyclopentane-1-carboxylic acid; Har refers to homoarginine; Deg refers to diethylglycine; and other amino acids are in either the conventional one- or three-letter codes.

Biological Activity of the Protein: This expression refers to any biological activity of the polypeptide. Examples of these activities include, but are not limited to metabolic or physiologic function of compounds of SEQ ID NO: 1 or derivatives thereof, including similar activities or improved activities, or those activities with decreased undesirable side-effects. Also included are antigenic and immunogenic activities of the above-described compounds.

Derivative or Functional Derivative: The term "derivative" or "functional derivative" is intended to include "variants," the "derivatives," or "chemical derivatives" of PTH molecules. A "variant" of a molecule such as for example, a compound of SEQ ID NO: 1 or derivative thereof is meant to refer to a molecule substantially similar to either the entire molecule, or a fragment thereof. An "analog" of a molecule such as for example, a compound of SEQ ID NO: 1 or derivative thereof is meant to refer to a non-natural molecule substantially similar to either the SEQ ID NO: 1 molecules or fragments thereof.

PTH derivatives contain changes in the polypeptide relative to the native PTH polypeptide of the same size. The sequence of the native PTH(1-14) polypeptide is the first fourteen amino acids of SEQ. ID NO: 17 (human PTH (1-21)) or SEQ. ID NO: 18(rat PTH (1-21)). A molecule is said to be "substantially similar" to another molecule if the sequence of amino acids in both molecules is substantially the same, and if both molecules possess a similar biological activity. Thus, two molecules that possess a similar activity, may be considered variants, derivatives, or analogs as that term is used herein even if one of the molecules contains additional amino acid residues not found in the other, or if the sequence of amino acid residues is not identical. PTH derivatives, however, need not have substantially similar biological activity to the native molecule. In some instances PTH derivatives may have substantially different activity than the native PTH. For example, a derivative may be either an antagonist or an agonist of the PTH receptor.

As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Examples of moieties capable of mediating such effects are disclosed in *Remington's Pharmaceutical Sciences* (1980) and will be apparent to those of ordinary skill in the art.

Fragment: A "fragment" of a molecule such as, for example, SEQ ID NO: 1 or derivative thereof is meant to refer to any polypeptide subset of these molecules.

Fusion protein: By the term "fusion protein" is intended a fused protein comprising compounds such as for example, SEQ ID NO: 1 or derivatives thereof, either with or without a "selective cleavage site" linked at its N-terminus, which is in turn linked to an additional amino acid leader polypeptide sequence.

J domain: The J domain is the domain of the P1R spanning the region of the receptor comprising the seven transmembrane domains and the extracellular loops.

Polypeptide: Polypeptide and peptide are used interchangeably. The term polypeptide refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids and include amino acid sequences modified either by natural processes, such as post-translational processing, or by chemical modification techniques which are well known in the art. Such modifications are well described in basic texts and in more detailed monographs, as well as in the research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

Polypeptides may be branched and they may be cyclic, with or without branching. Cyclic, branched and branched cyclic polypeptides may result from post-translational modifications or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, *Proteins-Structure and Molecular Properties*, 2nd Ed., T. E. Creighton, W. H. Freeman and Company, New York, 1993 and Wold, F., Posttranslational Protein Modifications: Perspectives and Prospects, pgs. 1-12 in *Posttranslational Covalent Modification of Proteins*, B. C. Johnson, Ed., Academic Press, New York, 1983; Seifter et al., "Analysis for protein modifications and nonprotein cofactors", *Methods in Enzymol.* 182: 626-646 (1990) and Rattan et al., "Protein Synthesis: Posttranslational Modifications and Aging", *Ann NY Acad Sci* 663: 48-62 (1992).

PTH Analogs—Structural and Functional Properties

α-aminoisobutyric acid (Aib) was introduced into short N-terminal PTH peptide analogs. The numerous NMR studies of PTH(1-34) analogs, performed in a variety of polar or non-polar solvents, have generally indicated two domains of secondary structure: a stable C-terminal helix extending approximately from Ser-17 to Val-31, and a shorter and less stable amino-terminal helix, extending variably from Ser-3 to Lys-13, the two domain being connected by a bend or turn region (Marx, U. C., et al., *Biochem. Biophys. Res. Commun.* 267: 213-220 (2000); Chen, Z., et al., *Biochemistry* 39: 12766-12777 (2000); Marx, U. C., et al., *J. Biol. Chem.* 270: 15194-15202 (1995); Marx, U. C., et al., *J. Biol. Chem.* 273: 4308-4316 (1998); Pellegrini, M., et al., *Biochemistry* 37: 12737-12743 (1998); Gronwald, W., et al., *Biol. Chem. Hoppe Seyler* 377: 175-186 (1996); Barden, J. A., and Kemp, B. E., *Biochemistry* 32: 7126-7132 (1993)). The recent crystallographic study of PTH(1-34) indicated a continuous α-helix extending from Ser-3 to His-32 and containing only a slight 15° bend at the midsection. However, NMR data indicates that the N-terminal α-helix is relatively weak. Helix-stabilizing modifications, such as the introduction of Aib residues, offer significant benefits in terms of binding affinity to the P1R receptor, and result in short peptides ($\leq 14$ amino acids) with binding affinity that is comparable to PTH(1-34).

Described herein are novel "minimized" variants of PTH or PTHrP that are small enough to be deliverable by simple non-injection methods and that act as antagonists or inverse agonists by binding to the J domain of the P1R. The variants of the present invention contain substitutions in the first 21 amino acids of the polypeptide. The new polypeptides correspond to the 1-21, 1-20, 1-19, 1-18, 1-17, 1-16, 1-15, 1-14, 1-13, 1-12, 1-11, and 1-10 amino acid sequence of the mature PTH polypeptide. The shorter variants ($\leq$PTH1-14) have a molecular weight of less than 2,000 daltons.

The primary amino acid sequence of the native human PTH(1-21) peptide (N-terminus to C-terminus) is SerValSerGluIleGlnLeuMetHisAsnLeuGlyLysHisLeuAsnSerMetGluArgVal (SEQ ID NO: 26), whereas the primary sequence of the native rat PTH (1-21) is AlaValSerGluIleGluMetHisAsnLeuGlyLysHisLeuAlaSerValGluArgMet (SEQ ID NO: 27).

As protein products, compounds described herein are amenable to production by the techniques of solution- or solid-phase peptide synthesis and by in-situ synthesis using combination chemistry. The solid phase peptide synthesis technique, in particular, has been successfully applied in the production of human PTH and can be used for the production of these compounds (for guidance, see Kimura et al., supra, and see Fairwell et al., *Biochem.* 22: 2691 (1983)). Success with producing human PTH on a relatively large scale has been reported by Goud et al., in *J. Bone Min. Res.* 6(8):781 (1991). The synthetic peptide synthesis approach generally entails the use of automated synthesizers and appropriate resin as solid phase, to which is attached the C-terminal amino acid of the desired compounds of SEQ ID NO: 1 or derivatives thereof. Extension of the peptide in the N-terminal direction is then achieved by successively coupling a suitably protected form of the next desired amino acid, using either FMOC- or BOC-based chemical protocols typically, until synthesis is complete. Protecting groups are then cleaved from the peptide, usually simultaneously with cleavage of peptide from the resin, and the peptide is then isolated and purified using conventional techniques, such as by reversed phase HPLC using acetonitrile as solvent and tri-fluoroacetic acid as ion-pairing agent. Such procedures are generally described in numerous publications and reference may be made, for example, to Stewart and Young, "Solid Phase Peptide Synthesis," 2nd Edition, Pierce Chemical Company, Rockford, Ill. (1984). It will be appreciated that the peptide synthesis approach is required for production of such as for example, SEQ ID NO: 1 and derivatives thereof which incorporate amino acids that are not genetically encoded, such as Aib.

In accordance with another aspect of the present invention, substituents may be attached to the free amine of the N-terminal amino acid of compounds of the present invention standard methods known in the art. For example, alkyl groups, e.g., $C_{1-12}$ alkyl, may be attached using reductive alkylation. Hydroxyalkyl groups, e.g. $C_{1-12}$ hydroxyalkyl, may also be attached using reductive alkylation wherein the free hydroxy group is protected with a t-butyl ester. Acyl groups, e.g., $COE_1$ may be attached by coupling the free acid, e.g., $E_1COOH$, to the free amino of the N-terminal amino acid. Additionally, possible chemical modifications of the C-terminal end of the polypeptide are encompassed within the scope of the invention. These modifications may modify binding affinity to the receptor.

Also contemplated within the scope of this invention are those compounds such as for example, SEQ ID NO: 1 and derivatives thereof with altered secondary or tertiary structure, and/or altered stability, which retain selectivity for the J-domain of P1R and also retain antagonistic or reverse-agonist activity. Such derivatives might be achieved through lactam cyclization, disulfide bonds, or other means known to a person of ordinary skill in the art.

Utility and Administration of Compounds of the Invention

Compounds of the invention or derivatives thereof have multiple uses due, in part to their ability to act as antagonists or inverse agonists of P1R. The multiple uses of the peptides of the present invention include, inter alia, prevention and treatment of a variety of mammalian conditions manifested by increased activity and/or production of PTH or PTHrP, diagnostic probes, antigens to prepare antibodies for use as diagnostic probes and even as molecular weight markers. Being able to specifically substitute one or more amino acids in the PTH polypeptide permits construction of specific molecular weight polypeptides.

In particular, the compounds of this invention are indicated for the prophylaxis and therapeutic treatment of hypercalcemia and for treatment of hyperparathyroidism, Jansen's chondrodysplasia, or condition related thereto.

In certain embodiments, compounds of the present invention, or salts thereof, are administered in amounts necessary to treat a patient in need of treatment for conditions requiring antagonists of PTH receptors. In some embodiments, the compounds are administered between about 0.01 and 1 µg/kg body weight per day, preferably from about 0.07 to about 0.2 µg/kg body weight per day. For a 50 kg human female subject, the daily dose of biologically active compound is from about 0.5 to about 50 µgs, preferably from about 3.5 to about 10 µgs. In other mammals, such as horses, dogs, and cattle, higher doses may be required. This dosage may be delivered in a conventional pharmaceutical composition by a single administration, by multiple applications, or via controlled release, as needed to achieve the most effective results, preferably one or more times daily by injection. For example, this dosage may be delivered in a conventional pharmaceutical composition by nasal insufflation.

The selection of the exact dose and composition and the most appropriate delivery regimen will be influenced by, inter alia, the pharmacological properties of the selected compounds of the invention, the nature and severity of the condition being treated, and the physical condition and mental acuity of the recipient.

Representative delivery regimens include, without limitation, oral, parenteral, subcutaneous, transcutaneous, intramuscular and intravenous, rectal, buccal (including sublingual), transdermal, and intranasal insufflation.

Pharmaceutically acceptable salts retain the desired biological activity of the compounds of the invention without toxic side effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalene disulfonic acids, polygalacturonic acid and the like; (b) base addition salts formed with polyvalent metal cations such as zinc, calcium, bismuth, barium, magnesium, aluminum, copper, cobalt, nickel, cadmium, and the like; or with an organic cation formed from N,N'-dibenzylethylenediamine or ethylenediamine; or (c) combinations of (a) and (b), e.g., a zinc tannate salt and the like. Pharmaceutically acceptable buffers include but are not limited to saline or phosphate buffered saline. Also included in these solutions may be acceptable preservative known to those of skill in the art. Like PTH, the PTH variants may be administered in combination with other agents useful in treating a given clinical condition.

A further aspect of the present invention relates to pharmaceutical compositions comprising as an active ingredient compounds of the invention or derivatives thereof of the present invention, or pharmaceutically acceptable salt thereof, in admixture with a pharmaceutically acceptable, non-toxic carrier. As mentioned above, such compositions may be prepared for parenteral (subcutaneous, transcutaneous, intramuscular or intravenous) administration, particularly in the form of liquid solutions or suspensions; for oral or buccal administration, particularly in the form of tablets or capsules; for rectal, transdermal administration; and for intranasal administration, particularly in the form of powders, nasal drops or aerosols.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985), incorporated herein by reference. Formulations for parenteral administration may contain as excipients sterile water or saline, alkylene glycols such as propylene glycol, polyalkylene glycols such as polyethylene glycol, oils of vegetable origin, hydrogenated naphthalenes and the like. For oral administration, the formulation can be enhanced by the addition of bile salts or acylcarnitines. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

When formulated for nasal administration, the absorption across the nasal mucous membrane may be enhanced by surfactant acids, such as for example, glycocholic acid, cholic acid, taurocholic acid, ethocholic acid, deoxycholic acid, chenodeoxycholic acid, dehydrocholic acid, glycodeoxycholic acid, cyclodextrins and the like in an amount in the range between about 0.2 and 15 weight percent, preferably between about 0.5 and 4 weight percent, most preferably about 2 weight percent.

Delivery of the compounds of the present invention to the subject over prolonged periods of time, for example, for periods of one week to one year, may be accomplished by a single administration of a controlled release system containing sufficient active ingredient for the desired release period. Various controlled release systems, such as monolithic or reservoir-type microcapsules, depot implants, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

One form of controlled release formulation contains the polypeptide or its salt dispersed or encapsulated in a slowly degrading, non-toxic, non-antigenic polymer such as copoly (lactic/glycolic) acid, as described in the pioneering work of Kent, Lewis, Sanders, and Tice, U.S. Pat. No. 4,675,189. The compounds or their relatively insoluble salts, may also be formulated in cholesterol or other lipid matrix pellets, or silastomer matrix implants. Additional slow release, depot implant or injectable formulations will be apparent to the skilled artisan. See, for example, Sustained and Controlled Release Drug Delivery Systems, J. R. Robinson ed., Marcel Dekker, Inc.,. New York, 1978, and R. W. Baker, Controlled Release of Biologically Active Agents, John Wiley & Sons, New York, 1987.

PTH Analog Receptor-Signaling Activities

A crucial step in hormonal action is the interaction of hormones with receptors on the plasma membrane surface of target cells. The formation of hormone-receptor complexes allows the transduction of extracellular signals into the cell to elicit a variety of biological responses.

Polypeptides described herein can be screened for their antagonistic or inverse agonistic properties using the cAMP accumulation assay. In one such assay, cells expressing PTH-1 receptor on the cell surface are incubated with native PTH(1-84) for 5-60 minutes at 37° C., in the presence of 2 mM IBMX (3-isobutyl-1-methyl-xanthine, Sigma, St. Louis, Mo.). Cyclic AMP accumulation is measured by specific radio-immunoassay. A compound that competes with native PTH(1-84) or PTH(1-34), or any fragments thereof, for binding to the PTH-1 receptor, and that inhibits the effect of native PTH(1-84) or PTH(1-34) on cAMP accumulation, is considered a competitive antagonist. Such a compound would be useful for treating hypercalcemia.

Conversely, a PTH analog described herein or a derivative thereof that does not compete with native PTH(1-84) or PTH (1-34) for binding to the PTH-1 receptor, but which still prevents native PTH(1-84) or PTH(1-34) activation of cAMP accumulation (presumably by blocking the receptor activation site) is considered a non-competitive antagonist. Such a compound would also be useful for treating hypercalcemia.

Therapeutic Uses of PTH Analogs

Some forms of hypercalcemia are related to the interaction between PTH and PTHrP and the PTH-1 and PTH-2 receptors. Hypercalcemia is a condition in which there is an abnormal elevation in serum calcium level; it is often associated with other diseases, including hyperparathyroidism, osteoporosis, carcinomas of the breast, lung and prostate, epidermoid cancers of the head and neck and of the esophagus, multiple myeloma, and hypernephroma.

By "agonist" is intended a ligand capable of enhancing or potentiating a cellular response mediated by the PTH-1 receptor. By "antagonist" is intended a ligand capable of inhibiting a cellular response mediated by the PTH-1 receptor. whether any peptide of the present invention is classified as an "agonist" or "antagonist," i.e., a compound that can enhance or inhibit such a cellular response, can be determined using art-known protein ligand/receptor cellular response or binding assays, including those described elsewhere in this application.

In accordance with yet a further aspect of the invention, there is provided a method for treating a medical disorder that results from altered or excessive action of the PTH-1 receptor, comprising administering to a patient therapeutically effective amount of a compound of the invention or a derivative thereof sufficient to inhibit activation of the PTH-1 receptor of said patient.

In this embodiment, a patient who is suspected of having a disorder resulting from altered action of the PTH-1 receptor can be treated using compounds of the invention or derivatives thereof of the invention which are a selective antagonists of the PTH-1 receptor. Such antagonists include compounds of the invention or derivatives thereof of the invention which have been determined (by the assays described herein) to interfere with PTH-1 receptor-mediated cell activation or other derivatives having similar properties.

To administer the antagonist, the appropriate compound of the invention or a derivative thereof is used in the manufacture of a medicament, generally by being formulated in an appropriate carrier or excipient such as, e.g., physiological saline, and administered intravenously, intramuscularly, subcutaneously, orally, or intranasally, at a dosage that provides adequate inhibition of a compound of the invention or a derivative thereof binding to the PTH-1 receptor. Typical dosage would be 1 ng to 10 mg of the peptide per kg body weight per day.

It will be appreciated to those skilled in the art that the invention can be performed within a wide range of equivalent parameters of composition, concentration, modes of administration, and conditions without departing from the spirit or scope of the invention or any embodiment thereof.

Having now fully described the invention, the same will be more readily understood by reference to specific examples which are provided by way of illustration, and are not intended to be limiting of the invention, unless herein specified.

EXAMPLES

The following protocols and experimental details are referenced in the examples that follow.

Peptides. Peptides are prepared on automated peptide synthesizers (model 430A PE, Applied Biosystems, Foster City, Calif., or Model 396 MBS Advanced Chem Tect, Louisville, Ky.) using FMOC main-chain protecting group chemistry, HBTU/HOBt/DIEBA (1:1:2 molar ratio) for coupling reactions, and TFA-mediated cleavage/sidechain-deprotection (MGH Biopolymer Synthesis Facility, Boston, Mass.). All peptides are desalted by adsorption on a C18-containing cartridge, and purified further by HPLC. The dry peptide powders are reconstituted in 10 mM acetic acid and stored at −80° C. The purity, identity, and stock concentration for each peptide is secured by analytical HPLC, Matrix-assisted laser desorption/ionization (MALDI) mass spectrometry and amino acid analysis. Radiolabeling is performed using $^{125}$I-Na (2,200 Ci/mmol, NEN) and chloramine-T; the resultant radioligands are purified by HPLC.

Cell Culture. The cell line HKRK-B28 (Shimizu, el al., Biochem. 41: 13224-33 (2002)) was derived from the porcine kidney cell line, LLC-$PK_1$ by stable transfection with plasmid DNA encoding the opossum/rat hybrid P1R and expresses ~280,000 receptors per cell. The HKRK-B7 cell line was derived from the LLC-$PK_1$ cell line by stable transfection with DNA encoding human P1R. HKRK-B7 cells expresses approximately 950,000 human P1R per cell (Takasu, H., et al., J. Bone Miner. Res. 14: 11-20 (1999)). These cells, as well as COS-7 cells and SaOS-2-B10 cells, are cultured at 27° C. in T-75 flasks (75 mm$^2$) in Dulbecco's modified Eagle's medium (DMEM) supplemented with fetal bovine serum (10%), penicillin G (20 units/ml), streptomycin sulfate (20 μg/ml) and amphotericin B (0.05 μg/ml) in a humidified atmosphere containing 5% $Co_2$. Stock solutions of EGTA/trypsin and antibiotics are from GIBCO; fetal bovine serum is from Hyclone Laboratories (Logan, Utah). COS-7 cells subcultured in 24-well plates are transfected with plasmid DNA (200 ng per well) encoding the wild-type human P1R or truncated human P1R deleted for residues (24-181) (Shimizu, M., et al., J. Biol. Chem. 275: 21836-21843 (2000)) that is purified by cesium chloride/ethidium bromide density gradient centrifugation, and FuGENE 6 transfection reagent (Roche Indianapolis Ind.) according to the manufacturer's recommended procedure. All cells, in 24-well plates, are treated with fresh media and shifted to 33° C. for 12 to 24 h prior to assay.

cAMP Stimulation. Stimulation of cells with peptide analogs is performed in 24-well plates. Cells are rinsed with 0.5 mL of binding buffer (50 mM Tris-HCl, 100 mM NaCl, 5 mM KCl, 2 mM $CaCl_2$, 5% heat-inactivated horse serum, 0.5% fetal bovine serum, adjusted to pH 7.5 with HCl) and treated with 200 μL of cAMP assay buffer (Delbecco's modified Eagle's medium containing 2 mM 3-isobutyl-1-methylxanthine, 1 mg/mL bovine serum albumin, 35 mM Hepes-NaOH, pH 7.4) and 100 μL of binding buffer containing varying amounts of peptide analog (final volume=300 μL). The medium is removed after incubation for 30 to 60 minutes at room temperature, and the cells are frozen on dry ice, lysed with 0.5 mL 50 mM HCl, and refrozen (~80° C.). The cAMP content of the diluted lysate is determined by radioimmunoassay. The $EC_{50}$ response values are calculated using non-linear regression (see below).

Competition Binding. Binding reactions are performed with HKRK-B28 cells, HKRK-B7 or in COS-7 cells in 24-well plates. The cells are rinsed with 0.5 mL of binding buffer, and then treated successively with 100 μL binding buffer, 100 μL of binding buffer containing various amounts of unlabeled competitor ligand, and 100 μL of binding buffer containing ca. 100,000 cpm of $^{125}$I-[M]PTH(1-21), $^{125}$I-[Aib$^{1,3}$, Nle$^8$,Gln$^{10}$,Har$^{11}$,Ala$^{12}$,Trp$^{14}$,Tyr$^{15}$]PTH(1-1-5) NH$_2$ or $^{125}$I-[Aib$^{1,3}$,M]PTH(1-21) (ca. 26 fmol; final volume=300 μL). Incubations are 4 to 6 h at 4° C., at which time near equilibrium conditions were attained. Cells are then placed on ice, the binding medium was removed, and the monolayer is rinsed three times with 0.5 mL of cold binding buffer. The cells were subsequently lysed with 0.5 mL 5N NaOH and counted for radioactivity. For each tracer and in each experiment, the non-specific binding is determined as the radioactivity that bound in the presence of the same unlabeled peptide at a concentration of 1 μM, and was ~1% of total radioactivity added for each tracer. The maximum specific binding (B$_0$) is the total radioactivity bound in the absence of competing ligand, corrected for nonspecific binding. Nonlinear regression is used to calculate binding IC$_{50}$ values (see below). Scatchard transformations of homologous competition binding data derived from studies with 26 fmol of $^{125}$I-[Aib$^{1,3}$,M]PTH(1-21) are employed for estimations of apparent equilibrium dissociation constant (k$_{Dapp}$s) and total number of ligand binding sites (B$_{max}$), assuming a single class of binding sites and equal affinities of the iodinated and non iodinated ligand.

Stimulation of Inositol Phosphate Production. COS-7 cells transfected as above with P1R-WT are treated with serum-free, inositol-free DMEM containing 0.1% bovine serum albumin and [$^3$H]myo-inositol (NEN, Boston, Mass.) (2 μCi/mL) for 16 h prior to assay. At the time of the assay, the cells are rinsed with binding buffer containing LiCl (30 mM) and treated with the same buffer with or without a PTH analog. The cells are then incubated at 37° C. for 40 min, after which the buffer was removed and replaced by 0.5 mL of ice cold 5% trichloroacetic acid solution. After 3 h on ice, the lysate is collected and extracted twice with ethyl ether. The lysate is then applied to an ion exchange column (0.5 mL resin bed) and the total inositol phosphates are eluted as described previously (Berridge, M. J., et al., Biochem. J. 212: 473-482 (1983)), and counted in liquid scintillation cocktail.

Example 1

Results

Binding assays of PTH derivatives were performed in HKRK-B28 cells. Derivatives of the parent peptide, [Ac$_5$c$^1$, Aib$^3$,Gln$^{10}$,Har$^{11}$,Ala$^{12}$,Trp$^{14}$]PTH(1-14)NH$_2$ (SEQ ID NO: 14), were substituted at positions 1, 2 and/or 3, as indicated. Binding assays (4 h at 15° C.) were performed with $^{125}$I [Aib$^{1,3}$,Nle$^8$,Gln$^{10}$,Har$^{11}$,Ala$^{12}$,Trp$^{14}$,Tyr$^{15}$]PTH(1-15) NH$_2$. The results indicate that the parent peptide bound with the highest affinity of the derivatives tested (FIG. 2 and FIG. 3(A)).

The parent peptide, [Ac$_5$c$^1$,Aib$^3$,Gln$^{10}$,Har$^{11}$,Ala$^{12}$,Trp$^{14}$] PTH(1-14)NH$_2$, and derivatives thereof substituted at positions 1, 2 and/or 3, as indicated, were assayed for cAMP agonist responses in HKRK-B28 cells (FIG. 3(C) and FIG. 4). The assays were performed at RT for 30 min. The parent peptide functions as a fully potent and efficacious agonist, the Deg$_{1,3}$-substituted analog is a partial agonist, and the Bpa$^2$-substituted analogs lack agonist activity. These results indicate a crucial role for position 2 in stimulating cAMP production.

The analogs also behave as inverse agonists in COS-7 cells expressing the constitutively active mutant human P1Rs derived from patients with Jansen's disease, P1R-H223R and P1R-H223R/T410P (FIGS. 7A and C). The analog [desNH$_2$-Ac$_5$c$^1$,Aib$^3$,Gln$^{10}$,Har$^{11}$,Ala$^{12}$,Trp$^{14}$]PTH(1-14)NH$_2$ behaved as an inverse agonist in COS-7 cells expressing the constitutively active mutant receptor P1R-T410P (FIG. 7B). None of the analogs is an inverse agonist in COS-7 cells expressing the constitutively active mutant receptor P1R-1458R (FIG. 7D), which appears to be a "locked-on" P1R. These results demonstrate the P1R-selectivity of the new analogs.

In COS-7 cells expressing P1R-delNt, [Deg$^{1,3}$,BPA$^2$,Nle$^8$, Gln$^{10}$,Har$^{11}$,Ala$^{12}$,Trp$^{14}$,Arg$^{19}$,Tyr$^{21}$]PTH(1-21 )NH$_2$ strongly inhibited both [Aib$^{1,3}$,Tyr$^{34}$]hPTH(1-34)NH$_2$ and Ac$_5$c$^1$,Aib$^3$,Gln$^{10}$,Har$^{11}$,Ala$^{12}$,Trp$^{14}$]PTH(1-14)NH$_2$ whereas [Ile$^5$,Trp$^{23}$,Tyr$^{36}$]PTHrP(5-36)NH$_2$ was inert on this receptor construct for either agonist ligand (FIG. 8B). These results demonstrate that [Deg$^{1,3}$,BPA$^2$,Nle$^8$,Gln$^{10}$,Har$^{11}$, Ala$^{12}$,Trp$^{14}$,Arg$^{19}$,Tyr$^{21}$]PTH(1-21)NH$_2$ is a potent J-domain selective antagonist. The differences in the antagonist actions of [Deg$^{1,3}$,BPA$^2$,Nle$^8$,Gln$^{10}$,Har$^{11}$,Ala$^{12}$,Trp$^{14}$, Arg$^{19}$,Tyr$^{21}$]PTH(1-21 )NH$_2$ and [Ile$^5$,Trp$^{23}$,Tyr$^{36}$]PTHrP(5-36)NH$_2$ on the intact human P1R (FIG. 6A) was not due to differences in binding affinities for this receptor, as shown by the similar IC$_{50}$ values observed for these analogs in competition studies performed in HKRK-B7 cells, which stably express the wild-type human P1R (FIG. 9). These results further illustrate that [Deg$^{1,3}$,BPA$^2$,Nle$^8$,Gln$^{10}$,Har$^{11}$,Ala$^{12}$, Trp$^{14}$,Arg$^{19}$,Tyr$^{21}$] PTH(1-21)NH$_2$ utilizes a novel mechanism to achieve antagonism, which is different from that used by the conventional N-terminally truncated antagonist, [Ile$^5$, Trp$^{23}$,Tyr$^{16}$]PTHrP(5-36)NH$_2$.

The pharmacologic mechanism by which [Deg$^{1,3}$,BPA$^2$, Nle$^8$,Gln$^{10}$,Har$^{11}$,Ala$^{12}$,Trp$^{14}$,Arg$^{19}$,Tyr$^{21}$]PTH(1-21)NH$_2$ and [Deg$^{1,3}$,Bpa$^2$,Gln$^{10}$,Har$^{11}$,Ala$^{12}$,Trp$^{14}$]PTH(1-14)NH$_2$ function as antagonists was investigated in FIG. 10. In this study, the effects of the antagonists at 10 mM, on the dose-response curve elicited by the agonist [Aib$^{1,3}$,Tyr$^{34}$]hPTH(1-34)NH$_2$ were examined in HKRK-B7 cells. The presence of either antagonist resulted in a rightward and parallel shift in the agonist response curve, and although true asymptotes were not attained in the curves, the results are fully consistent with a competitive, versus a non-competitive, mechanism of inhibition.

"N" versus "J" domain selectivity of P1R antagonists was investigated in COS-7 Cells (FIG. 8). cAMP antagonism assays were performed in COS-7 cells transfect with the wild-type P1R (A), or a P1R derivative (P1R-delNt) having most (residues 24-181) of the P1R N domain deleted (B). Cells were treated with the agonist [Aib$^{1,3}$,Tyr$^{34}$]hPTH(1-34) NH$_2$ ([Aib$^{1,3}$]PTH(1-34)), which utilizes both N and J domains for affinity/potency, or with [Ac$_5$c$^1$,Aib$^3$,Gln$^{10}$, Har$^{11}$,Ala$^{12}$,Trp$^{14}$]PTH(1-14)NH$_2$ ([Ac5c$^1$]PTH(1-14)), which uses only the J domain for affinity/potency, at the concentrations indicated in the key, so as to elicit half-maximum cAMP responses in the absence of antagonist (none). The analogs PTHrP(5-36) and Deg$^{1,3}$,Bpa$^2$-PTH(1-21) were added at 1×10–5 M, as indicated. On the WT receptor, PTHrP (5-36) antagonizes PTH(1-34) analog more effectively than does Deg$^{1,3}$,Bpa$^2$-PTH(1-21), but the PTH(1-21) analog antagonizes PTH(1-14), more effectively than does PTHrP (5-36). On P1R-delNt, Deg$^{1,3}$,Bpa$^2$-PTH(1-21) antagonizes either agonist, whereas PTHrP(5-36) lacks antagonist capability. Thus, PTHrP(5-36) is an N domain-selective antagonist, whereas Deg$^{1,3}$,Bpa$^2$-PTH(1-21) is a J domain-selective antagonist. The analog Deg$^{1,3}$,Bpa$^2$-PTH(1-14) behaved similarly in these assays to Deg$^{1,3}$,Bpa$^2$-PTH(1-21).

Direct structural analyses of these analogs, as free peptides, or potentially in complex with the PTH-1 receptor, could provide valuable insights into the ligand structures that allow a ligand to act as an agonist on the PTH-1 receptor. In this regard, the information derived from the data set described herein could be of use in the design of peptide mimetics for the PTH-1 receptor. Approaching this problem from the standpoint of the native PTH peptide sequence is made difficult by the conformational diversity that is possible at each position in the peptide backbone chain. The incorporation of stereochemically constrained amino acids, such as Aib, into the peptide chain, lessens this problem, as it serves to nucleate predictable peptide structures. Thus, the approach can facilitate the de novo design of peptide or nonpeptide agonists for the PTH-1 receptor. Given the recently proven utility of PTH(1-34) in treating osteoporosis (Neer, R. M., et al., *N.E.J.M.* 344: 1434-1441 (2001)), such agonists should have important medical impact.

Computer models of the interaction with native PTH are being developed (Jin, L., et al., *J. Biol. Chem.* 275: 27238-27244 (2000); Rölz, C., and Mierke, D. F., Biophysical Chemistry (2000)). The above described experiments with the truncated PTH-1 receptor, P1R-delNt, provide some insights into interactions between PTH analogs and the PTH receptors, as they demonstrate that the enhancing effects of the Aib substitutions at positions 1 and 3 are mediated through the juxtamembrane region (J domain) of the receptor containing the extracellular loops and transmembrane domains. This finding is consistent with the cumulative crosslinking and mutational data on the PTH/PTH-1 receptor interaction, which indicate that residues in the (1-14) domain of PTH interact primarily, if not exclusively, with the receptor's J domain, as opposed to its amino-terminal extracellular domain (N domain) (Bergwitz, C., et al., *J. Biol. Chem.* 271: 26469-26472 (1996); Hoare, S. R. J., et al., *J. Biol. Chem* 276: 7741-7753 (2001); Behar, V., et al., *J. Biol. Chem.* 275: 9-17 (1999); Shimizu, M., et al., *J. Biol. Chem.* 275: 19456-19460 (2000); Luck, M. D., et al., *Molecular Endocrinology* 13: 670-680(1999); Shimizu, M., et al., *J. Biol. Chem.* 275: 21836-21843 (2000); Carter, P. H., and Gardella, T. J., *Biochim. Biophys. Acta* 1538: 290-304 (2001); Gardella, T. J., et al., *Endocrinology* 132: 2024-2030 (1993); Bisello, A., et al., J. Biol. Chem. 273: 22498-22505 (1998)).

Two modes of antagonism are now recognized at the P1R. N domain inhibition (A) is utilized by most conventional P1R antagonists, such as PTHrP(5-36) and PTHrP(7-34) analogs, and is based on the derivation of binding energy primarily from interactions between the (21-34) region of the ligand and the P1R N domain. This mechanism is effective for of inhibition of N-domain-dependent agonists, such as PTH(1-34), but not for N domain-independent agonists, such as PTH(1-19). J domain inhibition (B) is utilized by the novel analogs described herein, and is based on the derivation of binding energy primarily or wholly from interactions between the (1-20) region of the ligand and the J domain of the P1R. The results also demonstrate that the antagonizing effects of the position-1, 2 and/or 3 modifications are mediated through the J domain. This mechanism is effective for inhibition of J-domain-dependent agonists, such as PTH(1-14) analogs, but not for N domain-dependent agonists, such as PTH(1-34). A J domain-selective antagonists would be useful for characterizing small-molecules that act as PTH mimetics, since such molecules are likely to bind to the J domain.

Having now fully described the present invention in some detail by way of illustration and example for purposes of clarity of understanding, it will be obvious to one of ordinary skill in the art that same can be performed by modifying or changing the invention with a wide and equivalent range of conditions, formulations and other parameters thereof, and that such modifications or changes are intended to be encompassed within the scope of the appended claims.

All publications, patents and patent applications mentioned hereinabove are herein incorporated in their entirety and by reference to the same extent as if each individual publication, patent or patent application was specifically and individually indicated to be incorporated by reference.

What is claimed is:

1. A peptide comprising the amino acid sequence:

(SEQ ID NO: 1)
X01X02X03GluIleGlnLeuX04HisX05X06X07LysX08, a fragment thereof, containing amino acids 1-9, 1-10, 1-11, 1-12, or 1-13; or
a pharmaceutically acceptable salt thereof;
wherein:
$X_{01}$ and $X_{03}$ are each an α-helix stabilizing residue,
$X_{02}$ is Trp, Bpa, or Arg,
$X_{04}$ is Met, or Nle,
$X_{05}$ is Gln, Deg, or Asn,
$X_{06}$ is Har or Leu,
$X_{07}$ is an α-helix stabilizing residue, Ala, or Gly, and
$X_{08}$ is an α-helix stabilizing residue, Trp, Tyr, or His.

2. The peptide of claim 1, wherein said α-helix stabilizing residues are selected from the group consisting of $Ac_5c$, $Ac_3c$, Deg, and Aib, or a desamino form thereof.

3. The peptide of claim 1, comprising the amino acid sequence:

(SEQ ID NO: 13)
Ac5cBpaAibGluIleGlnLeuMetHisGlnHarAlaLysTrp;

a fragment thereof, containing amino acids 1-9, 1-10, 1-11, 1-12, or 1-13; or
a pharmaceutically acceptable salt thereof.

4. The peptide of claim 1, comprising the amino acid sequence:

(SEQ ID NO: 17)
Ac5cTrpAibGluIleGlnLeuMetHisGlnHarAlaLysTrpNH2;

a fragment thereof, containing amino acids 1-9, 1-10, 1-11, 1-12, or 1-13; or
a pharmaceutically acceptable salt thereof.

5. The peptide of claim 1, comprising the amino acid sequence:

(SEQ ID NO: 18)
Ac5cBpaAibGluIleGlnLeuMetHisGlnHarAlaLysTrpNH2, a fragment thereof, containing amino acids 1-9, 1-10, 1-11, 1-12, or 1-13; or
a pharmaceutically acceptable salt thereof.

6. The peptide of claim 1, comprising the amino acid sequence:

(SEQ ID NO: 19)
Ac5cArgAibGluIleGlnLeuMetHisGlnHarAlaLysTrpNH2, a fragment thereof, containing amino acids 1-9, 1-10, 1-11, 1-12, or 1-13; or
a pharmaceutically acceptable salt thereof.

7. The peptide of claim 1, comprising the amino acid sequence:

(SEQ ID NO: 21)
DegTrpDegGluIleGlnLeuMetHisGlnHarAlaLysTrpNH2;

a fragment thereof, containing amino acids 1-9, 1-10, 1-11, 1-12, or 1-13; or
a pharmaceutically acceptable salt thereof.

8. The peptide of claim 1, comprising the amino acid sequence:

(SEQ ID NO: 22)
DegBpaDegGluIleGlnLeuMetHisGlnHarAlaLysTrpNH2;

a fragment thereof, containing amino acids 1-9, 1-10, 1-11, 1-12, or 1-13; or
a pharmaceutically acceptable salt thereof.

9. The peptide of claim 1, comprising the amino acid sequence:

(SEQ ID NO: 23)
Ac5cTrpAibGluIleGlnLeuNleHisGlnHarAlaLysTyrNH2;

a fragment thereof, containing amino acids 1-9, 1-10, 1-11, 1-12, or 1-13; or
a pharmaceutically acceptable salt thereof.

10. The peptide of claim 1, comprising the amino acid sequence:

(SEQ ID NO: 24)
Ac5cBpaAibGluIleGlnLeuNleHisGlnHarAlaLysTyrNH2;

a fragment thereof, containing amino acids 1-9, 1-10, 1-11, 1-12, or 1-13; or
a pharmaceutically acceptable salt thereof.

11. The peptide of claim 1, wherein said peptide is labeled.

12. The peptide of claim 11, wherein said peptide is labeled with a fluorescent label.

13. The peptide of claim 11, wherein said peptide is labeled with a chemiluminescent label.

14. The peptide of claim 11, wherein said peptide is labeled with a bioluminescent label.

15. The peptide of claim 11, wherein said peptide is labeled with a radioactive label.

16. The peptide of claim 15, wherein said peptide is labeled with $^{125}I$.

17. The peptide of claim 15, wherein said peptide is labeled with $^{99m}Tc$.

18. A competition binding assay to identify a PTH receptor ligand, which comprises contacting said receptor with the labeled peptide of claim 11 and a candidate receptor ligand, and measuring the label bound to the receptor.

19. A competition binding assay to analyze a PTH receptor ligand, which comprises contacting said receptor, or fragments or derivatives thereof, with the labeled peptide of claim 11 and a candidate receptor ligand, and measuring the label bound to the receptor.

20. A pharmaceutical composition comprising the peptide of claim 1, and a pharmaceutically acceptable carrier.

21. A method of treating hypercalcemia, said method comprising administering to a subject in need thereof an effective amount of a peptide of claim 1.

22. A method of treating hypercalcemia, said method comprising administering to a subject in need thereof an effective amount of a composition comprising a peptide of claim 1 and a pharmaceutically acceptable carrier.

23. The method of claim 22, wherein said condition to be treated is malignant hypercalcemia.

24. The method of claim 21, wherein said effective amount of said peptide for reducing activity or production of PTH or PTHrP is from about 0.01 µg/kg/day to about 1.0 µg/kg/day.

25. The method of claim 21, wherein the method of administration is parenteral.

26. The method of claim 21, wherein the method of administration is subcutaneous.

27. The method of claim 21, wherein the method of administration is nasal insufflation.

28. A method of making the peptide of claim 1, wherein said peptide is synthesized by solid phase synthesis.

29. The method of making the peptide of claim 1, wherein said peptide is protected by FMOC.

30. The peptide of claim 1 consisting of said amino acid sequence; a fragment thereof containing amino acids 1-9, 1-10, 1-11, 1-12, or 1-13; or a pharmaceutically acceptable salt thereof.

31. The peptide of claim 30 consisting of said amino acid sequence, or a pharmaceutically acceptable salt thereof.

32. The peptide of claim 3 consisting of the amino acid sequence: $Ac_5cBpaAibGluIleGlnLeuMetHisGlnHarAlaLysTrp$ (SEQ ID NO:13), or a pharmaceutically acceptable salt thereof.

33. The peptide of claim 4 consisting of the amino acid sequence: $Ac_5cTrpAibGluIleGlnLeuMetHisGlnHarAlaLysTrpNH_2$ (SEQ ID NO:17), or a pharmaceutically acceptable salt thereof.

34. The peptide of claim 5 consisting of the amino acid sequence: $Ac_5cBpaAibGluIleGlnLeuMetHisGlnHarAlaLysTrpNH_2$ (SEQ ID NO:18) or a pharmaceutically acceptable salt thereof.

35. The peptide of claim 6 consisting of the amino acid sequence: $Ac_5cArgAibGluIleGlnLeuMetHisGlnHarAlaLysTrpNH_2$ (SEQ ID NO:19), or a pharmaceutically acceptable salt thereof.

36. The peptide of claim 7 consisting of the amino acid sequence: $DegTrpDegGluIleGlnLeuMetHisGlnHarAlaLysTrpNH_2$ (SEQ ID NO:21), or a pharmaceutically acceptable salt thereof.

37. The peptide of claim 8 consisting of the amino acid sequence: $DegTrpDegGluIleGlnLeuNleHisGlnHarAlaLysTrpNH_2$ (SEQ ID NO:22), or a pharmaceutically acceptable salt thereof.

38. The peptide of claim 9 consisting of amino acid sequence: $Ac_5cTrpAibGluIleGlnLeuNleHisGlnHarAlaLysTyrNH_2$ (SEQ ID NO:23), or a pharmaceutically acceptable salt thereof.

39. The peptide of claim 10 consisting of amino acid sequence: $Ac_5cBpaAibGluIleGlnLeuNleHisGlnHarAlaLysTyrNH_2$ (SEQ ID NO:24), or a pharmaceutically acceptable salt thereof.

\* \* \* \* \*

UNITED STATES PATENT AND TRADEMARK OFFICE
CERTIFICATE OF CORRECTION

| | | |
|---|---|---|
| PATENT NO. | : 7,910,544 B2 | Page 1 of 1 |
| APPLICATION NO. | : 10/564744 | |
| DATED | : March 22, 2011 | |
| INVENTOR(S) | : Gardella et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 970 days.

Signed and Sealed this
Twenty-third Day of August, 2011

David J. Kappos
*Director of the United States Patent and Trademark Office*

UNITED STATES PATENT AND TRADEMARK OFFICE
CERTIFICATE OF CORRECTION

PATENT NO. : 7,910,544 B2
APPLICATION NO. : 10/564744
DATED : March 22, 2011
INVENTOR(S) : Gardella et al.

It is certified that error appears in the above-identified patent and that said Letters Patent is hereby corrected as shown below:

On Title Page 2, Item (56) under OTHER PUBLICATIONS, in Creighton et al., replace "NewYork" with --New York--;

Item (56) under OTHER PUBLICATIONS, in Goud et al., replace "Horrnone" with --Hormone--.

On Title Page 3, Item (56) under OTHER PUBLICATIONS, in Azarani et al., replace "Acticate" with --Activate--.

On Title Page 8, Item (56) under OTHER PUBLICATIONS, in Sunyaev et al, replace "Structrual" with --Structural--.

Column 2, Line 2, replace "hypercalcema" with --hypercalcemia--.

Column 3, Line 55, replace "$X_{01}X_{02}X_{03}GluIleGinLeuX_{04}HisX_{05}X_{06}X_{07}LysX_{08}$" with --$X_{01}X_{02}X_{03}GluIleGlnLeuX_{04}HisX_{05}X_{06}X_{07}LysX_{08}$--;

Line 57, replace "e.g., $Ac_3c$," with --e.g., $Ac_5c$,--;

Line 57, replace "form of $Ac_3c$" with --form of $Ac_5c$--;

Line 66, replace "$X_{01}X_{02}X_{03}GluIleGlnLeuX_{04}H$ is $X_{05}X_{06}X_{07}LysX_{08}$" with --$X_{01}X_{02}X_{03}GluIleGlnLeuX_{04}HisX_{05}X_{06}X_{07}LysX_{08}$--.

Column 4, Line 1, replace "e.g., $Ac_3c$," with --e.g., $Ac_5c$,--;

Line 50, replace "flourescent" with --fluorescent--;

Signed and Sealed this
Twenty-second Day of May, 2012

David J. Kappos
*Director of the United States Patent and Trademark Office*

CERTIFICATE OF CORRECTION (continued)
U.S. Pat. No. 7,910,544 B2

Page 2 of 2

Column 4, Line 55, replace "Ac5cBpaAibGluIleGlnLeuMetHisGlnHarAlaLysTrp" with --Ac$_5$cBpaAibGluIleGlnLeuMetHisGlnHarAlaLysTrp--.

Column 5, Line 36, replace "flourescent" with --fluorescent--;

Line 52, replace "(Ac$_3$c)." with --(Ac$_5$c).--.

Column 6, Line 53, replace "hpTH" with --hPTH--;

Line 60, replace "1×10-5 M" with --1×10$^{-5}$ M--.

Column 7, Line 16, replace "1×10-5 M" with --1×10$^{-5}$ M--.

Column 9, Line 61, replace "AlaValSerGluIleGluMetHisAsn-" with --AlaValSerGluIleGlnLeuMetHisAsn- --.

Column 12, Lines 5-6, replace "acylcamitines" with --acylcarnitines--.

Column 13, Line 23, replace "whether" with --Whether--.

Column 14, Line 9, replace "HBTU/HOBt/DIEBA" with --HBTU/HOBt/DIEA--;

Line 35, replace "Co$_2$" with --CO$_2$--;

Line 53, replace "Delbecco's" with --Dulbecco's--.

Column 15, Line 60, replace "Deg$_{1,3}$-substituted" with --Deg$^{1,3}$-substituted--.

Column 16, Line 56, replace "1×10-5 M" with --1×10$^{-5}$ M--.

Column 47, Line 5, remove "(SEQ ID NO: 1)";

Line 45, replace "Ac$_5$cBpaAibGluIleGlnLeuMetHisGlnHarAlaLysTrpNH$_2$," with --Ac$_5$cBpaAibGluIleGlnLeuMetHisGlnHarAlaLysTrpNH$_2$;--;

Line 54, replace "Ac$_5$cArgAibGluIleGlnLeuMetHisGlnHarAlaLysTrpNH$_2$," with --Ac$_5$cArgAibGluIleGlnLeuMetHisGlnHarAlaLysTrpNH$_2$;--.

Column 50, Line 12, replace "DegTrpDegGluIleGlnLeuNleHisGlnHarAlaLysTrpNH$_2$" with --DegBpaDegGluIleGlnLeuMetHisGlnHarAlaLysTrpNH$_2$--;

Line 22, replace "Ac$_5$cBpaAibGluIleGlnLeuNleHisG1nHarAlaLysTyrNH$_2$" with --Ac$_5$cBpaAibGluIleGlnLeuNleHisGlnHarAlaLysTyrNH$_2$--.

SEQUENCE LISTING

```
<160> NUMBER OF SEQ ID NOS: 32

<210> SEQ ID NO 1
<211> LENGTH: 14
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is an Alpha-Helix Stabilizing Residue
<220> FEATURE:
<221> NAME/KEY: misc_feature
<222> LOCATION: (2)..(2)
<223> OTHER INFORMATION: X is Trp, Bpa, Arg or Val
<220> FEATURE:
<221> NAME/KEY: misc_feature
<222> LOCATION: (3)..(3)
<223> OTHER INFORMATION: X is an Alpha-Helix Stabilizing Residue
<220> FEATURE:
<221> NAME/KEY: misc_feature
<222> LOCATION: (8)..(8)
<223> OTHER INFORMATION: X is Met or Nle
<220> FEATURE:
<221> NAME/KEY: misc_feature
<222> LOCATION: (10)..(10)
<223> OTHER INFORMATION: X is Gln, Deg  or Asn
<220> FEATURE:
```

```
<221> NAME/KEY: misc_feature
<222> LOCATION: (11)..(11)
<223> OTHER INFORMATION: X is Har or Leu
<220> FEATURE:
<221> NAME/KEY: misc_feature
<222> LOCATION: (12)..(12)
<223> OTHER INFORMATION: X is an Alpha-Helix Stabilizing Residue, Ala or
      Gly
<220> FEATURE:
<221> NAME/KEY: misc_feature
<222> LOCATION: (14)..(14)
<223> OTHER INFORMATION: X is an Alpha-Helix Stabilizing Residue, Trp,
      Tyr or His

<400> SEQUENCE: 1

Xaa Xaa Xaa Glu Ile Gln Leu Xaa His Xaa Xaa Xaa Lys Xaa
1               5                   10

<210> SEQ ID NO 2
<211> LENGTH: 13
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is an Alpha-Helix Stabilizing Residue
<220> FEATURE:
<221> NAME/KEY: misc_feature
<222> LOCATION: (2)..(2)
<223> OTHER INFORMATION: X is Trp, Bpa, Arg or Val
<220> FEATURE:
<221> NAME/KEY: misc_feature
<222> LOCATION: (3)..(3)
<223> OTHER INFORMATION: X is an Alpha-Helix Stabilizing Residue
<220> FEATURE:
<221> NAME/KEY: misc_feature
<222> LOCATION: (8)..(8)
<223> OTHER INFORMATION: X is Met or Nle
<220> FEATURE:
<221> NAME/KEY: misc_feature
<222> LOCATION: (10)..(10)
<223> OTHER INFORMATION: X is Gln, Deg or Asn
<220> FEATURE:
<221> NAME/KEY: misc_feature
<222> LOCATION: (11)..(11)
<223> OTHER INFORMATION: X is Har or Leu
<220> FEATURE:
<221> NAME/KEY: misc_feature
<222> LOCATION: (12)..(12)
<223> OTHER INFORMATION: X is an Alpha-Helix Stabilizing Residue, Ala or
      Gly

<400> SEQUENCE: 2

Xaa Xaa Xaa Glu Ile Gln Leu Xaa His Xaa Xaa Xaa Lys
1               5                   10

<210> SEQ ID NO 3
<211> LENGTH: 12
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is an Alpha-Helix Stabilizing Residue
<220> FEATURE:
<221> NAME/KEY: misc_feature
<222> LOCATION: (2)..(2)
<223> OTHER INFORMATION: X is Trp, Bpa, Arg or Val
<220> FEATURE:
<221> NAME/KEY: misc_feature
<222> LOCATION: (3)..(3)
<223> OTHER INFORMATION: X is an Alpha-Helix Stabilizing Residue
```

```
<220> FEATURE:
<221> NAME/KEY: misc_feature
<222> LOCATION: (8)..(8)
<223> OTHER INFORMATION: X is Met or Nle
<220> FEATURE:
<221> NAME/KEY: misc_feature
<222> LOCATION: (10)..(10)
<223> OTHER INFORMATION: X is Gln, Deg  or Asn
<220> FEATURE:
<221> NAME/KEY: misc_feature
<222> LOCATION: (11)..(11)
<223> OTHER INFORMATION: X is Har or Leu
<220> FEATURE:
<221> NAME/KEY: misc_feature
<222> LOCATION: (12)..(12)
<223> OTHER INFORMATION: X is an Alpha-Helix Stabilizing Residue, Ala or
      Gly

<400> SEQUENCE: 3

Xaa Xaa Xaa Glu Ile Gln Leu Xaa His Xaa Xaa Xaa
1               5                   10

<210> SEQ ID NO 4
<211> LENGTH: 11
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is an Alpha-Helix Stabilizing Residue
<220> FEATURE:
<221> NAME/KEY: misc_feature
<222> LOCATION: (2)..(2)
<223> OTHER INFORMATION: X is Trp, Bpa, Arg or Val
<220> FEATURE:
<221> NAME/KEY: misc_feature
<222> LOCATION: (3)..(3)
<223> OTHER INFORMATION: X is an Alpha-Helix Stabilizing Residue
<220> FEATURE:
<221> NAME/KEY: misc_feature
<222> LOCATION: (8)..(8)
<223> OTHER INFORMATION: X is Met or Nle
<220> FEATURE:
<221> NAME/KEY: misc_feature
<222> LOCATION: (10)..(10)
<223> OTHER INFORMATION: X is Gln, Deg  or Asn
<220> FEATURE:
<221> NAME/KEY: misc_feature
<222> LOCATION: (11)..(11)
<223> OTHER INFORMATION: X is Har or Leu

<400> SEQUENCE: 4

Xaa Xaa Xaa Glu Ile Gln Leu Xaa His Xaa Xaa
1               5                   10

<210> SEQ ID NO 5
<211> LENGTH: 10
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is an Alpha-Helix Stabilizing Residue
<220> FEATURE:
<221> NAME/KEY: misc_feature
<222> LOCATION: (2)..(2)
<223> OTHER INFORMATION: X is Trp, Bpa, Arg or Val
<220> FEATURE:
<221> NAME/KEY: misc_feature
<222> LOCATION: (3)..(3)
<223> OTHER INFORMATION: X is an Alpha-Helix Stabilizing Residue
<220> FEATURE:
```

```
<221> NAME/KEY: misc_feature
<222> LOCATION: (8)..(8)
<223> OTHER INFORMATION: X is Met or Nle
<220> FEATURE:
<221> NAME/KEY: misc_feature
<222> LOCATION: (10)..(10)
<223> OTHER INFORMATION: X is Gln, Deg  or Asn

<400> SEQUENCE: 5

Xaa Xaa Xaa Glu Ile Gln Leu Xaa His Xaa
1               5                   10

<210> SEQ ID NO 6
<211> LENGTH: 21
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is an Alpha-Helix Stabilizing Residue
<220> FEATURE:
<221> NAME/KEY: misc_feature
<222> LOCATION: (2)..(2)
<223> OTHER INFORMATION: X is Bpa
<220> FEATURE:
<221> NAME/KEY: misc_feature
<222> LOCATION: (3)..(3)
<223> OTHER INFORMATION: X is an Alpha-Helix Stabilizing Residue
<220> FEATURE:
<221> NAME/KEY: misc_feature
<222> LOCATION: (8)..(8)
<223> OTHER INFORMATION: X is Aib, Gln, Deg  or Asn
<220> FEATURE:
<221> NAME/KEY: misc_feature
<222> LOCATION: (10)..(10)
<223> OTHER INFORMATION: X is Met or Nle
<220> FEATURE:
<221> NAME/KEY: misc_feature
<222> LOCATION: (11)..(11)
<223> OTHER INFORMATION: X is Har or Leu
<220> FEATURE:
<221> NAME/KEY: misc_feature
<222> LOCATION: (12)..(12)
<223> OTHER INFORMATION: X is an Alpha-Helix Stabilizing Residue, Ala or
      Gly
<220> FEATURE:
<221> NAME/KEY: misc_feature
<222> LOCATION: (14)..(14)
<223> OTHER INFORMATION: X is an Alpha-Helix Stabilizing Residue, Trp or
      His
<220> FEATURE:
<221> NAME/KEY: misc_feature
<222> LOCATION: (19)..(19)
<223> OTHER INFORMATION: X is an Alpha-Helix Stabilizing Residue, Lys,
      Arg or Glu
<220> FEATURE:
<221> NAME/KEY: misc_feature
<222> LOCATION: (21)..(21)
<223> OTHER INFORMATION: X is Tyr or Met

<400> SEQUENCE: 6

Xaa Xaa Xaa Glu Ile Gln Leu Xaa His Xaa Xaa Xaa Lys Xaa Leu Ala
1               5                   10                  15

Ser Val Xaa Arg Xaa
            20

<210> SEQ ID NO 7
<211> LENGTH: 20
<212> TYPE: PRT
<213> ORGANISM: Artificial sequence
<220> FEATURE:
<223> OTHER INFORMATION: PTH Peptide
<220> FEATURE:
```

```
<221> NAME/KEY: misc_feature
<222> LOCATION: (1)..(1)
<223> OTHER INFORMATION: X is an Alpha-Helix Stabilizing Residue
<220> FEATURE:
<221> NAME/KEY: misc_feature
<222> LOCATION: (2)..(2)
<223> OTHER INFORMATION: X is Bpa
<220> FEATURE:
<221> NAME/KEY: misc_feature
<222> LOCATION: (3)..(3)
<223> OTHER INFORMATION: X is an Alpha-Helix Stabilizing Residue
<220> FEATURE:
<221> NAME/KEY: misc_feature
<222> LOCATION: (8)..(8)
<223> OTHER INFORMATION: X is Aib, Gln, Deg  or Asn
<220> FEATURE:
<221> NAME/KEY: misc_feature
<222> LOCATION: (10)..(10)
<223> OTHER INFORMATION: X is Met or Nle
<220> FEATURE:
<221> NAME/KEY: misc_feature
<222> LOCATION: (11)..(11)
<223> OTHER INFORMATION: X is Har or Leu
<220> FEATURE:
<221> NAME/KEY: misc_feature
<222> LOCATION: (12)..(12)
<223> OTHER INFORMATION: X is an Alpha-Helix Stabilizing Residue, Ala or
      Gly
<220> FEATURE:
<221> NAME/KEY: misc_feature
<222> LOCATION: (14)..(14)
<223> OTHER INFORMATION: X is an Alpha-Helix Stabilizing Residue, Trp or
      His
<220> FEATURE:
<221> NAME/KEY: misc_feature
<222> LOCATION: (19)..(19)
<223> OTHER INFORMATION: X is an Alpha-Helix Stabilizing Residue, Lys,
      Arg or Glu

<400> SEQUENCE: 7

Xaa Xaa Xaa Glu Ile Gln Leu Xaa His Xaa Xaa Xaa Lys Xaa Leu Ala
1               5                   10                  15

Ser Val Xaa Arg
            20

<210> SEQ ID NO 8
<211> LENGTH: 19
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is an Alpha-Helix Stabilizing Residue
<220> FEATURE:
<221> NAME/KEY: misc_feature
<222> LOCATION: (2)..(2)
<223> OTHER INFORMATION: X is Bpa
<220> FEATURE:
<221> NAME/KEY: misc_feature
<222> LOCATION: (3)..(3)
<223> OTHER INFORMATION: X is an Alpha-Helix Stabilizing Residue
<220> FEATURE:
<221> NAME/KEY: misc_feature
<222> LOCATION: (8)..(8)
<223> OTHER INFORMATION: X is Aib, Gln, Deg  or Asn
<220> FEATURE:
<221> NAME/KEY: misc_feature
<222> LOCATION: (10)..(10)
<223> OTHER INFORMATION: X is Met or Nle
<220> FEATURE:
<221> NAME/KEY: misc_feature
<222> LOCATION: (11)..(11)
<223> OTHER INFORMATION: X is Har or Leu
<220> FEATURE:
<221> NAME/KEY: misc_feature
```

-continued

```
<222> LOCATION: (12)..(12)
<223> OTHER INFORMATION: X is an Alpha-Helix Stabilizing Residue, Ala or
      Gly
<220> FEATURE:
<221> NAME/KEY: misc_feature
<222> LOCATION: (14)..(14)
<223> OTHER INFORMATION: X is an Alpha-Helix Stabilizing Residue, Trp or
      His
<220> FEATURE:
<221> NAME/KEY: misc_feature
<222> LOCATION: (19)..(19)
<223> OTHER INFORMATION: X is an Alpha-Helix Stabilizing Residue, Lys,
      Arg or Glu

<400> SEQUENCE: 8

Xaa Xaa Xaa Glu Ile Gln Leu Xaa His Xaa Xaa Xaa Lys Xaa Leu Ala
1               5                   10                  15

Ser Val Xaa

<210> SEQ ID NO 9
<211> LENGTH: 18
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is an Alpha-Helix Stabilizing Residue
<220> FEATURE:
<221> NAME/KEY: misc_feature
<222> LOCATION: (2)..(2)
<223> OTHER INFORMATION: X is Bpa
<220> FEATURE:
<221> NAME/KEY: misc_feature
<222> LOCATION: (3)..(3)
<223> OTHER INFORMATION: X is an Alpha-Helix Stabilizing Residue
<220> FEATURE:
<221> NAME/KEY: misc_feature
<222> LOCATION: (8)..(8)
<223> OTHER INFORMATION: X is Aib, Gln, Deg  or Asn
<220> FEATURE:
<221> NAME/KEY: misc_feature
<222> LOCATION: (10)..(10)
<223> OTHER INFORMATION: X is Met or Nle
<220> FEATURE:
<221> NAME/KEY: misc_feature
<222> LOCATION: (11)..(11)
<223> OTHER INFORMATION: X is Har or Leu
<220> FEATURE:
<221> NAME/KEY: misc_feature
<222> LOCATION: (12)..(12)
<223> OTHER INFORMATION: X is an Alpha-Helix Stabilizing Residue, Ala or
      Gly
<220> FEATURE:
<221> NAME/KEY: misc_feature
<222> LOCATION: (14)..(14)
<223> OTHER INFORMATION: X is an Alpha-Helix Stabilizing Residue, Trp or
      His

<400> SEQUENCE: 9

Xaa Xaa Xaa Glu Ile Gln Leu Xaa His Xaa Xaa Xaa Lys Xaa Leu Ala
1               5                   10                  15

Ser Val

<210> SEQ ID NO 10
<211> LENGTH: 17
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
```

```
<223> OTHER INFORMATION: X is an Alpha-Helix Stabilizing Residue
<220> FEATURE:
<221> NAME/KEY: misc_feature
<222> LOCATION: (2)..(2)
<223> OTHER INFORMATION: X is Bpa
<220> FEATURE:
<221> NAME/KEY: misc_feature
<222> LOCATION: (3)..(3)
<223> OTHER INFORMATION: X is an Alpha-Helix Stabilizing Residue
<220> FEATURE:
<221> NAME/KEY: misc_feature
<222> LOCATION: (8)..(8)
<223> OTHER INFORMATION: X is Aib, Gln, Deg  or Asn
<220> FEATURE:
<221> NAME/KEY: misc_feature
<222> LOCATION: (10)..(10)
<223> OTHER INFORMATION: X is Met or Nle
<220> FEATURE:
<221> NAME/KEY: misc_feature
<222> LOCATION: (11)..(11)
<223> OTHER INFORMATION: X is Har or Leu
<220> FEATURE:
<221> NAME/KEY: misc_feature
<222> LOCATION: (12)..(12)
<223> OTHER INFORMATION: X is an Alpha-Helix Stabilizing Residue, Ala or
      Gly
<220> FEATURE:
<221> NAME/KEY: misc_feature
<222> LOCATION: (14)..(14)
<223> OTHER INFORMATION: X is an Alpha-Helix Stabilizing Residue, Trp or
      His

<400> SEQUENCE: 10

Xaa Xaa Xaa Glu Ile Gln Leu Xaa His Xaa Xaa Xaa Lys Xaa Leu Ala
1               5                   10                  15

Ser

<210> SEQ ID NO 11
<211> LENGTH: 16
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is an Alpha-Helix Stabilizing Residue
<220> FEATURE:
<221> NAME/KEY: misc_feature
<222> LOCATION: (2)..(2)
<223> OTHER INFORMATION: X is Bpa
<220> FEATURE:
<221> NAME/KEY: misc_feature
<222> LOCATION: (3)..(3)
<223> OTHER INFORMATION: X is an Alpha-Helix Stabilizing Residue
<220> FEATURE:
<221> NAME/KEY: misc_feature
<222> LOCATION: (8)..(8)
<223> OTHER INFORMATION: X is Aib, Gln, Deg  or Asn
<220> FEATURE:
<221> NAME/KEY: misc_feature
<222> LOCATION: (10)..(10)
<223> OTHER INFORMATION: X is Met or Nle
<220> FEATURE:
<221> NAME/KEY: misc_feature
<222> LOCATION: (11)..(11)
<223> OTHER INFORMATION: X is Har or Leu
<220> FEATURE:
<221> NAME/KEY: misc_feature
<222> LOCATION: (12)..(12)
<223> OTHER INFORMATION: X is an Alpha-Helix Stabilizing Residue, Ala or
      Gly
<220> FEATURE:
<221> NAME/KEY: misc_feature
<222> LOCATION: (14)..(14)
<223> OTHER INFORMATION: X is an Alpha-Helix Stabilizing Residue, Trp or
      His
```

<400> SEQUENCE: 11

Xaa Xaa Xaa Glu Ile Gln Leu Xaa His Xaa Xaa Xaa Lys Xaa Leu Ala
1               5                   10                  15

<210> SEQ ID NO 12
<211> LENGTH: 15
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is an Alpha-Helix Stabilizing Residue
<220> FEATURE:
<221> NAME/KEY: misc_feature
<222> LOCATION: (2)..(2)
<223> OTHER INFORMATION: X is Bpa
<220> FEATURE:
<221> NAME/KEY: misc_feature
<222> LOCATION: (3)..(3)
<223> OTHER INFORMATION: X is an Alpha-Helix Stabilizing Residue
<220> FEATURE:
<221> NAME/KEY: misc_feature
<222> LOCATION: (8)..(8)
<223> OTHER INFORMATION: X is Aib, Gln, Deg or Asn
<220> FEATURE:
<221> NAME/KEY: misc_feature
<222> LOCATION: (10)..(10)
<223> OTHER INFORMATION: X is Met or Nle
<220> FEATURE:
<221> NAME/KEY: misc_feature
<222> LOCATION: (11)..(11)
<223> OTHER INFORMATION: X is Har or Leu
<220> FEATURE:
<221> NAME/KEY: misc_feature
<222> LOCATION: (12)..(12)
<223> OTHER INFORMATION: X is an Alpha-Helix Stabilizing Residue, Ala or
      Gly
<220> FEATURE:
<221> NAME/KEY: misc_feature
<222> LOCATION: (14)..(14)
<223> OTHER INFORMATION: X is an Alpha-Helix Stabilizing Residue, Trp or
      His

<400> SEQUENCE: 12

Xaa Xaa Xaa Glu Ile Gln Leu Xaa His Xaa Xaa Xaa Lys Xaa Leu
1               5                   10                  15

<210> SEQ ID NO 13
<211> LENGTH: 14
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is Ac5c
<220> FEATURE:
<221> NAME/KEY: misc_feature
<222> LOCATION: (2)..(2)
<223> OTHER INFORMATION: X is Bpa
<220> FEATURE:
<221> NAME/KEY: misc_feature
<222> LOCATION: (3)..(3)
<223> OTHER INFORMATION: X is Aib
<220> FEATURE:
<221> NAME/KEY: misc_feature
<222> LOCATION: (11)..(11)
<223> OTHER INFORMATION: X is Har

<400> SEQUENCE: 13

Xaa Xaa Xaa Glu Ile Gln Leu Met His Gln Xaa Ala Lys Trp

<210> SEQ ID NO 14
<211> LENGTH: 15
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is Ac5c
<220> FEATURE:
<221> NAME/KEY: misc_feature
<222> LOCATION: (3)..(3)
<223> OTHER INFORMATION: X is Aib
<220> FEATURE:
<221> NAME/KEY: misc_feature
<222> LOCATION: (11)..(11)
<223> OTHER INFORMATION: X is Har
<220> FEATURE:
<221> NAME/KEY: misc_feature
<222> LOCATION: (15)..(15)
<223> OTHER INFORMATION: X is an Amino Group

<400> SEQUENCE: 14

Xaa Val Xaa Glu Ile Gln Leu Met His Gln Xaa Ala Lys Trp Xaa
1               5                   10                  15

<210> SEQ ID NO 15
<211> LENGTH: 16
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is (desNH2)
<220> FEATURE:
<221> NAME/KEY: misc_feature
<222> LOCATION: (2)..(2)
<223> OTHER INFORMATION: X is Ac5c
<220> FEATURE:
<221> NAME/KEY: misc_feature
<222> LOCATION: (4)..(4)
<223> OTHER INFORMATION: X is Aib
<220> FEATURE:
<221> NAME/KEY: misc_feature
<222> LOCATION: (12)..(12)
<223> OTHER INFORMATION: X is Har
<220> FEATURE:
<221> NAME/KEY: misc_feature
<222> LOCATION: (16)..(16)
<223> OTHER INFORMATION: X is an Amino Group

<400> SEQUENCE: 15

Xaa Xaa Val Xaa Glu Ile Gln Leu Met His Gln Xaa Ala Lys Trp Xaa
1               5                   10                  15

<210> SEQ ID NO 16
<211> LENGTH: 16
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is (desNH2)
<220> FEATURE:
<221> NAME/KEY: misc_feature
<222> LOCATION: (2)..(2)
<223> OTHER INFORMATION: X is Aib
<220> FEATURE:

```
<221> NAME/KEY: misc_feature
<222> LOCATION: (4)..(4)
<223> OTHER INFORMATION: X is Aib
<220> FEATURE:
<221> NAME/KEY: misc_feature
<222> LOCATION: (12)..(12)
<223> OTHER INFORMATION: X is Har
<220> FEATURE:
<221> NAME/KEY: misc_feature
<222> LOCATION: (16)..(16)
<223> OTHER INFORMATION: X is an Amino Group

<400> SEQUENCE: 16

Xaa Xaa Val Xaa Glu Ile Gln Leu Met His Gln Xaa Ala Lys Trp Xaa
1               5                   10                  15

<210> SEQ ID NO 17
<211> LENGTH: 15
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is Ac5c
<220> FEATURE:
<221> NAME/KEY: misc_feature
<222> LOCATION: (3)..(3)
<223> OTHER INFORMATION: X is Aib
<220> FEATURE:
<221> NAME/KEY: misc_feature
<222> LOCATION: (11)..(11)
<223> OTHER INFORMATION: X is Har
<220> FEATURE:
<221> NAME/KEY: misc_feature
<222> LOCATION: (15)..(15)
<223> OTHER INFORMATION: X is an Amino Group

<400> SEQUENCE: 17

Xaa Trp Xaa Glu Ile Gln Leu Met His Gln Xaa Ala Lys Trp Xaa
1               5                   10                  15

<210> SEQ ID NO 18
<211> LENGTH: 15
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is Ac5c
<220> FEATURE:
<221> NAME/KEY: misc_feature
<222> LOCATION: (2)..(2)
<223> OTHER INFORMATION: X is Bpa
<220> FEATURE:
<221> NAME/KEY: misc_feature
<222> LOCATION: (3)..(3)
<223> OTHER INFORMATION: X is Aib
<220> FEATURE:
<221> NAME/KEY: misc_feature
<222> LOCATION: (11)..(11)
<223> OTHER INFORMATION: X is Har
<220> FEATURE:
<221> NAME/KEY: misc_feature
<222> LOCATION: (15)..(15)
<223> OTHER INFORMATION: X is an Amino Group

<400> SEQUENCE: 18

Xaa Xaa Xaa Glu Ile Gln Leu Met His Gln Xaa Ala Lys Trp Xaa
1               5                   10                  15
```

```
<210> SEQ ID NO 19
<211> LENGTH: 15
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is Ac5c
<220> FEATURE:
<221> NAME/KEY: misc_feature
<222> LOCATION: (3)..(3)
<223> OTHER INFORMATION: X is Aib
<220> FEATURE:
<221> NAME/KEY: misc_feature
<222> LOCATION: (11)..(11)
<223> OTHER INFORMATION: X is Har
<220> FEATURE:
<221> NAME/KEY: misc_feature
<222> LOCATION: (15)..(15)
<223> OTHER INFORMATION: X is an Amino Group

<400> SEQUENCE: 19

Xaa Arg Xaa Glu Ile Gln Leu Met His Gln Xaa Ala Lys Trp Xaa
1               5                   10                  15

<210> SEQ ID NO 20
<211> LENGTH: 15
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is Deg
<220> FEATURE:
<221> NAME/KEY: misc_feature
<222> LOCATION: (3)..(3)
<223> OTHER INFORMATION: X is Deg
<220> FEATURE:
<221> NAME/KEY: misc_feature
<222> LOCATION: (11)..(11)
<223> OTHER INFORMATION: X is Har
<220> FEATURE:
<221> NAME/KEY: misc_feature
<222> LOCATION: (15)..(15)
<223> OTHER INFORMATION: X is an Amino Group

<400> SEQUENCE: 20

Xaa Val Xaa Glu Ile Gln Leu Met His Gln Xaa Ala Lys Trp Xaa
1               5                   10                  15

<210> SEQ ID NO 21
<211> LENGTH: 15
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is Deg
<220> FEATURE:
<221> NAME/KEY: misc_feature
<222> LOCATION: (3)..(3)
<223> OTHER INFORMATION: X is Deg
<220> FEATURE:
<221> NAME/KEY: misc_feature
<222> LOCATION: (11)..(11)
<223> OTHER INFORMATION: X is Har
<220> FEATURE:
<221> NAME/KEY: misc_feature
<222> LOCATION: (15)..(15)
<223> OTHER INFORMATION: X is an Amino Group
```

```
<400> SEQUENCE: 21

Xaa Trp Xaa Glu Ile Gln Leu Met His Gln Xaa Ala Lys Trp Xaa
1               5                   10                  15

<210> SEQ ID NO 22
<211> LENGTH: 15
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is Deg
<220> FEATURE:
<221> NAME/KEY: misc_feature
<222> LOCATION: (2)..(2)
<223> OTHER INFORMATION: X is Bpa
<220> FEATURE:
<221> NAME/KEY: misc_feature
<222> LOCATION: (3)..(3)
<223> OTHER INFORMATION: X is Deg
<220> FEATURE:
<221> NAME/KEY: misc_feature
<222> LOCATION: (11)..(11)
<223> OTHER INFORMATION: X is Har
<220> FEATURE:
<221> NAME/KEY: misc_feature
<222> LOCATION: (15)..(15)
<223> OTHER INFORMATION: X is an Amino Group

<400> SEQUENCE: 22

Xaa Xaa Xaa Glu Ile Gln Leu Met His Gln Xaa Ala Lys Trp Xaa
1               5                   10                  15

<210> SEQ ID NO 23
<211> LENGTH: 15
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is Ac5c
<220> FEATURE:
<221> NAME/KEY: misc_feature
<222> LOCATION: (3)..(3)
<223> OTHER INFORMATION: X is Aib
<220> FEATURE:
<221> NAME/KEY: misc_feature
<222> LOCATION: (8)..(8)
<223> OTHER INFORMATION: X is Nle
<220> FEATURE:
<221> NAME/KEY: misc_feature
<222> LOCATION: (11)..(11)
<223> OTHER INFORMATION: X is Har
<220> FEATURE:
<221> NAME/KEY: misc_feature
<222> LOCATION: (15)..(15)
<223> OTHER INFORMATION: X is an Amino Group

<400> SEQUENCE: 23

Xaa Trp Xaa Glu Ile Gln Leu Xaa His Gln Xaa Ala Lys Tyr Xaa
1               5                   10                  15

<210> SEQ ID NO 24
<211> LENGTH: 15
<212> TYPE: PRT
<213> ORGANISM: Artificial sequence
<220> FEATURE:
<223> OTHER INFORMATION: PTH Peptide
<220> FEATURE:
```

```
<221> NAME/KEY: misc_feature
<222> LOCATION: (1)..(1)
<223> OTHER INFORMATION: X is Ac5c
<220> FEATURE:
<221> NAME/KEY: misc_feature
<222> LOCATION: (2)..(2)
<223> OTHER INFORMATION: X is Bpa
<220> FEATURE:
<221> NAME/KEY: misc_feature
<222> LOCATION: (3)..(3)
<223> OTHER INFORMATION: X is Aib
<220> FEATURE:
<221> NAME/KEY: misc_feature
<222> LOCATION: (8)..(8)
<223> OTHER INFORMATION: X is Nle
<220> FEATURE:
<221> NAME/KEY: misc_feature
<222> LOCATION: (11)..(11)
<223> OTHER INFORMATION: X is Har
<220> FEATURE:
<221> NAME/KEY: misc_feature
<222> LOCATION: (15)..(15)
<223> OTHER INFORMATION: X is an Amino Group

<400> SEQUENCE: 24

Xaa Xaa Xaa Glu Ile Gln Leu Xaa His Gln Xaa Ala Lys Tyr Xaa
1               5                   10                  15

<210> SEQ ID NO 25
<211> LENGTH: 22
<212> TYPE: PRT
<213> ORGANISM: Artificial sequence
<220> FEATURE:
<223> OTHER INFORMATION: PTH Peptide
<220> FEATURE:
<221> NAME/KEY: misc_feature
<222> LOCATION: (1)..(1)
<223> OTHER INFORMATION: X is Deg
<220> FEATURE:
<221> NAME/KEY: misc_feature
<222> LOCATION: (2)..(2)
<223> OTHER INFORMATION: X is Bpa
<220> FEATURE:
<221> NAME/KEY: misc_feature
<222> LOCATION: (3)..(3)
<223> OTHER INFORMATION: X is Deg
<220> FEATURE:
<221> NAME/KEY: misc_feature
<222> LOCATION: (8)..(8)
<223> OTHER INFORMATION: X is Nle
<220> FEATURE:
<221> NAME/KEY: misc_feature
<222> LOCATION: (11)..(11)
<223> OTHER INFORMATION: X is Har
<220> FEATURE:
<221> NAME/KEY: misc_feature
<222> LOCATION: (22)..(22)
<223> OTHER INFORMATION: X is an Amino Group

<400> SEQUENCE: 25

Xaa Xaa Xaa Glu Ile Gln Leu Xaa His Gln Xaa Ala Lys Trp Leu Ala
1               5                   10                  15

Ser Val Arg Arg Tyr Xaa
            20

<210> SEQ ID NO 26
<211> LENGTH: 21
<212> TYPE: PRT
<213> ORGANISM: Homo sapiens

<400> SEQUENCE: 26

Ser Val Ser Glu Ile Gln Leu Met His Asn Leu Gly Lys His Leu Asn
1               5                   10                  15
```

Ser Met Glu Arg Val
            20

<210> SEQ ID NO 27
<211> LENGTH: 21
<212> TYPE: PRT
<213> ORGANISM: Rattus sp.

<400> SEQUENCE: 27

Ala Val Ser Glu Ile Gln Leu Met His Asn Leu Gly Lys His Leu Ala
1               5                   10                  15

Ser Val Glu Arg Met
            20

<210> SEQ ID NO 28
<211> LENGTH: 20
<212> TYPE: PRT
<213> ORGANISM: Artificial Sequence
<220> FEATURE:
<223> OTHER INFORMATION: N-truncated PTH peptide
<220> FEATURE:
<221> NAME/KEY: misc_feature
<222> LOCATION: (1)..(1)
<223> OTHER INFORMATION: Xaa is Aib
<220> FEATURE:
<221> NAME/KEY: misc_feature
<222> LOCATION: (6)..(6)
<223> OTHER INFORMATION: Xaa is Nle
<220> FEATURE:
<221> NAME/KEY: misc_feature
<222> LOCATION: (9)..(9)
<223> OTHER INFORMATION: Xaa is Har
<220> FEATURE:
<221> NAME/KEY: misc_feature
<222> LOCATION: (20)..(20)
<223> OTHER INFORMATION: Xaa is an Amino Group

<400> SEQUENCE: 28

Xaa Glu Ile Gln Leu Xaa His Gln Xaa Ala Lys Trp Leu Ala Ser Val
1               5                   10                  15

Arg Arg Tyr Xaa
            20

<210> SEQ ID NO 29
<211> LENGTH: 33
<212> TYPE: PRT
<213> ORGANISM: Artificial Sequence
<220> FEATURE:
<223> OTHER INFORMATION: N-truncated PTH peptide
<220> FEATURE:
<221> NAME/KEY: misc_feature
<222> LOCATION: (33)..(33)
<223> OTHER INFORMATION: Xaa is an Amino Group

<400> SEQUENCE: 29

Ile Gln Leu Leu His Asp Lys Gly Lys Ser Ile Gln Asp Leu Arg Arg
1               5                   10                  15

Arg Phe Phe Leu His His Leu Ile Ala Glu Ile His Thr Ala Glu Tyr
                20                  25                  30

Xaa

<210> SEQ ID NO 30
<211> LENGTH: 0
<212> TYPE: PRT

<400> SEQUENCE: 30

000

```
<210> SEQ ID NO 31
<211> LENGTH: 33
<212> TYPE: PRT
<213> ORGANISM: Artificial Sequence
<220> FEATURE:
<223> OTHER INFORMATION: N-truncated PTH peptide
<220> FEATURE:
<221> NAME/KEY: misc_feature
<222> LOCATION: (8)..(8)
<223> OTHER INFORMATION: Trp is in the D form
<220> FEATURE:
<221> NAME/KEY: misc_feature
<222> LOCATION: (33)..(33)
<223> OTHER INFORMATION: Xaa is an Amino Group

<400> SEQUENCE: 31

Ile Gln Leu Leu His Asp Leu Trp Lys Ser Ile Gln Asp Leu Arg Arg
1               5                   10                  15

Arg Phe Phe Leu His His Leu Ile Ala Glu Ile His Thr Ala Glu Tyr
            20                  25                  30

Xaa

<210> SEQ ID NO 32
<211> LENGTH: 16
<212> TYPE: PRT
<213> ORGANISM: Artificial Sequence
<220> FEATURE:
<223> OTHER INFORMATION: PTH peptide
<220> FEATURE:
<221> NAME/KEY: misc_feature
<222> LOCATION: (1)..(1)
<223> OTHER INFORMATION: Xaa is Aib
<220> FEATURE:
<221> NAME/KEY: misc_feature
<222> LOCATION: (3)..(3)
<223> OTHER INFORMATION: Xaa is Aib
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (11)..(11)
<223> OTHER INFORMATION: Xaa is Har
<220> FEATURE:
<221> NAME/KEY: misc_feature
<222> LOCATION: (16)..(16)
<223> OTHER INFORMATION: Xaa is an amino group

<400> SEQUENCE: 32

Xaa Val Xaa Glu Ile Gln Leu Xaa His Gln Xaa Ala Lys Trp Tyr Xaa
1               5                   10                  15
```